(12) United States Patent
Gross et al.

(10) Patent No.: US 7,799,543 B2
(45) Date of Patent: *Sep. 21, 2010

(54) HUMAN TUMOR NECROSIS FACTOR RECEPTOR POLYNUCLEOTIDES

(75) Inventors: Jane A. Gross, Seattle, WA (US);
Wenfeng Xu, Mukilteo, WA (US);
Randal M. Henne, Seattle, WA (US);
Francis J. Grant, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/559,332

(22) Filed: Nov. 13, 2006

(65) Prior Publication Data

US 2007/0178492 A1 Aug. 2, 2007

Related U.S. Application Data

(62) Division of application No. 10/008,063, filed on Nov. 5, 2001, now abandoned.

(60) Provisional application No. 60/315,565, filed on Aug. 29, 2001, provisional application No. 60/301,715, filed on Jun. 28, 2001, provisional application No. 60/257,131, filed on Dec. 20, 2000, provisional application No. 60/246,449, filed on Nov. 7, 2000.

(51) Int. Cl.
*C12N 15/00* (2006.01)
*C07H 21/04* (2006.01)

(52) U.S. Cl. ............... 435/69.1; 536/23.1; 536/23.4

(58) Field of Classification Search .............. None
See application file for complete search history.

(56) References Cited

U.S. PATENT DOCUMENTS

| 5,225,539 | A | 7/1993 | Winter |
| 7,112,421 | B2* | 9/2006 | Ambrose et al. ......... 435/69.7 |
| 2003/0092164 | A1 | 5/2003 | Gross et al. |
| 2004/0072188 | A1 | 4/2004 | Ambrose et al. |
| 2007/0060742 | A1 | 3/2007 | Gross et al. |
| 2007/0066805 | A1 | 3/2007 | Gross et al. |
| 2007/0073041 | A1 | 3/2007 | Gross et al. |
| 2007/0264689 | A1 | 11/2007 | Gross et al. |

OTHER PUBLICATIONS

Thompson, et al. BAFF-R, a newly identified TNF receptor that specifically interacts with BAFF, Sep. 14, 2001, Science 293 (5537): 2107-2111.
Yan et al., Identification of a novel receptor for B Lymphocyte stimulator that is mutated in a mouse strain with sever B cell deficiency, 2001, Current Biology 11(19): 1547-1552.
Gross, et al. TACI and BCMA are redeptors for a TNF homologue implicated in B-cell autoimmune desease, Apr. 27, 2000, Nature 404: 995-999.
Marsters et al., Interaction of the TNF homolugues BLyS and April with the TNF receptor homologues BCMA and TACI, Jun. 29, 2000, Current Biology 10(13): 785-788.
Schneider et al. BAFF, a novel ligand of the tumor cecrosis factor family, stimulates B cell growth Jun. 7, 1999, Journal of Experimental Medicine 189 (11): 1747-1756.
Moore et al., BLyS: Member of the tumor necrosis factor family and B lymphocyte stimulator, Jul. 9, 1999, Science 285: 260-263.
Mukhopadhyay et al., Identification and Characterization of a Novel cytokine, Thank, a TNF Homologue that Activates Apoptosis, Nuclear Factor $_{K}$B, and cJun NH$_2$ Terminal Kinase, J. Biol. Chem., 274(23): 15978-15981, 1999.
Shu et al. TALL-1 is a novel member of the TNF family that is downregulated by mitogens. May 1999, J. Leukoc. Biol. 65(5): 680-683.
U.S. Appl. No. 60/233,152.

* cited by examiner

*Primary Examiner*—Ruixiang Li
(74) *Attorney, Agent, or Firm*—Michelle L. Lewis

(57) ABSTRACT

Tumor necrosis factors and their receptors have proven usefulness in both basic research and as therapeutics. The present invention provides a new human tumor necrosis factor receptor designated as "Ztnfr12."

8 Claims, 1 Drawing Sheet

HUMAN TUMOR NECROSIS FACTOR RECEPTOR POLYNUCLEOTIDES

CROSS-REFERENCE TO RELATED APPLICATIONS

This application is a divisional of U.S. application Ser. No. 10/008,063 filed Nov. 5, 2001 now abandoned, which claims the benefit of U.S. Provisional Application Ser. No. 60/315,565, filed Aug. 29, 2001, U.S. Provisional Application Ser. No. 60/301,715, filed Jun. 28, 2001, U.S. Provisional Application Ser. No. 60/257,131, filed Dec. 20, 2000, and U.S. Provisional Application Ser. No. 60/246,449, filed Nov. 7, 2000, all of which are herein incorporated by reference.

TECHNICAL FIELD

The present invention relates generally to a new protein expressed by human cells. In particular, the present invention relates to a novel gene that encodes a receptor, designated as "Ztnfr12," and to nucleic acid molecules encoding Ztnfr12 polypeptides.

BACKGROUND OF THE INVENTION

Cytokines are soluble, small proteins that mediate a variety of biological effects, including the regulation of the growth and differentiation of many cell types (see, for example, Arai et al., Annu. Rev. Biochem. 59:783 (1990); Mosmann, Curr. Opin. Immunol. 3:311 (1991); Paul and Seder, Cell 76:241 (1994)). Proteins that constitute the cytokine group include interleukins, interferons, colony stimulating factors, tumor necrosis factors, and other regulatory molecules. For example, human interleukin-17 is a cytokine which stimulates the expression of interleukin-6, intracellular adhesion molecule 1, interleukin-8, granulocyte macrophage colony-stimulating factor, and prostaglandin E2 expression, and plays a role in the preferential maturation of CD34+ hematopoietic precursors into neutrophils (Yao et al., J. Immunol. 155:5483 (1995); Fossiez et al., J. Exp. Med. 183:2593 (1996)).

Receptors that bind cytokines are typically composed of one or more integral membrane proteins that bind the cytokine with high affinity and transduce this binding event to the cell through the cytoplasmic portions of the certain receptor subunits. Cytokine receptors have been grouped into several classes on the basis of similarities in their extracellular ligand binding domains. For example, the receptor chains responsible for binding and/or transducing the effect of interferons are members of the type II cytokine receptor family, based upon a characteristic 200 residue extracellular domain.

Cellular interactions, which occur during an immune response, are regulated by members of several families of cell surface receptors, including the tumor necrosis factor receptor (TNFR) family. The TNFR family consists of a number of integral membrane glycoprotein receptors many of which, in conjunction with their respective ligands, regulate interactions between different hematopoietic cell lineages (see, for example, Cosman, Stem Cells 12:440 (1994); Wajant et al., Cytokine Growth Factor Rev. 10:15 (1999); Yeh et al., Immunol. Rev. 169:283 (1999); Idriss and Naismith, Microsc. Res. Tech. 50:184 (2000)).

One such receptor is TACI, transmembrane activator and CAML-interactor (von Bülow and Bram, Science 228:138 (1997); PCT publication WO 98/39361). TACI is a membrane bound receptor, which has an extracellular domain containing two cysteine-rich pseudo-repeats, a transmembrane domain and a cytoplasmic domain that interacts with CAML (calcium-modulator and cyclophilin ligand), an integral membrane protein located at intracellular vesicles which is a co-inducer of NF-AT activation when overexpressed in Jurkat cells. TACI is associated with B cells and a subset of T cells.

The demonstrated in vivo activities of tumor necrosis factor receptors illustrate the clinical potential of, and need for, other such receptors, as well as tumor necrosis factor receptor agonists, and antagonists.

BRIEF SUMMARY OF THE INVENTION

The present invention provides a novel tumor necrosis factor receptor, designated "Ztnfr12." The present invention also provides Ztnfr12 polypeptides and Ztnfr12 fusion proteins, as well as nucleic acid molecules encoding such polypeptides and proteins, and methods for using these nucleic acid molecules and amino acid sequences.

DETAILED DESCRIPTION OF THE INVENTION

1. Overview

Figure 1:
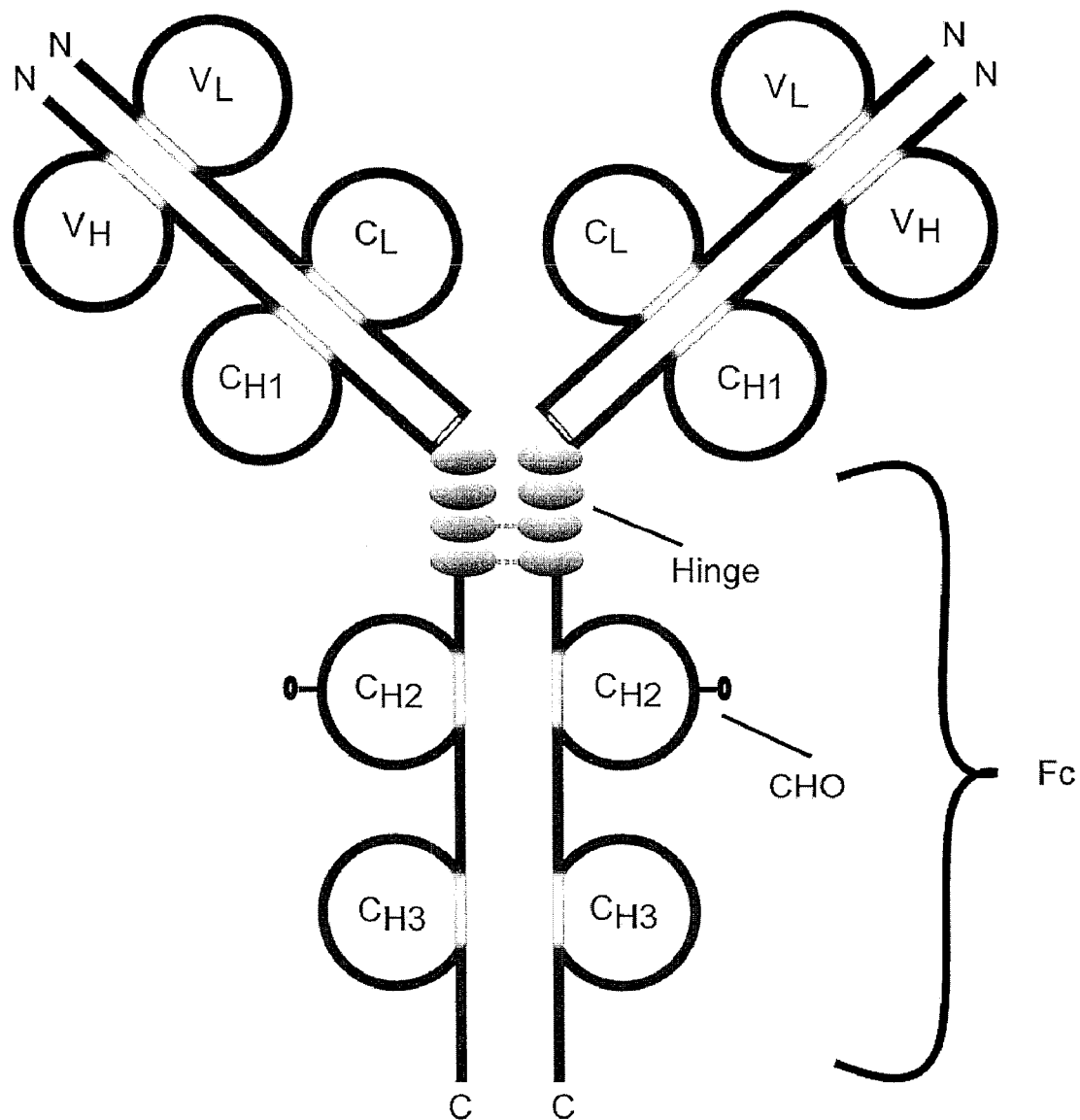
FIG. 1 is a schematic diagram of an immunoglobulin of the IgG1 subclass. $C_L$: light chain constant region; $C_{H1}$, $C_{H2}$, $C_{H3}$: heavy chain constant regions; $V_L$: light chain variable region; $V_H$: heavy chain variable region; CHO: carbohydrate; N: amino terminus; C: carboxyl terminus.

ZTNF4 is a member of the tumor necrosis factor (TNF) ligand family (SEQ ID NO:5). This molecule has also been designated as "BAFF," "BLyS," "TALL-1," and "THANK" (Moore et al., Science 285:269 (1999); Mukhopadhyay et al., J. Biol. Chem. 274:15978 (1999); Schneider et al., J. Exp. Med. 189:1747 (1999); Shu et al., J. Leukoc. Biol. 65:680 (1999)). Two receptors have been identified that bind with ZTNF4: the transmembrane activator and CAML interactor (TACI) and the B-cell maturation receptor (BCMA) (Gross et al., Nature 404:995 (2000)). Biotinylated ZTNF4 was used to identify potential new receptors for this ligand. In these studies, the binding of biotinylated ZTNF4 to a panel of tumor cells was measured using flow cytometry. Surprisingly, ZTNF4 was found to bind to a human B-lymphoid precursor cell line (REH cells), even though there was little binding of the cells with either monoclonal antibodies to TACI, or polyclonal antibodies to BCMA. Similar results were found with BJAB cells, derived from a human lymphoma. These observations suggested that ZTNF4 bound with a receptor other than TACI or BCMA.

To investigate this possibility further, $I^{125}$-labeled ZTNF4 was bound to the B-lymphoid precursor cells, and crosslinked to cell surface molecules. Treatment with anti-ZTNF4 polyclonal antibodies produced a radioactive precipitate, whereas treatment with anti-TACI or anti-BCMA polyclonal antibodies did not produce a radioactive precipitate. Thus, this data supported the hypothesis that a new receptor accounted for the binding of ZTNF4 to the cells. The receptor, designated as "Ztnfr12," was isolated as described in Example 1. Binding studies indicated that the new receptor binds ZTNF4, but not a ligand designated as "ZTNF2" (SEQ ID NO:6). ZTNF2 has also been designated as "APRIL" and "TNRF death ligand-1" (Hahne et al., J. Exp. Med. 188:1185 (1998); Kelly et al., Cancer Res. 60:1021 (2000)).

The binding characteristics of Ztnfr12 were also investigated using recombinant host cells. Baby hamster kidney cells were transfected with an expression vector that comprised Ztnfr12 encoding sequences, and the transfected cells were used in a binding study with $I^{125}$-labeled ZTNF4. Binding studies and Scatchard analyses indicated that the Kd of ZTNF4 for Ztnfr12 is 1.0 nM, which is comparable to the Kd of ZTNF4 for TACI receptor (1.25 nM) expressed by baby hamster kidney cells transfected with a TACI expression vector. The transfected cells expressed approximately $150 \times 10^6$ Ztnfr12 cell surface receptors per cell.

ZTNF4 appears to bind to virtually all mature $CD19^+$ peripheral B cells, weakly to immature B cells in the bone marrow, and to most transformed B-cell lines. However, several B lymphomas, REH and BJAB for example, bind ZTNF4 but do not express appreciable levels of either TACI or BCMA. In addition, TACI and BCMA surface expression and ZTNF4 binding were determined on cells isolated from human tonsil, peripheral blood, and bone marrow using flow cytometry. The results indicate that TACI and BCMA are expressed at the highest levels on the most immature B cell population, $IgM^+IgD^{lo}$, in human tonsil and peripheral blood. Expression levels of both receptors decrease on the surface of the more mature $IgM^+IgD^+$ B cells and are found at very low levels on $IgM^-IgD^+$ B cells, a population that represents the most mature stage of B cell maturation. However, ZTNF4 ligand binds to virtually all mature B cells at high levels. Taken together these data implicate the presence of additional receptors for ZTNF4 on some B cell tumors and peripheral human B cells. These data suggest that Ztnfr12 is expressed at highest levels on the most mature $IgM^-IgD^+$ B cells and may account for the high levels of zTNF4 binding to this population.

An illustrative nucleotide sequence that encodes Ztnfr12 is provided by SEQ ID NO:1. The encoded polypeptide has the following amino acid sequence: MRRGPRSLRG RDAPAPTPCV PAECFDLLVR HCVACGLLRT PRPKPAGASS PAPRTALQPQ ESVGAGAGEA ALPLPGLLFG APALLGLALV LALVLVGLVS WRRRQRRLRG ASSAEAPDGD KDAPEPLDKV IILSPGISDA TAPAWPPPGE DPGTTPPGHS VPVPATELGS TELVTTKTAG PEQQ (SEQ ID NO:2). Features of the Ztnfr12 polypeptide include an extracellular domain that comprises amino acid residues 1 to 69 of SEQ ID NO:2 or amino acid residues 1 to 79 of SEQ ID NO:2, a transmembrane domain that comprises amino acid residues 70 to 100 of SEQ ID NO:2 or amino acid residues 80 to 100 of SEQ ID NO:2, and an intracellular domain at about amino acid residues 101 to 184 of SEQ ID NO:2.

A nucleotide sequence that includes the Ztnfr12 gene is provided by SEQ ID NO:9. The Ztnfr12 gene comprises three exons. With reference to the amino acid sequence of SEQ ID NO:2, exon 1 encodes amino acid residues 1 to the first nucleotide of the codon for amino acid 46, exon 2 encodes the remainder of amino acid 46 to the first nucleotide of the codon for amino acid 123, and exon 3 encodes the remainder of amino acid 123 to amino acid 184. The 3'-untranslated region includes nucleotides 2405 to about 5720 of SEQ ID NO:9. Table 1 provides further features of this nucleotide sequence.

TABLE 1

| Feature | SEQ ID NO: 9 | Corresponding region of SEQ ID NO: 1 |
| --- | --- | --- |
| Exon 1 | 1001-1136 | 27-162 |
| Intron 1 | 1137-1442 | |
| Exon 2 | 1443-1673 | 163-393 |
| Intron 2 | 1674-2219 | |
| Exon 3 | 2220-2404 | 394-578 |

The Ztnfr12 gene resides in chromosome 22q13.2, and Ztnfr12 is expressed in most lymph tissues (e.g. lymphoid node tissue), B-cell tumors, and germinal center B-cells. Northern and dot blot analyses revealed that Ztnfr12 gene expression is detectable in spleen, lymph node, peripheral blood lymphocytes, kidney, heart, liver, skeletal muscle, pancreas, adrenal gland, testis, brain, uterus, stomach, bone marrow, trachea thymus, placenta, fetal liver and Raji cells. The strongest signals were associated with spleen and lymph node tissues, whereas weak signals were associated with brain, uterine, and placental tissue. Accordingly, Ztnfr12 antibodies and nucleic acid probes can be used to differentiate between these tissues.

As described below, the present invention provides isolated polypeptides comprising an amino acid sequence that is at least 70%, at least 80%, or at least 90% identical to a reference amino acid sequence selected from the group consisting of: (a) amino acid residues 7 to 69 of SEQ ID NO:2, (b) amino acid residues 7 to 79 of SEQ ID NO:2, (c) amino acid residues 7 to 39 of SEQ ID NO:2, (d) amino acid residues 19 to 35 of SEQ ID NO:2, (e) amino acid residues 1 to 69 of SEQ ID NO:2, (f) amino acid residues 1 to 79 of SEQ ID NO:2, (g) amino acid residues 1 to 39 of SEQ ID NO:2, (h) amino acid residues 1 to 71 of SEQ ID NO:2, (i) amino acid residues 7 to 71 of SEQ ID NO:2, (j) amino acid residues 70 to 100 of SEQ ID NO:2, (k) amino acid residues 80 to 100 of SEQ ID NO:2, (l) amino acid residues 101 to 184 of SEQ ID NO:2, and (m) the amino acid sequence of SEQ ID NO:2. Certain Ztnfr12 polypeptides specifically bind with an antibody that specifically binds with a polypeptide consisting of the amino acid sequence of SEQ ID NO:2. Certain Ztnfr12 polypeptides specifically bind ZTNF4, while other polypeptides specifically bind ZTNF4 but do not specifically bind ZTNF2. Illustrative Ztnfr12 polypeptides include polypeptides comprising, or consisting of, amino acid residues 7 to 69 of SEQ ID NO:2, amino acid residues 7 to 79 of SEQ ID NO:2, amino acid residues 7 to 39 of SEQ ID NO:2, amino acid residues 19 to 35 of SEQ ID NO:2, amino acid residues 1 to 69 of SEQ ID NO:2, amino acid residues 1 to 79 of SEQ ID NO:2, amino acid residues 1 to 71 of SEQ ID NO:2, amino acid residues 7 to 71 of SEQ ID NO:2, amino acid residues 1 to 39 of SEQ ID NO:2, amino acid residues 80 to 100 of SEQ ID NO:2, amino acid residues 70 to 100 of SEQ ID NO:2, amino acid residues 101 to 184 of SEQ ID NO:2, and the amino acid sequence of SEQ ID NO:2. The present invention also provides isolated polypeptides comprising at least 15, or at least 30, contiguous amino acid residues of amino acid residues 7 to 69 of SEQ ID NO:2, amino acid residues 7 to 79 of SEQ ID NO:2, amino acid residues 7 to 39 of SEQ ID NO:2, amino acid residues 19 to 35 of SEQ ID NO:2, amino acid residues 1 to 69 of SEQ ID NO:2, amino acid residues 1 to 79 of SEQ ID NO:2, amino acid residues 1 to 71 of SEQ ID NO:2, amino acid residues 7 to 71 of SEQ ID NO:2, or amino acid residues 1 to 39 of SEQ ID NO:2.

The present invention further provides polypeptides encoded by at least one Ztnfr12 exon. For example, such polypeptides can consist of the following amino acid sequences of SEQ ID NO:2: amino acid residues 1 to 45, amino acid residues 47 to 122, and amino acid residues 124 to 184.

The present invention also includes variant Ztnfr12 polypeptides, wherein the amino acid sequence of the variant polypeptide shares an identity with amino acid residues 7 to 69 of SEQ ID NO:2, amino acid residues 7 to 79 of SEQ ID NO:2, amino acid residues 7 to 39 of SEQ ID NO:2, amino acid residues 19 to 35 of SEQ ID NO:2, amino acid residues 1 to 69 of SEQ ID NO:2, amino acid residues 1 to 79 of SEQ ID NO:2, amino acid residues 1 to 39 of SEQ ID NO:2, amino acid residues 1 to 71 of SEQ ID NO:2, amino acid residues 7 to 71 of SEQ ID NO:2, or amino acid residues 1 to 184 of SEQ ID NO:2, selected from the group consisting of at least 70% identity, at least 80% identity, at least 90% identity, at least 95% identity, or greater than 95% identity, and wherein any difference between the amino acid sequence of the variant polypeptide and the corresponding amino acid sequence of SEQ ID NO:2 is due to one or more conservative amino acid substitutions.

The present invention further provides antibodies and antibody fragments that specifically bind with such polypeptides. Exemplary antibodies include polyclonal antibodies, murine monoclonal antibodies, humanized antibodies derived from murine monoclonal antibodies, and human monoclonal antibodies. Illustrative antibody fragments include F(ab')$_2$, F(ab)$_2$, Fab', Fab, Fv, scFv, and minimal recognition units. The present invention further includes compositions comprising a carrier and a peptide, polypeptide, antibody, or anti-idiotype antibody described herein.

The present invention also provides isolated nucleic acid molecules that encode a Ztnfr12 polypeptide, wherein the nucleic acid molecule is selected from the group consisting of: (a) a nucleic acid molecule comprising the nucleotide sequence of SEQ ID NO:3, (b) a nucleic acid molecule encoding an amino acid sequence that comprises amino acid residues 7 to 69 of SEQ ID NO:2, amino acid residues 7 to 79 of SEQ ID NO:2, amino acid residues 7 to 39 of SEQ ID NO:2, amino acid residues 19 to 35 of SEQ ID NO:2, amino acid residues 1 to 69 of SEQ ID NO:2, amino acid residues 1 to 79 of SEQ ID NO:2, amino acid residues 1 to 39 of SEQ ID NO:2, amino acid residues 1 to 71 of SEQ ID NO:2, amino acid residues 7 to 71 of SEQ ID NO:2, or amino acid residues 1 to 184 of SEQ ID NO:2, and (c) a nucleic acid molecule that remains hybridized following stringent wash conditions to a nucleic acid molecule comprising the nucleotide sequence of nucleotides 27 to 578 of SEQ ID NO:1, the nucleotide sequence of nucleotides 27 to 233 of SEQ ID NO:1, the complement of the nucleotide sequence of nucleotides 27 to 578 of SEQ ID NO:1, or the complement of the nucleotide sequence of nucleotides 27 to 233 of SEQ ID NO:1. Illustrative nucleic acid molecules include those in which any difference between the amino acid sequence encoded by nucleic acid molecule (c) and the corresponding amino acid sequence of SEQ ID NO:2 is due to a conservative amino acid substitution.

The present invention further contemplates isolated nucleic acid molecules that comprise nucleotides 27 to 578 of SEQ ID NO:1 (which encodes amino acid residues 1 to 184 of SEQ ID NO:2), nucleotides 27 to 233 of SEQ ID NO:1 (which encodes amino acid residues 1 to 69 of SEQ ID NO:2), nucleotides 27 to 263 of SEQ ID NO:1 (which encodes amino acid residues 1 to 79 of SEQ ID NO:2), nucleotides 45 to 233 of SEQ ID NO:1 (which encodes amino acid residues 7 to 69 of SEQ ID NO:2), nucleotides 45 to 263 of SEQ ID NO:1 (which encodes amino acid residues 7 to 79 of SEQ ID NO:2), nucleotides 45 to 143 of SEQ ID NO:1 (which encodes amino acid residues 7 to 39 of SEQ ID NO:2), nucleotides 81 to 131 of SEQ ID NO:1 (which encodes amino acid residues 19 to 35 of SEQ ID NO:2), nucleotides 27 to 239 of SEQ ID NO:1 (which encodes amino acid residues 1 to 71 of SEQ ID NO:2), nucleotides 45 to 239 of SEQ ID NO:1 (which encodes amino acid residues 7 to 71 of SEQ ID NO:2), and nucleotides 327 to 578 of SEQ ID NO:1 (which encodes amino acid residues 101 to 184 of SEQ ID NO:2).

The present invention also provides nucleic acid molecules that consist of the nucleotide sequence of a Ztnfr12 exon or intron. The nucleotide sequences of these exons and introns are identified in Table 1.

The present invention also includes vectors and expression vectors comprising such nucleic acid molecules. Such expression vectors may comprise a transcription promoter, and a transcription terminator, wherein the promoter is operably linked with the nucleic acid molecule, and wherein the nucleic acid molecule is operably linked with the transcription terminator. The present invention further includes recombinant host cells and recombinant viruses comprising these vectors and expression vectors. Illustrative host cells include bacterial, avian, yeast, fungal, insect, mammalian, and plant cells. Recombinant host cells comprising such expression vectors can be used to produce Ztnfr12 polypeptides by culturing such recombinant host cells that comprise the expression vector and that produce the Ztnfr12 protein, and, optionally, isolating the Ztnfr12 protein from the cultured recombinant host cells. The present invention further includes the products of such processes.

The present invention also provides polypeptides comprising amino acid residues 1 to 69 of SEQ ID NO:13, polypeptides comprising at least 10, at least 15, at least 20, at least 25, or at least 30 consecutive amino acid residues of amino acid residues 1 to 69 of SEQ ID NO:13, polypeptides comprising amino acid residues 21 to 38 of SEQ ID NO:13, fusion proteins comprising amino acid residues 1 to 69 of SEQ ID NO:13, nucleic acid molecules encoding such amino acid sequences, expression vectors comprising such nucleic acid molecules, and recombinant host cells comprising such expression vectors. The present invention further includes methods for producing murine Ztnfr12 polypeptides using such recombinant host cells.

An alignment of the amino acid sequences of TACI, BCMA, human Ztnfr12, and murine Ztnfr12 revealed the following motif in the extracellular domains: C[NVPS][QPE][TAEN][EQ][CY][FW]D[PLS]L[VL][RGH][NHTA]C[VMI][SAP]C, wherein acceptable amino acids for a given position are indicated within square brackets (SEQ ID NO:46). The present invention includes polypeptides having an amino acid sequence that consists of this motif, wherein the polypeptides bind ZTNF4. The present invention also includes antibodies that bind to a polypeptide having an amino acid sequence that consists of this motif.

In addition, the present invention provides pharmaceutical compositions comprising a pharmaceutically acceptable carrier and at least one of such an expression vector or recombinant virus comprising such expression vectors. The present invention further includes pharmaceutical compositions, comprising a pharmaceutically acceptable carrier and a polypeptide described herein.

The present invention also contemplates methods for detecting the presence of Ztnfr12 RNA in a biological sample, comprising the steps of (a) contacting a Ztnfr12 nucleic acid probe under hybridizing conditions with either (i) test RNA molecules isolated from the biological sample, or (ii) nucleic acid molecules synthesized from the isolated RNA molecules, wherein the probe has a nucleotide sequence comprising a portion of the nucleotide sequence of SEQ ID NO:1, or its complement, and (b) detecting the formation of hybrids of the nucleic acid probe and either the test RNA molecules or the synthesized nucleic acid molecules, wherein the presence of the hybrids indicates the presence of Ztnfr12 RNA in the biological sample. For example, suitable probes consist of the following nucleotide sequences: nucleotides 27 to 578 of SEQ ID NO:1, and nucleotides 27 to 233 of SEQ ID NO:1.

Other suitable probes consist of the complement of these nucleotide sequences, or a portion of the nucleotide sequences as described herein, or their complements.

The present invention further provides methods for detecting the presence of Ztnfr12 polypeptide in a biological sample, comprising the steps of: (a) contacting the biological sample with an antibody or an antibody fragment that specifically binds with a polypeptide consisting of the amino acid sequence of SEQ ID NO:2, wherein the contacting is performed under conditions that allow the binding of the antibody or antibody fragment to the biological sample, and (b) detecting any of the bound antibody or bound antibody fragment. Such an antibody or antibody fragment may further comprise a detectable label selected from the group consisting of radioisotope, fluorescent label, chemiluminescent label, enzyme label, bioluminescent label, and colloidal gold.

The present invention also provides kits for performing these detection methods. For example, a kit for detection of Ztnfr12 gene expression may comprise a container that comprises a nucleic acid molecule, wherein the nucleic acid molecule is selected from the group consisting of: (a) a nucleic acid molecule comprising the nucleotide sequence of nucleotides 27 to 233 of SEQ ID NO:1, (b) a nucleic acid molecule comprising the complement of nucleotides 27 to 233 of the nucleotide sequence of SEQ ID NO:1, and (c) a nucleic acid molecule that is a fragment of (a) or (b) consisting of at least eight nucleotides. Such a kit may also comprise a second container that comprises one or more reagents capable of indicating the presence of the nucleic acid molecule. On the other hand, a kit for detection of Ztnfr12 protein may comprise a container that comprises an antibody, or an antibody fragment, that specifically binds with a polypeptide consisting of the amino acid sequence of SEQ ID NO:2.

The present invention also contemplates anti-idiotype antibodies, or anti-idiotype antibody fragments, that specifically bind an antibody or antibody fragment that specifically binds a polypeptide consisting of the amino acid sequence of SEQ ID NO:2. An exemplary anti-idiotype antibody binds with an antibody that specifically binds a polypeptide consisting of amino acid residues 1 to 69 of SEQ ID NO:2, amino acid residues 1 to 79 of SEQ ID NO:2, amino acid residues 7 to 69 of SEQ ID NO:2, amino acid residues 7 to 79 of SEQ ID NO:2, amino acid residues 1 to 71 of SEQ ID NO:2, or amino acid residues 7 to 71 of SEQ ID NO:2.

The present invention also provides fusion proteins, comprising a Ztnfr12 polypeptide and an immunoglobulin moiety. In such fusion proteins, the immunoglobulin moiety may be an immunoglobulin heavy chain constant region, such as a human $F_c$ fragment. The present invention further includes isolated nucleic acid molecules that encode such fusion proteins.

The present invention further includes methods for inhibiting, in a mammal, the activity of a ligand that binds Ztnfr12 (e.g., ZTNF4), comprising administering to the mammal a composition comprising at least one of: (a) soluble Ztnfr12 receptor, (b) an antibody or antibody fragment which specifically binds with the extracellular domain of Ztnfr12, and (c) a fusion protein comprising the extracellular domain of Ztnfr12. As an illustration, such a composition can be used to treat disorders and diseases associated with B lymphocytes, activated B lymphocytes, or resting B lymphocytes. Examples of B cell lymphomas that may be treated with the molecules described herein include Burkitt's lymphoma, Non-Burkitt's lymphoma, Non-Hodgkin's lymphoma, multiple myeloma, follicular lymphoma, acute lymphoblastic leukemia, chronic lymphocytic leukemia, large cell lymphoma, marginal zone lymphoma, mantle cell lymphoma, large cell lymphoma (e.g., immunoblastic lymphoma), small lymphocytic lymphoma, and other B cell lymphomas. Such compositions can also be used to treat T cell lymphomas, including lymphoblastic lymphoma, anaplastic large cell lymphoma, cutaneous T cell lymphoma, peripheral T cell lymphomas, angioimmunoblastic lymphoma, angiocentric lymphoma, intestinal T cell lymphoma, adult T cell lymphoma, adult T cell leukemia, and the like.

For example, the present invention includes methods for inhibiting the proliferation of tumor cells (e.g., B cell lymphoma cells or T cell lymphoma cells), comprising administering to the tumor cells a composition that comprises at least one of: (a) soluble Ztnfr12 receptor, (b) an antibody or antibody fragment which specifically binds with the extracellular domain of Ztnfr12, and (c) a fusion protein comprising the extracellular domain of Ztnfr12. Such a composition can be administered to cells cultured in vitro. Alternatively, the composition can be a pharmaceutical composition, and wherein the pharmaceutical composition is administered to a subject, which has a tumor.

One example of a fusion protein is a Ztnfr12-immunoglobulin fusion protein that comprises the extracellular domain of Ztnfr12 is a Ztnfr12 polypeptide the comprises a fragment of a polypeptide comprising amino acid residues 1 to 69 of SEQ ID NO:2, and an immunoglobulin moiety comprising a constant region of an immunoglobulin. An illustrative immunoglobulin moiety comprises a heavy chain constant region. A Ztnfr12-immunoglobulin fusion protein can be a monomer, a dimer, or other configuration, as discussed below.

In another example, a composition that comprises an anti-Ztnfr12 antibody component is administered to tumor cells to inhibit the proliferation of the cells. The composition can be administered to cells cultured in vitro, or the composition can be a pharmaceutical composition that is administered to a subject, which has a tumor. Such compositions can comprise an anti-Ztnf12 antibody component that is a naked Ztnf12 antibody, or such compositions can comprise an anti-Ztnf12 antibody component that is a naked Ztnf12 antibody fragment. Moreover, the composition can comprise an immunoconjugate that comprises an anti-Ztnf12 antibody component and a therapeutic agent. Illustrative therapeutic agents include a chemotherapeutic drug, cytotoxin, immunomodulator, chelator, boron compound, photoactive agent, photoactive dye, and radioisotope. Such compositions may comprise an antibody fusion protein that comprises an anti-Ztnfr12 antibody component and either an immunomodulator or a cytotoxic polypeptide. Another form of composition is a multispecific antibody, which comprises an anti-Ztnf12 naked antibody component, and at least one of an anti-BCMA naked antibody component, and an anti-TACI naked antibody component. An illustrative multispecific antibody composition comprises bispecific antibodies that bind Ztnfr12, and at least one of BCMA and TACI. Multispecific antibody compositions can further comprise a therapeutic agent. Moreover, a multispecific antibody composition can comprise: (a) an anti-Ztnfr12 antibody fusion protein that comprises either an immunomodulator or a cytotoxic polypeptide, and (b) at least one of an anti-BCMA antibody component or an anti-TACI antibody component.

Polypeptides comprising a Ztnfr12 extracellular domain or anti-Ztnfr12 antibodies can be used to treat an autoimmune disease. Examples of autoimmune diseases include systemic lupus erythomatosis, myasthenia gravis, multiple sclerosis, insulin dependent diabetes mellitus, and rheumatoid arthritis. Polypeptides comprising a Ztnfr12 extracellular domain or anti-Ztnfr12 antibodies can also be used to treat asthma, bronchitis, emphysema, and end stage renal failure or renal disease. Illustrative renal diseases include glomerulonephritis, vasculitis, chronic lymphoid leukemia, nephritis, and pyelonephritis. Polypeptides comprising a Ztnfr12 extracellular domain or anti-Ztnfr12 antibodies can further be used to treat renal neoplasms, multiple myelomas, lymphomas, light chain neuropathy, or amyloidosis.

The present invention also includes methods for inhibiting ZTNF4 activity, wherein the ZTNF4 activity is associated with effector T cells. Within a related method, the ZTNF4 activity is associated with regulating immune response. Within another method, the ZTNF4 activity is associated with immunosuppression. Within yet another method, the immunosuppression is associated with graft rejection, graft verses host disease, or inflammation. Within still another method, the immunosuppression is associated with autoimmune disease. As an illustration, the autoimmune disease may be insulin-dependent diabetes mellitus or Crohn's disease. In yet other methods, immunosuppression is associated with inflammation. Such inflammation can be associated with, for example, joint pain, swelling, anemia, or septic shock.

The present invention also includes methods for detecting a chromosome 22q13.2 abnormality in a subject by (a) amplifying, from genomic DNA isolated from a biological sample of the subject, nucleic acid molecules that either (i) comprise a nucleotide sequence that encodes at least one of Ztnfr12 exons 1 to 3, or that (ii) comprise a nucleotide sequence that is the complement of (i), and (b) detecting a mutation in the amplified nucleic acid molecules, wherein the presence of a mutation indicates a chromosome 22q13.2 abnormality. In variations of these methods, the detecting step is performed by comparing the nucleotide sequence of the amplified nucleic acid molecules to the nucleotide sequence of SEQ ID NO:1 or SEQ ID NO:9.

The present invention further provides methods for detecting a chromosome 22q13.2 abnormality in a subject comprising: (a) amplifying, from genomic DNA isolated from a biological sample of the subject, a segment of the Ztnfr12 gene that comprises either the nucleotide sequence of at least one of intron 1 and intron 2, or the complementary nucleotide sequence of at least one of intron 1 and intron 2, and (b) detecting a mutation in the amplified nucleic acid molecules, wherein the presence of a mutation indicates a chromosome 22q13.2 abnormality. In variations of these methods, the detecting step is performed by binding the amplified Ztnfr12 gene segments to a membrane, and contacting the membrane with a nucleic acid probe under hybridizing conditions of high stringency, wherein the absence of hybrids indicates an abnormality associated with the expression of Ztnfr12, or a mutation in chromosome 22q13.2. As an illustration, a suitable nucleic acid probe can comprise the nucleotide sequence (or the complement of the nucleotide sequence) of any one of introns 1 and 2.

Examples of mutations or alterations of the Ztnfr12 gene or its gene products include point mutations, deletions, insertions, and rearrangements. Another example of a Ztnfr12 gene mutation is aneuploidy. The present invention also includes methods for detecting a chromosome 22q13.2 abnormality in a subject comprising the identification of an alteration in the region upstream of the first exon of the Ztnfr12 gene (e.g., within nucleotides 1 to 1000 of SEQ ID NO:9) using the detection methods described herein.

These and other aspects of the invention will become evident upon reference to the following detailed description. In addition, various references are identified below and are incorporated by reference in their entirety.

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' is complementary to 5' CCCGTGCAT 3'.

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., Mol. Endocrinol. 7:551 (1993)), cyclic AMP response elements (CREs), serum response elements (SREs; Treisman, Seminars in Cancer Biol. 1:47 (1990)), glucocorticoid response elements (GREs), and binding sites for other transcription factors, such as CRE/ATF (O'Reilly et al., J. Biol. Chem. 267:19938 (1992)), AP2 (Ye et al., J. Biol. Chem. 269:25728 (1994)), SP1, cAMP response element binding protein (CREB; Loeken, Gene Expr. 3:253 (1993)) and octamer factors (see, in general, Watson et al., eds., Molecular Biology of the Gene, 4th ed. (The Benjamin/Cummings Publishing Company, Inc. 1987), and Lemaigre and Rousseau, Biochem. J. 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides." A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, or bacteriophage, which has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces Ztnfr12 from an expression vector. In contrast, Ztnfr12 can be produced by a cell that is a "natural source" of Ztnfr12, and that lacks an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a Ztnfr12-immunoglobulin fusion protein comprises a Ztnfr12 receptor moiety and an immunoglobulin moiety. As used herein, a "Ztnfr12 receptor moiety" is a portion of the extracellular domain of the Ztnfr12 receptor that binds at least one of ZTNF2 or ZTNF4. The phrase an "immunoglobulin moiety" refers to a polypeptide that comprises a constant region of an immunoglobulin. For example, the immunoglobulin moiety can comprise a heavy chain constant region. The term "Ztnfr12-Fc" fusion protein refers to a Ztnfr12-immunoglobulin fusion protein in which the immunoglobulin moiety comprises immunoglobulin heavy chain constant regions, $C_{H2}$ and $C_{H3}$.

The term "receptor" denotes a cell-associated protein that binds to a bioactive molecule termed a "ligand." This interaction mediates the effect of the ligand on the cell. In the context of Ztnfr12 receptor binding, the phrase "specifically binds" or "specific binding" refers to the ability of the ligand to competitively bind with the receptor. For example, ZTNF4 specifically binds with the Ztnfr12 receptor, and this can be shown by observing competition for the Ztnfr12 receptor between detectably labeled ZTNF4 and unlabeled ZTNF4.

Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

As used herein, the term "immunomodulator" includes cytokines, stem cell growth factors, lymphotoxins, co-stimulatory molecules, hematopoietic factors, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9 \text{ M}^{-1}$.

An "anti-idiotype antibody" is an antibody that binds with the variable region domain of an immunoglobulin. In the present context, an anti-idiotype antibody binds with the variable region of an anti-Ztnfr12 antibody, and thus, an anti-idiotype antibody mimics an epitope of Ztnfr12.

An "antibody fragment" is a portion of an antibody such as $F(ab')_2$, $F(ab)_2$, Fab', Fab, and the like. Regardless of structure, an antibody fragment binds with the same antigen that is recognized by the intact antibody. For example, an anti-Ztnfr12 monoclonal antibody fragment binds with an epitope of Ztnfr12.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain.

As used herein, a "therapeutic agent" is a molecule or atom, which is conjugated to an antibody moiety to produce a conjugate, which is useful for therapy. Examples of therapeutic agents include drugs, toxins, immunomodulators, chelators, boron compounds, photoactive agents or dyes, and radioisotopes.

A "detectable label" is a molecule or atom, which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., EMBO J. 4:1075 (1985); Nilsson et al., Methods Enzymol. 198:3 (1991)), glutathione S transferase (Smith and Johnson, Gene 67:31 (1988)), Glu-Glu affinity tag (Grussenmeyer et al., Proc. Natl. Acad. Sci. USA 82:7952 (1985)), substance P, FLAG peptide (Hopp et al., Biotechnology 6:1204 (1988)), streptavidin binding peptide, or other antigenic epitope or binding domain. See, in general, Ford et al., Protein Expression and Purification 2:95 (1991). DNA molecules encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term "antibody component" includes both an entire antibody and an antibody fragment.

A "bispecific antibody" has binding sites for two different antigens within a single antibody molecule.

A "multispecific antibody composition" comprises antibody components that have binding sites for two different antigens. For example, a multispecific antibody composition can comprise bispecific antibody components, or a multispecific antibody composition can comprise at least two antibody components that bind with different antigens.

An "immunoconjugate" is a conjugate of an antibody component with a therapeutic agent or a detectable label.

As used herein, the term "antibody fusion protein" refers to a recombinant molecule that comprises an antibody component and a Ztnfr12 polypeptide component. Examples of an antibody fusion protein include a protein that comprises a Ztnfr12 extracellular domain, and either an Fc domain or an antigen-biding region.

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

An "antigenic peptide" is a peptide, which will bind a major histocompatibility complex molecule to form an MHC-peptide complex, which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell, which binds or expresses the antigen. The antigenic peptide can be bound in the context of a class I or class II major histocompatibility complex molecule, on an antigen presenting cell or on a target cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

An "anti-sense oligonucleotide specific for Ztnfr12" or a "Ztnfr12 anti-sense oligonucleotide" is an oligonucleotide having a sequence (a) capable of forming a stable triplex with a portion of the Ztnfr12 gene, or (b) capable of forming a stable duplex with a portion of an mRNA transcript of the Ztnfr12 gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

The term "variant Ztnfr12 gene" refers to nucleic acid molecules that encode a polypeptide having an amino acid sequence that is a modification of SEQ ID NO:2. Such variants include naturally-occurring polymorphisms of Ztnfr12 genes, as well as synthetic genes that contain conservative amino acid substitutions of the amino acid sequence of SEQ ID NO:2. Additional variant forms of Ztnfr12 genes are nucleic acid molecules that contain insertions or deletions of the nucleotide sequences described herein. A variant Ztnfr12 gene can be identified, for example, by determining whether the gene hybridizes with a nucleic acid molecule having the nucleotide sequence of SEQ ID NO:1, or its complement, under stringent conditions.

Alternatively, variant Ztnfr12 genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, The Internet and the New Biology: Tools for Genomic and Molecular Research (ASM Press, Inc. 1997), Wu et al. (eds.), "Information Superhighway and Computer Databases of Nucleic Acids and Proteins," in Methods in Gene Biotechnology, pages 123-151 (CRC Press, Inc. 1997), and Bishop (ed.), Guide to Human Genome Computing, 2nd Edition (Academic Press, Inc. 1998)). Particular methods for determining sequence identity are described below.

A variant Ztnfr12 gene or variant Ztnfr12 polypeptide, a variant gene or polypeptide encoded by a variant gene may be functionally characterized by at least one of: the ability to bind specifically to an anti-Ztnfr12 antibody, the ability to specifically bind ZTNF4, and the ability to specifically bind ZTNF4, but not ZTNF2.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of speciation. "Paralogs" are distinct but structurally related proteins made by an organism. Paralogs are believed to arise through gene duplication. For example, α-globin, β-globin, and myoglobin are paralogs of each other.

The present invention includes functional fragments of Ztnfr12 genes. Within the context of this invention, a "functional fragment" of a Ztnfr12 gene refers to a nucleic acid molecule that encodes a portion of a Ztnfr12 polypeptide, which is a domain described herein, or can be characterized by at least one of: the ability to bind specifically to an anti-Ztnfr12 antibody, the ability to specifically bind ZTNF4, and the ability to specifically bind ZTNF4, but not ZTNF2.

Due to the imprecision of standard analytical methods, molecular weights and lengths of polymers are understood to be approximate values. When such a value is expressed as "about" X or "approximately" X, the stated value of X will be understood to be accurate to ±10%.

3. Production of Nucleic Acid Molecules Encoding Ztnfr12

Nucleic acid molecules encoding a human Ztnfr12 gene can be obtained by screening a human cDNA or genomic library using polynucleotide probes based upon SEQ ID NOs:1 or 9. These techniques are standard and well-established.

As an illustration, a nucleic acid molecule that encodes a human Ztnfr12 gene can be isolated from a cDNA library. In this case, the first step would be to prepare the cDNA library by isolating RNA from, for example, germinal center B-cells or lymph node tissue, using methods well-known to those of skill in the art. In general, RNA isolation techniques must provide a method for breaking cells, a means of inhibiting RNase-directed degradation of RNA, and a method of separating RNA from DNA, protein, and polysaccharide contaminants. For example, total RNA can be isolated by freezing tissue in liquid nitrogen, grinding the frozen tissue with a mortar and pestle to lyse the cells, extracting the ground tissue with a solution of phenol/chloroform to remove proteins, and separating RNA from the remaining impurities by selective precipitation with lithium chloride (see, for example, Ausubel et al. (eds.), Short Protocols in Molecular Biology, 3$^{rd}$ Edition, pages 4-1 to 4-6 (John Wiley & Sons 1995) ["Ausubel (1995)"]; Wu et al., Methods in Gene Biotechnology, pages 33-41 (CRC Press, Inc. 1997) ["Wu (1997)"]).

Alternatively, total RNA can be isolated by extracting ground tissue with guanidinium isothiocyanate, extracting with organic solvents, and separating RNA from contaminants using differential centrifugation (see, for example, Chirgwin et al., Biochemistry 18:52 (1979); Ausubel (1995) at pages 4-1 to 4-6; Wu (1997) at pages 33-41).

In order to construct a cDNA library, poly(A)$^+$ RNA must be isolated from a total RNA preparation. Poly(A)$^+$ RNA can be isolated from total RNA using the standard technique of oligo(dT)-cellulose chromatography (see, for example, Aviv and Leder, Proc. Nat'l Acad. Sci. USA 69:1408 (1972); Ausubel (1995) at pages 4-11 to 4-12).

Double-stranded cDNA molecules are synthesized from poly(A)$^+$ RNA using techniques well-known to those in the art. (see, for example, Wu (1997) at pages 41-46). Moreover, commercially available kits can be used to synthesize double-stranded cDNA molecules. For example, such kits are available from Life Technologies, Inc. (Gaithersburg, Md.), CLONTECH Laboratories, Inc. (Palo Alto, Calif.), Promega Corporation (Madison, Wis.) and STRATAGENE (La Jolla, Calif.).

Various cloning vectors are appropriate for the construction of a cDNA library. For example, a cDNA library can be prepared in a vector derived from bacteriophage, such as a λgt10 vector. See, for example, Huynh et al., "Constructing and Screening cDNA Libraries in λgt10 and λgt11," in DNA Cloning: A Practical Approach Vol. I, Glover (ed.), page 49 (IRL Press, 1985); Wu (1997) at pages 47-52.

Alternatively, double-stranded cDNA molecules can be inserted into a plasmid vector, such as a PBLUESCRIPT vector (STRATAGENE; La Jolla, Calif.), a LAMDAGEM-4 (Promega Corp.) or other commercially available vectors. Suitable cloning vectors also can be obtained from the American Type Culture Collection (Manassas, Va.).

To amplify the cloned cDNA molecules, the cDNA library is inserted into a prokaryotic host, using standard techniques. For example, a cDNA library can be introduced into competent E. coli DH5 cells, which can be obtained, for example, from Life Technologies, Inc. (Gaithersburg, Md.).

A human genomic library can be prepared by means well-known in the art (see, for example, Ausubel (1995) at pages 5-1 to 5-6; Wu (1997) at pages 307-327). Genomic DNA can be isolated by lysing tissue with the detergent Sarkosyl, digesting the lysate with proteinase K, clearing insoluble debris from the lysate by centrifugation, precipitating nucleic acid from the lysate using isopropanol, and purifying resuspended DNA on a cesium chloride density gradient.

DNA fragments that are suitable for the production of a genomic library can be obtained by the random shearing of genomic DNA or by the partial digestion of genomic DNA with restriction endonucleases. Genomic DNA fragments can be inserted into a vector, such as a bacteriophage or cosmid vector, in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are well-known in the art (see, for example, Ausubel (1995) at pages 5-1 to 5-6; Wu (1997) at pages 307-327).

Alternatively, human genomic libraries can be obtained from commercial sources such as ResGen (Huntsville, Ala.) and the American Type Culture Collection (Manassas, Va.).

A library containing cDNA or genomic clones can be screened with one or more polynucleotide probes based upon SEQ ID NO:1, using standard methods (see, for example, Ausubel (1995) at pages 6-1 to 6-11).

Nucleic acid molecules that encode a human Ztnfr12 gene can also be obtained using the polymerase chain reaction (PCR) with oligonucleotide primers having nucleotide sequences that are based upon the nucleotide sequences of the Ztnfr12 gene, as described herein. General methods for screening libraries with PCR are provided by, for example, Yu et al., "Use of the Polymerase Chain Reaction to Screen Phage Libraries," in Methods in Molecular Biology, Vol. 15: PCR Protocols: Current Methods and Applications, White (ed.), pages 211-215 (Humana Press, Inc. 1993). Moreover, techniques for using PCR to isolate related genes are described by, for example, Preston, "Use of Degenerate Oligonucleotide Primers and the Polymerase Chain Reaction to Clone Gene Family Members," in Methods in Molecular Biology, Vol. 15: PCR Protocols: Current Methods and Applications, White (ed.), pages 317-337 (Humana Press, Inc. 1993).

Anti-Ztnfr12 antibodies, produced as described below, can also be used to isolate DNA sequences that encode human Ztnfr12 genes from cDNA libraries. For example, the antibodies can be used to screen λgt11 expression libraries, or the antibodies can be used for immunoscreening following hybrid selection and translation (see, for example, Ausubel (1995) at pages 6-12 to 6-16; Margolis et al., "Screening λ expression libraries with antibody and protein probes," in DNA Cloning 2: Expression Systems, 2nd Edition, Glover et al. (eds.), pages 1-14 (Oxford University Press 1995)).

As an alternative, a Ztnfr12 gene can be obtained by synthesizing nucleic acid molecules using mutually priming long oligonucleotides and the nucleotide sequences described herein (see, for example, Ausubel (1995) at pages 8-8 to 8-9). Established techniques using the polymerase chain reaction provide the ability to synthesize DNA molecules at least two kilobases in length (Adang et al., Plant Molec. Biol. 21:1131 (1993), Bambot et al., PCR Methods and Applications 2:266 (1993), Dillon et al., "Use of the Polymerase Chain Reaction for the Rapid Construction of Synthetic Genes," in Methods in Molecular Biology, Vol. 15: PCR Protocols: Current Methods and Applications, White (ed.), pages 263-268, (Humana Press, Inc. 1993), and Holowachuk et al., PCR Methods Appl. 4:299 (1995)).

The nucleic acid molecules of the present invention can also be synthesized with "gene machines" using protocols such as the phosphoramidite method. If chemically-synthesized double stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes (>300 base pairs), however, special strategies may be required, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. For reviews on polynucleotide synthesis, see, for example, Glick and Pasternak, Molecular Biotechnology, Principles and Applications of Recombinant DNA (ASM Press 1994), Itakura et al., Annu. Rev. Biochem. 53:323 (1984), and Climie et al., Proc. Nat'l Acad. Sci. USA 87:633 (1990).

The sequence of a Ztnfr12 cDNA or Ztnfr12 genomic fragment can be determined using standard methods. Ztnfr12 polynucleotide sequences disclosed herein can also be used as probes or primers to clone 5' non-coding regions of a Ztnfr12 gene. Promoter elements from a Ztnfr12 gene can be used to direct the expression of heterologous genes in lymph node tissue, for example, transgenic animals or patients treated with gene therapy. Such a promoter element can be provided by a fragment consisting of 50, 100, 200, 400, or 600 nucleotides of nucleotides 1 to 1000 of SEQ ID NO:9. Alternatively, a Ztnfr12 gene promoter may be provided by nucleotides 1 to 1000 of SEQ ID NO:9. The identification of genomic fragments containing a Ztnfr12 promoter or regulatory element can be achieved using well-established techniques, such as deletion analysis (see, generally, Ausubel (1995)).

Cloning of 5' flanking sequences also facilitates production of Ztnfr12 proteins by "gene activation," as disclosed in U.S. Pat. No. 5,641,670. Briefly, expression of an endogenous Ztnfr12 gene in a cell is altered by introducing into the Ztnfr12 locus a DNA construct comprising at least a targeting sequence, a regulatory sequence, an exon, and an unpaired splice donor site. The targeting sequence is a Ztnfr12 5' non-coding sequence that permits homologous recombination of the construct with the endogenous Ztnfr12 locus, whereby the sequences within the construct become operably linked with the endogenous Ztnfr12 coding sequence. In this way, an endogenous Ztnfr12 promoter can be replaced or supplemented with other regulatory sequences to provide enhanced, tissue-specific, or otherwise regulated expression.

4. Production of Ztnfr12 Variants

The present invention provides a variety of nucleic acid molecules, including DNA and RNA molecules, which encode the Ztnfr12 polypeptides disclosed herein. Those skilled in the art will readily recognize that, in view of the degeneracy of the genetic code, considerable sequence variation is possible among these polynucleotide molecules. SEQ ID NO:3 is a degenerate nucleotide sequence that encompasses all nucleic acid molecules that encode the Ztnfr12 polypeptide of SEQ ID NO:2. Those skilled in the art will recognize that the degenerate sequence of SEQ ID NO:3 also provides all RNA sequences encoding SEQ ID NO:2, by substituting U for T. Thus, the present invention contemplates Ztnfr12 polypeptide-encoding nucleic acid molecules comprising nucleotide 27 to nucleotide 578 of SEQ ID NO:1, and their RNA equivalents.

Table 2 sets forth the one-letter codes used within SEQ ID NO:3 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 2

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:3, encompassing all possible codons for a given amino acid, are set forth in Table 3.

TABLE 3

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | * | TAA TAG TGA | TRR |
| Asn\|Asp | B |  | RAY |
| Glu\|Gln | Z |  | SAR |
| Any | X |  | NNN |

One of ordinary skill in the art will appreciate that some ambiguity is introduced in determining a degenerate codon, representative of all possible codons encoding an amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences of SEQ ID NO:2. Variant sequences can be readily tested for functionality as described herein.

Different species can exhibit "preferential codon usage." In general, see, Grantham et al., Nucl. Acids Res. 8:1893 (1980), Haas et al. Curr. Biol. 6:315 (1996), Wain-Hobson et al., Gene 13:355 (1981), Grosjean and Fiers, Gene 18:199 (1982), Holm, Nuc. Acids Res. 14:3075 (1986), Ikemura, J. Mol. Biol. 158:573 (1982), Sharp and Matassi, Curr. Opin. Genet. Dev. 4:851 (1994), Kane, Curr. Opin. Biotechnol. 6:494 (1995), and Makrides, Microbiol. Rev. 60:512 (1996). As used herein, the term "preferential codon usage" or "preferential codons" is a term of art referring to protein translation codons that are most frequently used in cells of a certain species, thus favoring one or a few representatives of the possible codons encoding each amino acid (See Table 3). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed herein serve as a template for optimizing expression of polynucleotides in various cell types and species commonly used in the art and disclosed herein. Sequences containing preferential codons can be tested and optimized for expression in various species, and tested for functionality as disclosed herein.

The present invention further provides variant polypeptides and nucleic acid molecules that represent counterparts from other species (orthologs). These species include, but are not limited to mammalian, avian, amphibian, reptile, fish, insect and other vertebrate and invertebrate species. As an illustration, SEQ ID NO:12, SEQ ID NO:13, and SEQ ID NO:14 provide the nucleotide, amino acid, and degenerate nucleotide sequences, respectively, of murine Ztnfr12. Features of the murine Ztnfr12 polypeptide include an extracellular domain at amino acid residues 1 to 69 of SEQ ID NO:13, a transmembrane domain at amino acid residues 70 to 96 of SEQ ID NO:13, an intracellular domain at amino acid residues 97 to 175 of SEQ ID NO:13, and a cys-rich region at amino acid residues 21 to 138 of SEQ ID NO:13.

Of particular interest are Ztnfr12 polypeptides from other mammalian species, including mouse, porcine, ovine, bovine, canine, feline, equine, and other primate polypeptides. Orthologs of human Ztnfr12 can be cloned using information and compositions provided by the present invention in combination with conventional cloning techniques. For example, a Ztnfr12 cDNA can be cloned using mRNA obtained from a tissue or cell type that expresses Ztnfr12 as disclosed herein. Suitable sources of mRNA can be identified by probing northern blots with probes designed from the sequences disclosed herein. A library is then prepared from mRNA of a positive tissue or cell line.

A Ztnfr12-encoding cDNA can be isolated by a variety of methods, such as by probing with a complete or partial human cDNA or with one or more sets of degenerate probes based on the disclosed sequences. A cDNA can also be cloned using the polymerase chain reaction with primers designed from the representative human Ztnfr12 sequences disclosed herein. In addition, a cDNA library can be used to transform or transfect host cells, and expression of the cDNA of interest can be detected with an antibody to Ztnfr12 polypeptide.

Those skilled in the art will recognize that the sequence disclosed in SEQ ID NO:1 represents a single allele of human Ztnfr12, and that allelic variation and alternative splicing are expected to occur. Allelic variants of this sequence can be cloned by probing cDNA or genomic libraries from different individuals according to standard procedures. Allelic variants of the nucleotide sequences disclosed herein, including those containing silent mutations and those in which mutations result in amino acid sequence changes, are within the scope of the present invention, as are proteins which are allelic variants of the amino acid sequences disclosed herein. cDNA molecules generated from alternatively spliced mRNAs, which retain the properties of the Ztnfr12 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Within certain embodiments of the invention, the isolated nucleic acid molecules can hybridize under stringent conditions to nucleic acid molecules comprising nucleotide sequences disclosed herein. For example, such nucleic acid molecules can hybridize under stringent conditions to nucleic acid molecules comprising the nucleotide sequence of SEQ ID NO:1, to nucleic acid molecules consisting of the nucleotide sequence of nucleotides 27 to 578 of SEQ ID NO:1, or to nucleic acid molecules comprising a nucleotide sequence complementary to SEQ ID NO:1, or nucleotides 27 to 578 of SEQ ID NO:1. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The $T_m$ of the mismatched hybrid decreases by 1° C. for every 1-1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases. Stringent hybridization conditions encompass temperatures of about 5-25° C. below the $T_m$ of the hybrid and a hybridization buffer having up to 1 M Na⁺. Higher degrees of stringency at lower temperatures can be achieved with the addition of formamide which reduces the $T_m$ of the hybrid about 1° C. for each 1% formamide in the buffer solution. Generally, such stringent conditions include temperatures of 20-70° C. and a hybridization buffer containing up to 6×SSC and 0-50% formamide. A higher degree of stringency can be achieved at temperatures of from 40-70° C. with a hybridization buffer having up to 4×SSC and from 0-50% formamide. Highly stringent conditions typically encompass temperatures of 42-70° C. with a hybridization buffer having up to 1×SSC and 0-50% formamide. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes.

The above conditions are meant to serve as a guide and it is well within the abilities of one skilled in the art to adapt these conditions for use with a particular polypeptide hybrid. The $T_m$ for a specific target sequence is the temperature (under defined conditions) at which 50% of the target sequence will hybridize to a perfectly matched probe sequence. Conditions that influence the $T_m$ include, the size and base pair content of the polynucleotide probe, the ionic strength of the hybridization solution, and the presence of destabilizing agents in the hybridization solution. Numerous equations for calculating $T_m$ are known in the art, and are specific for DNA, RNA and DNA-RNA hybrids and polynucleotide probe sequences of varying length (see, for example, Sambrook et al., Molecular Cloning: A Laboratory Manual, Second Edition (Cold Spring Harbor Press 1989); Ausubel et al., (eds.), Current Protocols in Molecular Biology (John Wiley and Sons, Inc. 1987); Berger and Kimmel (eds.), Guide to Molecular Cloning Techniques, (Academic Press, Inc. 1987); and Wetmur, Crit. Rev. Biochem. Mol. Biol. 26:227 (1990)). Sequence analysis software such as OLIGO 6.0 (LSR; Long Lake, Minn.) and Primer Premier 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20-25° C. below the calculated $T_m$. For smaller probes, <50 base pairs, hybridization is typically carried out at the $T_m$ or 5-10° C. below. This allows for the maximum rate of hybridization for DNA-DNA and DNA-RNA hybrids.

The length of the polynucleotide sequence influences the rate and stability of hybrid formation. Smaller probe sequences, <50 base pairs, reach equilibrium with complementary sequences rapidly, but may form less stable hybrids. Incubation times of anywhere from minutes to hours can be used to achieve hybrid formation. Longer probe sequences come to equilibrium more slowly, but form more stable complexes even at lower temperatures. Incubations are allowed to proceed overnight or longer. Generally, incubations are carried out for a period equal to three times the calculated Cot time. Cot time, the time it takes for the polynucleotide sequences to reassociate, can be calculated for a particular sequence by methods known in the art.

The base pair composition of polynucleotide sequence will effect the thermal stability of the hybrid complex, thereby influencing the choice of hybridization temperature and the ionic strength of the hybridization buffer. A-T pairs are less stable than G-C pairs in aqueous solutions containing sodium chloride. Therefore, the higher the G-C content, the more stable the hybrid. Even distribution of G and C residues within the sequence also contribute positively to hybrid stability. In addition, the base pair composition can be manipulated to alter the $T_m$ of a given sequence. For example, 5-methyldeoxycytidine can be substituted for deoxycytidine and 5-bromodeoxuridine can be substituted for thymidine to increase the $T_m$, whereas 7-deazz-2'-deoxyguanosine can be substituted for guanosine to reduce dependence on $T_m$.

The ionic concentration of the hybridization buffer also affects the stability of the hybrid. Hybridization buffers generally contain blocking agents such as Denhardt's solution (Sigma Chemical Co., St. Louis, Mo.), denatured salmon sperm DNA, tRNA, milk powders (BLOTTO), heparin or SDS, and a Na⁺ source, such as SSC (1×SSC: 0.15 M sodium chloride, 15 mM sodium citrate) or SSPE (1×SSPE: 1.8 M NaCl, 10 mM NaH₂PO₄, 1 mM EDTA, pH 7.7). Typically, hybridization buffers contain from between 10 mM-1 M Na⁺. The addition of destabilizing or denaturing agents such as formamide, tetralkylammonium salts, guanidinium cations or thiocyanate cations to the hybridization solution will alter the $T_m$ of a hybrid. Typically, formamide is used at a concentration of up to 50% to allow incubations to be carried out at more convenient and lower temperatures. Formamide also acts to reduce non-specific background when using RNA probes.

As an illustration, a nucleic acid molecule encoding a variant Ztnfr12 polypeptide can be hybridized with a nucleic acid molecule having the nucleotide sequence of SEQ ID NO:1 (or its complement) at 42° C. overnight in a solution comprising 50% formamide, 5×SSC, 50 mM sodium phosphate (pH 7.6), 5×Denhardt's solution (100×Denhardt's solution: 2% (w/v) Ficoll 400, 2% (w/v) polyvinylpyrrolidone, and 2% (w/v) bovine serum albumin), 10% dextran sulfate, and 20 µg/ml denatured, sheared salmon sperm DNA. One of skill in the art can devise variations of these hybridization conditions. For example, the hybridization mixture can be incubated at a higher temperature, such as about 65° C., in a solution that does not contain formamide. Moreover, premixed hybridization solutions are available (e.g., EXPRESSHYB Hybridization Solution from CLONTECH Laboratories, Inc.), and hybridization can be performed according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×-2×SSC with 0.1% sodium dodecyl sulfate (SDS) at 55–65° C. As an illustration, nucleic acid molecules encoding a variant Ztnfr12 polypeptide remain hybridized with a nucleic acid molecule comprising the nucleotide sequence of nucleotides 27 to 578 of SEQ ID NO:1 (or its complement) following stringent washing conditions, in which the wash stringency is equivalent to 0.5×-2×SSC with 0.1% SDS at 55-65° C., including 0.5×SSC with 0.1% SDS at 55° C., or 2×SSC with 0.1% SDS at 65° C. One of skill in the can readily devise equivalent conditions, for example, by substituting SSPE for SSC in the wash solution.

Typical highly stringent washing conditions include washing in a solution of 0.1×-0.2×SSC with 0.1% sodium dodecyl sulfate (SDS) at 50-65° C. For example, nucleic acid molecules encoding a variant Ztnfr12 polypeptide remain hybridized with a nucleic acid molecule comprising the nucleotide sequence of nucleotides 27 to 578 of SEQ ID NO:1 (or its complement) following highly stringent washing conditions, in which the wash stringency is equivalent to 0.1×-0.2×SSC with 0.1% SDS at 50-65° C., including 0.1×SSC with 0.1% SDS at 50° C., or 0.2×SSC with 0.1% SDS at 65° C.

The present invention also provides isolated Ztnfr12 polypeptides that have a substantially similar sequence identity to the polypeptide of SEQ ID NO:2, or its orthologs. The term "substantially similar sequence identity" is used herein to denote polypeptides having at least 70%, at least 80%, at least 90%, at least 95% or greater than 95% sequence identity to the sequences shown in SEQ ID NO:2, or orthologs.

The present invention also contemplates Ztnfr12 variant nucleic acid molecules that can be identified using two criteria: a determination of the similarity between the encoded polypeptide with the amino acid sequence of SEQ ID NO:2, and a hybridization assay, as described above. Such Ztnfr12 variants include nucleic acid molecules (1) that remain hybridized with a nucleic acid molecule comprising the nucleotide sequence of nucleotides 27 to 578 of SEQ ID NO:1 (or its complement) following stringent washing conditions, in which the wash stringency is equivalent to 0.5×-2×SSC with 0.1% SDS at 55-65° C., and (2) that encode a polypeptide having at least 70% at least 80%, at least 90%, at least 95% or greater than 95% sequence identity to the amino acid sequence of SEQ ID NO:2. Alternatively, Ztnfr12 variants can be characterized as nucleic acid molecules (1) that remain hybridized with a nucleic acid molecule comprising the nucleotide sequence of nucleotides 27 to 578 of SEQ ID NO:1 (or its complement) following highly stringent washing conditions, in which the wash stringency is equivalent to 0.1×-0.2×SSC with 0.1% SDS at 50-65° C., and (2) that encode a polypeptide having at least 70%, at least 80%, at least 90%, at least 95or greater than 95% sequence identity to the amino acid sequence of SEQ ID NO:2.

Percent sequence identity is determined by conventional methods. See, for example, Altschul et al., Bull. Math. Bio. 48:603 (1986), and Henikoff and Henikoff, Proc. Natl. Acad. Sci. USA 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 4 (amino acids are indicated by the standard one-letter codes). The percent identity is then calculated as: ([Total number of identical matches]/[length of the longer sequence plus the number of gaps introduced into the longer sequence in order to align the two sequences])(100).

TABLE 4

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative Ztnfr12 variant. The FASTA algorithm is described by Pearson and Lipman, Proc. Nat'l Acad. Sci. USA 85:2444 (1988), and by Pearson, Meth. Enzymol. 183:63 (1990). Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, SIAM J. Appl. Math. 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as described above.

The present invention includes nucleic acid molecules that encode a polypeptide having a conservative amino acid change, compared with an amino acid sequence disclosed herein. For example, variants can be obtained that contain one or more amino acid substitutions of SEQ ID NO:2, in which an alkyl amino acid is substituted for an alkyl amino acid in a Ztnfr12 amino acid sequence, an aromatic amino acid is substituted for an aromatic amino acid in a Ztnfr12 amino acid sequence, a sulfur-containing amino acid is substituted for a sulfur-containing amino acid in a Ztnfr12 amino acid sequence, a hydroxy-containing amino acid is substituted for a hydroxy-containing amino acid in a Ztnfr12 amino acid sequence, an acidic amino acid is substituted for an acidic amino acid in a Ztnfr12 amino acid sequence, a basic amino acid is substituted for a basic amino acid in a Ztnfr12 amino acid sequence, or a dibasic monocarboxylic amino acid is substituted for a dibasic monocarboxylic amino acid in a Ztnfr12 amino acid sequence. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

The BLOSUM62 table is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Certain conservative amino acid substitutions can be identified by aligning human and murine Ztnfr12 amino acid sequences. For example, an alignment indicates the following amino acid substitutions in the human Ztnfr12 amino acid sequence of SEQ ID NO:2: Ala$^{15}$ to Val$^{15}$, Arg$^{39}$ to His$^{39}$, and Ala$^{71}$ to Leu$^{71}$. Such an alignment identifies other conservative amino acid substitutions of the human Ztnfr12 amino acid sequence, or conservative amino acid substitutions of the murine Ztnfr12 amino acid sequence.

Particular variants of Ztnfr12 are characterized by having at least 70%, at least 80%, at least 90%, at least 95% or greater than 95% sequence identity to the corresponding amino acid sequence (e.g., SEQ ID NO:2), wherein the variation in amino acid sequence is due to one or more conservative amino acid substitutions.

Conservative amino acid changes in a Ztnfr12 gene can be introduced, for example, by substituting nucleotides for the nucleotides recited in SEQ ID NO:1. Such "conservative amino acid" variants can be obtained by oligonucleotide-directed mutagenesis, linker-scanning mutagenesis, mutagenesis using the polymerase chain reaction, and the like (see Ausubel (1995) at pages 8-10 to 8-22; and McPherson (ed.), Directed Mutagenesis: A Practical Approach (IRL Press 1991)). A variant Ztnfr12 polypeptide can be identified by the ability to specifically bind anti-Ztnfr12 antibodies.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an E. coli S30 extract and commercially available enzymes and other reagents. Proteins are purified by chromatography. See, for example, Robertson et al., J. Am. Chem. Soc. 113:2722 (1991), Ellman et al., Methods Enzymol. 202:301 (1991), Chung et al., Science 259:806 (1993), and Chung et al., Proc. Nat'l Acad. Sci. USA 90:10145 (1993).

In a second method, translation is carried out in Xenopus oocytes by microinjection of mutated mRNA and chemically aminoacylated suppressor tRNAs (Turcatti et al., J. Biol.

Chem. 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., Biochem. 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395 (1993)).

A limited number of non-conservative amino acids, amino acids that are not encoded by the genetic code, non-naturally occurring amino acids, and unnatural amino acids may be substituted for Ztnfr12 amino acid residues.

Essential amino acids in the polypeptides of the present invention can be identified according to procedures known in the art, such as site-directed mutagenesis or alanine-scanning mutagenesis (Cunningham and Wells, Science 244:1081 (1989), Bass et al., Proc. Nat'l Acad. Sci. USA 88:4498 (1991), Coombs and Corey, "Site-Directed Mutagenesis and Protein Engineering," in Proteins: Analysis and Design, Angeletti (ed.), pages 259-311 (Academic Press, Inc. 1998)). In the latter technique, single alanine mutations are introduced at every residue in the molecule, and the resultant mutant molecules are tested for biological activity to identify amino acid residues that are critical to the activity of the molecule. See also, Hilton et al., J. Biol. Chem. 271:4699 (1996).

Although sequence analysis can be used to further define the Ztnfr12 ligand binding region, amino acids that play a role in Ztnfr12 binding activity can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306 (1992), Smith et al, J. Mol. Biol. 224:899 (1992), and Wlodaver et al., FEBS Leff. 309:59 (1992).

Multiple amino acid substitutions can be made and tested using known methods of mutagenesis and screening, such as those disclosed by Reidhaar-Olson and Sauer (Science 241: 53 (1988)) or Bowie and Sauer (Proc. Nat'l Acad. Sci. USA 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832 (1991), Ladner et al., U.S. Pat. No. 5,223,409, Huse, international publication No. WO 92/06204, and region-directed mutagenesis (Derbyshire et al., Gene 46:145 (1986), and Ner et al., DNA 7:127, (1988)). Moreover, Ztnfr12 labeled with biotin or FITC can be used for expression cloning of new Ztnfr12 ligands.

Variants of the disclosed Ztnfr12 nucleotide and polypeptide sequences can also be generated through DNA shuffling as disclosed by Stemmer, Nature 370:389 (1994), Stemmer, Proc. Nat'l Acad. Sci. USA 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-Ztnfr12 antibodies, can be recovered from the host cells and rapidly sequenced using modern equipment. These methods allow the rapid determination of the importance of individual amino acid residues in a polypeptide of interest, and can be applied to polypeptides of unknown structure.

The present invention also includes "functional fragments" of Ztnfr12 polypeptides and nucleic acid molecules encoding such functional fragments. Routine deletion analyses of nucleic acid molecules can be performed to obtain functional fragments of a nucleic acid molecule that encodes a Ztnfr12 polypeptide. As an illustration, DNA molecules comprising the nucleotide sequence of nucleotides 27 to 578 of SEQ ID NO:1 can be digested with Bal31 nuclease to obtain a series of nested deletions. The fragments are then inserted into expression vectors in proper reading frame, and the expressed polypeptides are isolated and tested for the ability to bind anti-Ztnfr12 antibodies. One alternative to exonuclease digestion is to use oligonucleotide-directed mutagenesis to introduce deletions or stop codons to specify production of a desired fragment. Alternatively, particular fragments of a Ztnfr12 gene can be synthesized using the polymerase chain reaction. An example of a functional fragment is the extracellular domain of Ztnfr12 (i.e., about amino acid residues 1 to 69 of SEQ ID NO:2, or about amino acid residues 1 to 79 of SEQ ID NO:2).

This general approach is exemplified by studies on the truncation at either or both termini of interferons have been summarized by Horisberger and Di Marco, Pharmac. Ther. 66:507 (1995). Moreover, standard techniques for functional analysis of proteins are described by, for example, Treuter et al., Molec. Gen. Genet. 240:113 (1993), Content et al., "Expression and preliminary deletion analysis of the 42 kDa 2-5A synthetase induced by human interferon," in Biological Interferon Systems, Proceedings of ISIR-TNO Meeting on Interferon Systems, Cantell (ed.), pages 65-72 (Nijhoff 1987), Herschman, "The EGF Receptor," in Control of Animal Cell Proliferation, Vol. 1, Boynton et al., (eds.) pages 169-199 (Academic Press 1985), Coumailleau et al., J. Biol. Chem. 270:29270 (1995); Fukunaga et al., J. Biol. Chem. 270:25291 (1995); Yamaguchi et al., Biochem. Pharmacol. 50:1295 (1995), and Meisel et al., Plant Molec. Biol. 30:1 (1996).

The present invention also contemplates functional fragments of a Ztnfr12 gene that have amino acid changes, compared with an amino acid sequence disclosed herein. A variant Ztnfr12 gene can be identified on the basis of structure by determining the level of identity with disclosed nucleotide and amino acid sequences, as discussed above. An alternative approach to identifying a variant gene on the basis of structure is to determine whether a nucleic acid molecule encoding a potential variant Ztnfr12 gene can hybridize to a nucleic acid molecule comprising a nucleotide sequence, such as SEQ ID NO:1.

The present invention also provides polypeptide fragments or peptides comprising an epitope-bearing portion of a Ztnfr12 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., Proc. Nat'l Acad. Sci. USA 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., Science 219:660 (1983)). Accordingly, antigenic epitope-bearing peptides and polypeptides of the present invention are useful to raise antibodies that bind with the polypeptides described herein.

Antigenic epitope-bearing peptides and polypeptides can contain at least four to ten amino acids, at least ten to fifteen amino acids, or about 15 to about 30 amino acids of an amino acid sequence disclosed herein. Such epitope-bearing peptides and polypeptides can be produced by fragmenting a Ztnfr12 polypeptide, or by chemical peptide synthesis, as described herein. Moreover, epitopes can be selected by phage display of random peptide libraries (see, for example, Lane and Stephen, Curr. Opin. Immunol. 5:268 (1993), and Cortese et al., Curr. Opin. Biotechnol. 7:616 (1996)). Standard methods for identifying epitopes and producing antibodies from small peptides that comprise an epitope are described, for example, by Mole, "Epitope Mapping," in Methods in Molecular Biology, Vol. 10, Manson (ed.), pages 105-116 (The Humana Press, Inc. 1992), Price, "Production and Characterization of Synthetic Peptide-Derived Antibodies," in Monoclonal Antibodies: Production, Engineering, and Clinical Application, Riffer and Ladyman (eds.), pages 60-84 (Cambridge University Press 1995), and Coligan et al. (eds.), Current Protocols in Immunology, pages 9.3.1-9.3.5 and pages 9.4.1-9.4.11 (John Wiley & Sons 1997).

In addition to the uses described above, polynucleotides and polypeptides of the present invention are useful as educational tools in laboratory practicum kits for courses related to genetics and molecular biology, protein chemistry, and antibody production and analysis. Due to its unique polynucleotide and polypeptide sequences, molecules of Ztnfr12 can be used as standards or as "unknowns" for testing purposes. For example, Ztnfr12 polynucleotides can be used as an aid, such as, for example, to teach a student how to prepare expression constructs for bacterial, viral, or mammalian expression, including fusion constructs, wherein Ztnfr12 is the gene to be expressed; for determining the restriction endonuclease cleavage sites of the polynucleotides; determining mRNA and DNA localization of Ztnfr12 polynucleotides in tissues (i.e., by northern and Southern blotting as well as polymerase chain reaction); and for identifying related polynucleotides and polypeptides by nucleic acid hybridization. As an illustration, students will find that PstI digestion of a nucleic acid molecule consisting of the nucleotide sequence of nucleotides 27 to 578 of SEQ ID NO:1 provides two fragments of about 174 base pairs, and 378 base pairs, and that HinfI digestion yields fragments of about 182 base pairs, 226 base pairs, and 144 base pairs.

Ztnfr12 polypeptides can be used as an aid to teach preparation of antibodies; identifying proteins by western blotting; protein purification; determining the weight of expressed Ztnfr12 polypeptides as a ratio to total protein expressed; identifying peptide cleavage sites; coupling amino and carboxyl terminal tags; amino acid sequence analysis, as well as, but not limited to monitoring biological activities of both the native and tagged protein (i.e., protease inhibition) in vitro and in vivo. For example, students will find that digestion of unglycosylated Ztnfr12 with endopeptidase Lys C yields five fragments having approximate molecular weights of 4870, 7691, 883, 4758, and 729, whereas digestion of unglycosylated Ztnfr12 with BNPS or NCS/urea yields fragments having approximate molecular weights of 10279, 4740, and 3877.

Ztnfr12 polypeptides can also be used to teach analytical skills such as mass spectrometry, circular dichroism, to determine conformation, especially of the four alpha helices, x-ray crystallography to determine the three-dimensional structure in atomic detail, nuclear magnetic resonance spectroscopy to reveal the structure of proteins in solution. For example, a kit containing the Ztnfr12 can be given to the student to analyze. Since the amino acid sequence would be known by the instructor, the protein can be given to the student as a test to determine the skills or develop the skills of the student, the instructor would then know whether or not the student has correctly analyzed the polypeptide. Since every polypeptide is unique, the educational utility of Ztnfr12 would be unique unto itself.

The antibodies which bind specifically to Ztnfr12 can be used as a teaching aid to instruct students how to prepare affinity chromatography columns to purify Ztnfr12, cloning and sequencing the polynucleotide that encodes an antibody and thus as a practicum for teaching a student how to design humanized antibodies. The Ztnfr12 gene, polypeptide, or antibody would then be packaged by reagent companies and sold to educational institutions so that the students gain skill in art of molecular biology. Because each gene and protein is unique, each gene and protein creates unique challenges and learning experiences for students in a lab practicum. Such educational kits containing the Ztnfr12 gene, polypeptide, or antibody are considered within the scope of the present invention.

For any Ztnfr12 polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise Ztnfr12 variants based upon the nucleotide and amino acid sequences described herein. Accordingly, the present invention includes a computer-readable medium encoded with a data structure that provides at least one of the following sequences: SEQ ID NO:1, SEQ ID NO:2, and SEQ ID NO:3. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

5. Production of Ztnfr12 Polypeptides

The polypeptides of the present invention, including full-length polypeptides, functional fragments, and fusion proteins, can be produced in recombinant host cells following conventional techniques. To express a Ztnfr12 gene, a nucleic acid molecule encoding the polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. As discussed above, expression vectors can also include nucleotide sequences encoding a secretory sequence that directs the heterologous polypeptide into the secretory pathway of a host cell. For example, a Ztnfr12 expression vector may comprise a Ztnfr12 gene and a secretory sequence derived from any secreted gene.

Expression of Ztnfr12 can be achieved using nucleic acid molecules that either include or do not include noncoding portions of the Ztnfr12 gene. However, higher efficiency of production from certain recombinant host cells may be obtained when at least one Ztnfr12 intron sequence is included in the expression vector.

Ztnfr12 proteins of the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 (Chasin et al., Som. Cell. Molec. Genet. 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and-murine embryonic cells (NIH-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., J. Molec. Appl. Genet. 1:273 (1982)), the TK promoter of Herpes virus (McKnight, Cell 31:355 (1982)), the SV40 early promoter (Benoist et al., Nature 290:304 (1981)), the Rous sarcoma virus promoter (Gorman et al., Proc. Nat'l Acad. Sci. USA 79:6777 (1982)), the cytomegalovirus promoter (Foecking et al., Gene 45:101 (1980)), and the mouse mammary tumor virus promoter (see, generally, Etcheverry, "Expression of Engineered Proteins in Mammalian Cell Culture," in Protein Engineering: Principles and Practice, Cleland et al. (eds.), pages 163-181 (John Wiley & Sons, Inc. 1996)).

Alternatively, a prokaryotic promoter, such as the bacteriophage T3 RNA polymerase promoter, can be used to control Ztnfr12 gene expression in mammalian cells if the prokaryotic promoter is regulated by a eukaryotic promoter (Zhou et al., Mol. Cell. Biol. 10:4529 (1990), and Kaufman et al., Nucl. Acids Res. 19:4485 (1991)).

An expression vector can be introduced into host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), Gene Transfer and Expression Protocols (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A suitable amplifiable selectable marker is dihydrofolate reductase, which confers resistance to methotrexate. Other drug resistance genes (e.g., hygromycin resistance, multi-drug resistance, puromycin acetyltransferase) can also be used. Alternatively, markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Ztnfr12 polypeptides can also be produced by cultured mammalian cells using a viral delivery system. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see Becker et al., Meth. Cell Biol. 43:161 (1994), and Douglas and Curiel, Science & Medicine 4:44 (1997)). Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. Adenovirus vector-infected human 293 cells (ATCC Nos. CRL-1573, 45504, 45505), for example, can be grown as adherent cells or in suspension culture at relatively high cell density to produce significant amounts of protein (see Garnier et al., Cytotechnol. 15:145 (1994)).

Ztnfr12 can also be expressed in other higher eukaryotic cells, such as avian, fungal, insect, yeast, or plant cells. The baculovirus system provides an efficient means to introduce cloned Ztnfr12 genes into insect cells. Suitable expression vectors are based upon the *Autographa californica* multiple nuclear polyhedrosis virus (AcMNPV), and contain well-known promoters such as *Drosophila* heat shock protein (hsp) 70 promoter, *Autographa califomica* nuclear polyhedrosis virus immediate-early gene promoter (ie-1) and the delayed early 39K promoter, baculovirus p10 promoter, and the *Drosophila* metallothionein promoter. A second method of making recombinant baculovirus utilizes a transposon-based system described by Luckow (Luckow, et al., J. Virol. 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the Ztnfr12 polypeptide into a baculovirus genome maintained in *E. coli* as a large plasmid called a "bacmid." See, Hill-Perkins and Possee, J. Gen. Virol. 71:971 (1990), Bonning, et al., J. Gen. Virol. 75:1551 (1994), and Chazenbalk, and Rapoport, J. Biol. Chem. 270:1543 (1995). In addition, transfer vectors can include an in-frame fusion with DNA encoding an epitope tag at the C- or N-terminus of the expressed Ztnfr12 polypeptide, for example, a Glu-Glu epitope tag (Grussenmeyer et al., Proc. Nat'l Acad. Sci. 82:7952 (1985)). Using a technique known in the art, a transfer vector containing a Ztnfr12 gene is transformed into *E. coli*, and screened for bacmids, which contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins (see, for example, Hill-Perkins and Possee, J. Gen. Virol. 71:971 (1990), Bonning, et al., J. Gen. Virol. 75:1551 (1994), and Chazenbalk and Rapoport, J. Biol. Chem. 270: 1543 (1995). In such transfer vector constructs, a short or long version of the basic protein promoter can be used. Moreover, transfer vectors can be constructed, which replace the native Ztnfr12 secretory signal sequences with secretory signal sequences derived from insect proteins. For example, a secretory signal sequence from Ecdysteroid Glucosyltransferase (EGT), honey bee Melittin (Invitrogen Corporation; Carlsbad, Calif.), or baculovirus gp67 (PharMingen: San Diego, Calif.) can be used in constructs to replace the native Ztnfr12 secretory signal sequence.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as *Drosophila* Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. When recombinant virus is used, the cells are typically grown up from an inoculation density of approximately 2-5× $10^5$ cells to a density of 1-2×$10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors," in Methods in Molecular Biology, Volume 7: Gene Transfer and Expression Protocols, Murray (ed.), pages 147-168 (The Humana Press, Inc. 1991), by Patel et al., "The baculovirus expression system," in DNA Cloning 2: Expression Systems, 2nd Edition, Glover et al. (eds.), pages 205-244 (Oxford University Press 1995), by Ausubel (1995) at pages 16-37 to 16-57, by Richardson (ed.), Baculovirus Expression Protocols (The Humana Press, Inc. 1995), and by Lucknow, "Insect Cell Expression Technology," in Protein Engineering: Principles and Practice, Cleland et al. (eds.), pages 183-218 (John Wiley & Sons, Inc. 1996).

Fungal cells, including yeast cells, can also be used to express the genes described herein. Yeast species of particular interest in this regard include *Saccharomyces cerevisiae*, *Pichia pastoris*, and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A suitable vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615,974, and Bitter, U.S. Pat. No. 4,977,092) and alcohol dehydrogenase genes. See also U.S. Pat. Nos. 4,990,446, 5,063, 154, 5,139,936, and 4,661,454.

Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., J. Gen. Microbiol. 132:3459 (1986), and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., Yeast 14:11-23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which can be linearized prior to transformation. For polypeptide production in *P. methanolica*, the promoter and terminator in the plasmid can be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, the entire expression segment of the plasmid can be flanked at both ends by host DNA sequences. A suitable selectable marker for use in *Pichia methanolica* is a *P. methanolica* ADE2 gene, which encodes phosphoribosyl-5-aminoimidazole carboxylase (AIRC; EC 4.1.1.21), and which allows ade2 host cells to grow in the absence of adenine. For large-scale, industrial processes where it is desirable to minimize the use of methanol, host cells can be used in which both methanol utilization genes (AUG1 and AUG2) are deleted. For production of secreted proteins, host cells can be deficient in vacuolar protease genes (PEP4 and PRB1). Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens*, microprojectile-mediated delivery, DNA injection, electroporation, and the like. See, for example, Horsch et al., Science 227:1229 (1985), Klein et al., Biotechnology 10:268 (1992), and Miki et al., "Procedures for Introducing Foreign DNA into Plants," in Methods in Plant Molecular Biology and Biotechnology, Glick et al. (eds.), pages 67-88 (CRC Press, 1993).

Alternatively, Ztnfr12 genes can be expressed in prokaryotic host cells. Suitable promoters that can be used to express Ztnfr12 polypeptides in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of *Bacillus, Streptomyces* promoters, the int promoter of bacteriophage lambda, the bla promoter of pBR322, and the CAT promoter of the chloramphenicol acetyl transferase gene. Prokaryotic promoters have been reviewed by Glick, J. Ind. Microbiol. 1:277 (1987), Watson et al., Molecular Biology of the Gene, 4th Ed. (Benjamin Cummins 1987), and by Ausubel et al. (1995).

Suitable prokaryotic hosts include *E. coli* and *Bacillus subtilus*. Suitable strains of *E. coli* include BL21(DE3), BL21(DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), Molecular Biology Labfax (Academic Press 1991)). Suitable strains of *Bacillus subtilus* include BR151, YB886, MI119, MI120, and B170 (see, for example, Hardy, "*Bacillus* Cloning Methods," in DNA Cloning: A Practical Approach, Glover (ed.) (IRL Press 1985)).

When expressing a Ztnfr12 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in DNA Cloning 2: Expression Systems, 2nd Edition, Glover et al. (eds.), page 15 (Oxford University Press 1995), Ward et al., "Genetic Manipulation and Expression of Antibodies," in Monoclonal Antibodies: Principles and Applications, page 137 (Wiley-Liss, Inc. 1995), and Georgiou, "Expression of Proteins in Bacteria," in Protein Engineering: Principles and Practice, Cleland et al. (eds.), page 101 (John Wiley & Sons, Inc. 1996)).

Standard methods for introducing expression vectors into bacterial, yeast, insect, and plant cells are provided, for example, by Ausubel (1995).

General methods for expressing and recovering foreign protein produced by a mammalian cell system are provided by, for example, Etcheverry, "Expression of Engineered Proteins in Mammalian Cell Culture," in Protein Engineering: Principles and Practice, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in DNA Cloning 2: Expression Systems, 2nd Edition, Glover et al. (eds.), pages 59-92 (Oxford University Press 1995). Established methods for isolating recombinant proteins from a baculovirus system are described by Richardson (ed.), Baculovirus Expression Protocols (The Humana Press, Inc. 1995).

As an alternative, polypeptides of the present invention can be synthesized by exclusive solid phase synthesis, partial solid phase methods, fragment condensation or classical solution synthesis. These synthesis methods are well-known to those of skill in the art (see, for example, Merrifield, J. Am. Chem. Soc. 85:2149 (1963), Stewart et al., "Solid Phase Peptide Synthesis" (2nd Edition), (Pierce Chemical Co. 1984), Bayer and Rapp, Chem. Pept. Prot. 3:3 (1986), Atherton et al., Solid Phase Peptide Synthesis: A Practical Approach (IRL Press 1989), Fields and Colowick, "Solid-Phase Peptide Synthesis," Methods in Enzymology Volume 289 (Academic Press 1997), and Lloyd-Williams et al., Chemical Approaches to the Synthesis of Peptides and Proteins (CRC Press, Inc. 1997)). Variations in total chemical synthesis strategies, such as "native chemical ligation" and "expressed protein ligation" are also standard (see, for example, Dawson et al., Science 266:776 (1994), Hackeng et al., Proc. Nat'l Acad. Sci. USA 94:7845 (1997), Dawson, Methods Enzymol. 287: 34 (1997), Muir et al, Proc. Nat'l Acad. Sci. USA 95:6705 (1998), and Severinov and Muir, J. Biol. Chem. 273:16205 (1998)).

Peptides and polypeptides of the present invention comprise at least six, at least nine, or at least 15 contiguous amino acid residues of SEQ ID NO:2. As an illustration, polypeptides can comprise at least six, at least nine, or at least 15 contiguous amino acid residues of amino acid residues 1 to 69 of SEQ ID NO:2, amino acid residues 1 to 79 of SEQ ID NO:2, amino acid residues 7 to 69 of SEQ ID NO:2, or amino acid residues 7 to 79 of SEQ ID NO:2. Within certain embodiments of the invention, the polypeptides comprise 20, 30, 40, 50, 100, or more contiguous residues of these amino acid sequences. For example, polypeptides can comprise at least 30 contiguous amino acid residues of an amino acid sequence selected from the group consisting of: (a) amino acid residues 1 to 184 of SEQ ID NO:2, (b) amino acid residues 1 to 69 of SEQ ID NO:2, (c) amino acid residues 1 to 79 of SEQ ID NO:2, (d) amino acid residues 7 to 69 of SEQ ID NO:2, and (e) amino acid residues 7 to 79 of SEQ ID NO:2. Nucleic acid molecules encoding such peptides and polypeptides are useful as polymerase chain reaction primers and probes, and these peptides and polypeptides are useful to produce antibodies to Ztnfr12.

6. Production of Ztnfr12 Fusion Proteins and Conjugates

One general class of Ztnfr12 analogs are variants having an amino acid sequence that is a mutation of the amino acid sequence disclosed herein. Another general class of Ztnfr12 analogs is provided by anti-idiotype antibodies, and fragments thereof, as described below. Moreover, recombinant antibodies comprising anti-idiotype variable domains can be used as analogs (see, for example, Monfardini et al., Proc. Assoc. Am. Physicians 108:420 (1996)). Since the variable domains of anti-idiotype Ztnfr12 antibodies mimic Ztnfr12, these domains can provide Ztnfr12 binding activity. Methods of producing anti-idiotypic catalytic antibodies are known to those of skill in the art (see, for example, Joron et al., Ann. N Y Acad. Sci. 672:216 (1992), Friboulet et al., Appl. Biochem. Biotechnol. 47:229 (1994), and Avalle et al., Ann. N Y Acad. Sci. 864:118 (1998)).

Another approach to identifying Ztnfr12 analogs is provided by the use of combinatorial libraries. Methods for constructing and screening phage display and other combinatorial libraries are provided, for example, by Kay et al., Phage Display of Peptides and Proteins (Academic Press 1996), Verdine, U.S. Pat. No. 5,783,384, Kay, et. al., U.S. Pat. No. 5,747,334, and Kauffman et al., U.S. Pat. No. 5,723,323.

Ztnfr12 polypeptides have both in vivo and in vitro uses. As an illustration, a soluble form of Ztnfr12 can be added to cell culture medium to inhibit the effects of ZTNF4 either produced by the cultured cells, or added to test medium.

Fusion proteins of Ztnfr12 can be used to express Ztnfr12 in a recombinant host, and to isolate the produced Ztnfr12. As described below, particular Ztnfr12 fusion proteins also have uses in diagnosis and therapy. One type of fusion protein comprises a peptide that guides a Ztnfr12 polypeptide from a recombinant host cell. To direct a Ztnfr12 polypeptide into the secretory pathway of a eukaryotic host cell, a secretory signal sequence (also known as a signal peptide, a leader sequence, prepro sequence or pre sequence) is provided in the Ztnfr12 expression vector. While the secretory signal sequence may be derived from Ztnfr12, a suitable signal sequence may also be derived from another secreted protein or synthesized de novo. The secretory signal sequence is operably linked to a Ztnfr12-encoding sequence such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Although the secretory signal sequence of Ztnfr12 or another protein produced by mammalian cells (e.g., tissue-type plasminogen activator signal sequence, as described, for example, in U.S. Pat. No. 5,641,655) is useful for expression of Ztnfr12 in recombinant mammalian hosts, a yeast signal sequence is preferred for expression in yeast cells. Examples of suitable yeast signal sequences are those derived from yeast mating phermone α-factor (encoded by the MFα1 gene), invertase (encoded by the SUC2 gene), or acid phosphatase (encoded by the PHO5 gene). See, for example, Romanos et al., "Expression of Cloned Genes in Yeast," in DNA Cloning 2: A Practical Approach, $2^{nd}$ Edition, Glover and Hames (eds.), pages 123-167 (Oxford University Press 1995).

In bacterial cells, it is often desirable to express a heterologous protein as a fusion protein to decrease toxicity, increase stability, and to enhance recovery of the expressed protein. For example, Ztnfr12 can be expressed as a fusion protein comprising a glutathione S-transferase polypeptide. Glutathione S-transferease fusion proteins are typically soluble, and easily purifiable from E. coli lysates on immobilized glutathione columns. In similar approaches, a Ztnfr12 fusion protein comprising a maltose binding protein polypeptide can be isolated with an amylose resin column, while a fusion protein comprising the C-terminal end of a truncated Protein A gene can be purified using IgG-Sepharose. Established techniques for expressing a heterologous polypeptide as a fusion protein in a bacterial cell are described, for example, by Williams et al., "Expression of Foreign Proteins in E. coli Using Plasmid Vectors and Purification of Specific Polyclonal Antibodies," in DNA Cloning 2: A Practical Approach, 2d Edition, Glover and Hames (Eds.), pages 15-58 (Oxford University Press 1995). In addition, commercially available expression systems are available. For example, the PIN-POINT Xa protein purification system (Promega Corporation; Madison, Wis.) provides a method for isolating a fusion protein comprising a polypeptide that becomes biotinylated during expression with a resin that comprises avidin.

Peptide tags that are useful for isolating heterologous polypeptides expressed by either prokaryotic or eukaryotic cells include polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., Arch. Biochem. Biophys. 329:215 (1996), Morganti et al., Biotechnol. Appl. Biochem. 23:67 (1996), and Zheng et al., Gene 186:55 (1997). Nucleic acid molecules encoding such peptide tags are available, for example, from Sigma-Aldrich Corporation (St. Louis, Mo.).

Another form of fusion protein comprises a Ztnfr12 polypeptide and an immunoglobulin heavy chain constant region, typically an $F_c$ fragment, which contains two or three constant region domains and a hinge region but lacks the variable region. Fusion proteins comprising a Ztnfr12 moiety and an Fc moiety can be used, for example, as an in vitro assay tool. For example, the presence of a Ztnfr12 ligand in a biological sample can be detected using a Ztnfr12-immunoglobulin fusion protein, in which the Ztnfr12 moiety is used to bind the ligand, and a macromolecule, such as Protein A or anti-Fc antibody, is used to bind the fusion protein to a solid support. Such systems can be used to identify agonists and antagonists that interfere with the binding of a Ztnfr12 ligand to its receptor.

As an illustration, Chang et al., U.S. Pat. No. 5,723,125, describe a fusion protein comprising a human interferon and a human immunoglobulin Fc fragment. The C-terminal of the interferon is linked to the N-terminal of the Fc fragment by a peptide linker moiety. An example of a peptide linker is a peptide comprising primarily a T cell inert sequence, which is immunologically inert. An exemplary peptide linker has the amino acid sequence: GGSGG SGGGG SGGGG S (SEQ ID NO:4). In this fusion protein, an illustrative Fc moiety is a human γ4 chain, which is stable in solution and has little or no complement activating activity. Accordingly, the present invention contemplates a Ztnfr12 fusion protein that comprises a Ztnfr12 moiety and a human Fc fragment, wherein the C-terminus of the Ztnfr12 moiety is attached to the N-terminus of the Fc fragment via a peptide linker, such as a peptide consisting of the amino acid sequence of SEQ ID NO:4. The Ztnfr12 moiety can be a Ztnfr12 molecule or a fragment thereof. For example, a fusion protein can comprise an Fc fragment (e.g., a human Fc fragment), and amino acid residues 1 to about 69 of SEQ ID NO:2, or amino acid residues 1 to 79 of SEQ ID NO:2.

In another variation, a Ztnfr12 fusion protein comprises an IgG sequence, a Ztnfr12 moiety covalently joined to the aminoterminal end of the IgG sequence, and a signal peptide that is covalently joined to the aminoterminal of the Ztnfr12 moiety, wherein the IgG sequence consists of the following elements in the following order: a hinge region, a $CH_2$ domain, and a $CH_3$ domain. Accordingly, the IgG sequence lacks a $CH_1$ domain. The Ztnfr12 moiety displays a Ztnfr12 activity, as described herein, such as the ability to bind with a Ztnfr12 ligand (e.g., ZTNF4). This general approach to producing fusion proteins that comprise both antibody and nonantibody portions has been described by LaRochelle et al., EP 742830 (WO 95/21258).

Example 4 describes the construction of a Ztnfr12 fusion protein, in which the immunoglobulin moiety, derived from IgG, contains certain mutations. Five classes of immunoglobulin, IgG, IgA, IgM, IgD, and IgE, have been identified in higher vertebrates. IgG, IgD, and IgE proteins are characteristically disulfide linked heterotetramers consisting of two identical heavy chains and two identical light chains. Typically, IgM is found as a pentamer of a tetramer, whereas IgA occurs as a dimer of a tetramer.

IgG comprises the major class as it normally exists as the second most abundant protein found in plasma. In humans, IgG consists of four subclasses, designated IgG1, IgG2, IgG3, and IgG4. As shown in FIG. 1, each immunoglobulin heavy chain possesses a constant region that consists of constant region protein domains ($C_{H1}$, hinge, $C_{H2}$, and $C_{H3}$) that are invariant for a given subclass. The heavy chain constant regions of the IgG class are identified with the Greek symbol γ. For example, immunoglobulins of the IgG1 subclass contain a γ1 heavy chain constant region.

The Fc fragment, or Fc domain, consists of the disulfide linked heavy chain hinge regions, $C_{H2}$, and $C_{H3}$ domains. In immunoglobulin fusion proteins, Fc domains of the IgG1 subclass are often used as the immunoglobulin moiety, because IgG1 has the longest serum half-life of any of the serum proteins. Lengthy serum half-life can be a desirable protein characteristic for animal studies and potential human therapeutic use. In addition, the IgG1 subclass possesses the strongest ability to carry out antibody mediated effector functions. The primary effector function that may be most useful in an immunoglobulin fusion protein is the ability for an IgG1 antibody to mediate antibody dependent cellular cytotoxicity. On the other hand, this could be an undesirable function for a fusion protein whose primary function is as an antagonist. Several of the specific amino acid residues that are important for antibody constant region mediated activity in the IgG1 subclass have been identified. Inclusion or exclusion of these specific amino acids therefore allows for inclusion or exclusion of specific immunoglobulin constant region mediated activity.

Example 4 describes two versions of a modified human IgG1 Fc that were generated for creating Ztnfr12-Fc fusion protein. Fc4 and Fc5 contain mutations to reduce effector functions mediated by the Fc by reducing FcγRI binding and complement C1q binding. Specifically, three amino acid substitutions were introduced to reduce FcγRI binding. These are the substitutions at EU index positions 234, 235, and 237 (amino acid residues 38, 39, and 41 of SEQ ID NO:17, which is a sequence of a wild type immunoglobulin γ1 region). Substitutions at these positions have been shown to reduce binding to FcγRI (Duncan et al., Nature 332:563 (1988)). These amino acid substitutions may also reduce FcγRIIa binding, as well as FcγRIII binding (Sondermann et al., Nature 406:267 (2000); Wines et al., J. Immunol. 164:5313 (2000)).

Several groups have described the relevance of EU index positions 330 and 331 (amino acid residues 134 and 135 of SEQ ID NO:17) in complement C1q binding and subsequent complement fixation (Canfield and Morrison, J. Exp. Med. 173:1483 (1991); Tao et al., J. Exp. Med. 178:661 (1993)). Amino acid substitutions at these positions were introduced in Fc4 to reduce complement fixation. The $C_H3$ domain of Fc4 is identical to that found in the corresponding wild-type polypeptide, except for the stop codon, which was changed from TGA to TAA to eliminate a potential dam methylation site when the cloned DNA is grown in dam plus strains of *E. coli*.

In Fc5, the Arginine residue at EU index position 218 was mutated back to a lysine, because the BglII cloning scheme was not used in fusion proteins containing this particular Fc. The remainder of the Fc5 sequence matches the above description for Fc4.

Other useful Fc variants include Fc6, Fc7, and Fc8. Fc6 is identical to Fc5 except that the carboxyl terminal lysine codon has been eliminated. The C-terminal lysine of mature immunoglobulins is often removed from mature immunoglobulins post-translationally prior to secretion from B-cells, or removed during serum circulation. Consequently, the C-terminal lysine residue is typically not found on circulating antibodies. As in Fc4 and Fc5 above, the stop codon in the Fc6 sequence was changed to TAA.

Fc7 is identical to the wild type γ1 Fc except for an amino acid substitution at EU index position 297 located in the $C_{H2}$ domain, EU index position Asn-297 (amino acid residue 101 of SEQ ID NO:17) is a site of N-linked carbohydrate attachment. N-linked carbohydrate introduces a potential source of variability in a recombinantly expressed protein due to potential batch-to-batch variations in the carbohydrate structure. In an attempt to eliminate this potential variability, Asn-297 was mutated to a glutamine residue to prevent the attachment of N-linked carbohydrate at that residue position. The carbohydrate at residue 297 is also involved in Fc binding to the FcγRIII (Sondermann et al., Nature 406:267 (2000)). Therefore, removal of the carbohydrate should decrease binding of recombinant Fc7 containing fusion proteins to the FcγRs in general. As above, the stop codon in the Fc7 sequence was mutated to TAA.

Fc8 is identical to the wild type immunoglobulin γ1 region shown in SEQ ID NO:17, except that the cysteine residue at EU index position 220 (amino acid residue 24 of SEQ ID NO:17) was replaced with a serine residue. This mutation eliminated the cysteine residue that normally disulfide bonds with the immunoglobulin light chain constant region.

The present invention contemplates Ztnfr12-immunoglobulin fusion proteins that comprise a Ztnfr12 receptor moiety consisting of amino acid residues 7 to 69 of SEQ ID NO:2, amino acid residues 7 to 79 of SEQ ID NO:2, amino acid residues 7 to 39 of SEQ ID NO:2, amino acid residues 19 to 35 of SEQ ID NO:2, amino acid residues 1 to 69 of SEQ ID NO:2, amino acid residues 1 to 79 of SEQ ID NO:2, amino acid residues 1 to 71 of SEQ ID NO:2, amino acid residues 7 to 71 SEQ ID NO:2, or amino acid residues 1 to 39 of SEQ ID NO:2. More generally, the present invention includes Ztnfr12-immunoglobulin fusion proteins, wherein the Ztnfr12 receptor moiety consists of a fragment of amino acid residues 1 to 69 of SEQ ID NO:2, amino acid residues 1 to 71 of SEQ ID NO:2, amino acid residues 7 to 71 of SEQ ID NO:2, or amino acid residues 1 to 79 of SEQ ID NO:2, and wherein the Ztnfr12 receptor moiety binds at ZTNF4.

The immunoglobulin moiety of a fusion protein described herein comprises at least one constant region of an immunoglobulin. Preferably, the immunoglobulin moiety represents a segment of a human immunoglobulin. The human immunoglobulin sequence can be a wild-type amino acid sequence, or a modified wild-type amino acid sequence, which has at least one of the amino acid mutations discussed above.

The human immunoglobulin amino acid sequence can also vary from wild-type by having one or more mutations characteristic of a known allotypic determinant. Table 5 shows the allotypic determinants of the human IgGγ1 constant region (Putman, The Plasma Proteins, Vol. V, pages 49 to 140 (Academic Press, Inc. 1987)). EU index positions 214, 356, 358, and 431 define the known IgGγ1 allotypes. Position 214 is in the CHI domain of the IgGγ1 constant region, and, therefore, does not reside within the Fc sequence. The wild type Fc sequence of SEQ ID NO:17 includes the G1m(1) and G1m (2-) allotypes. However, the Fc moiety of a TACI-Fc protein can be modified to reflect any combination of these allotypes.

TABLE 5

Allotypic Determinants of the Human Immunoglobulin γ1 Constant Region

| Allotype | Amino Acid Residue | Amino Acid Position | |
|---|---|---|---|
| | | EU Index | SEQ ID NO: 17 |
| G1m(1) | Asp, Leu | 356, 358 | 160, 162 |
| G1m(1-) | Glu, Met | 356, 358 | 160, 162 |
| G1m(2) | Gly | 431 | 235 |
| G1m(2-) | Ala | 431 | 235 |
| G1m(3) | Arg | 214 | — |
| G1m(3-) | Lys | 214 | — |

The examples of Ztnfr12-Fc proteins disclosed herein comprise human IgG1 constant regions. However, suitable immunoglobulin moieties also include polypeptides comprising at least one constant region, such as a heavy chain constant region from any of the following immunoglobulins: IgG2, IgG3, IgG4, IgA1, IgA2, IgD, IgE, and IgM. The present invention also contemplates fusion proteins that comprise a Ztnfr12 receptor moiety, as described above, and either albumin or β2-macroglobulin, and the like, to produce Ztnfr12 dimers and multimers. Additional protein moieties suitable to produce Ztnfr12 fusion protein dimers and multimers are known to those of skill in the art.

In the treatment of certain conditions, it may be advantageous to combine a Ztnfr12-immunoglobulin fusion protein with at least one of a TACI-immunoglobulin fusion protein and BCMA-immunoglobulin fusion protein. This combination therapy can be achieved by administering various types of immunoglobulin fusion proteins, for example as dimers, or by administering heterodimers of Ztnfr12-immunoglobulin, TACI-immunoglobulin and BCMA-immunoglobulin fusion proteins.

The fusion proteins of the present invention can have the form of single chain polypeptides, dimers, trimers, or multiples of dimers or trimers. Dimers can be homodimers or heterodimers, and trimers can be homotrimers or heterotrimers. Examples of heterodimers include a Ztnfr12-immunoglobulin polypeptide with a BCMA-immunoglobulin polypeptide, a Ztnfr12-immunoglobulin polypeptide with a TACI-immunoglobulin polypeptide, and a BCMA-immunoglobulin polypeptide with a TACI-immunoglobulin polypeptide. Examples of heterotrimers include a Ztnfr12-immunoglobulin polypeptide with two BCMA-immunoglobulin polypeptides, a Ztnfr12-immunoglobulin polypeptide with two TACI-immunoglobulin polypeptides, a BCMA-immunoglobulin polypeptide with two Ztnfr12-immunoglobulin polypeptides, two TACI-immunoglobulin polypeptides with a BCMA-immunoglobulin polypeptide, one TACI-immunoglobulin polypeptide with two Ztnfr12-immunoglobulin polypeptides, two BCMA-immunoglobulin polypeptides with a TACI-immunoglobulin polypeptide, and a trimer of a TACI-immunoglobulin polypeptide, a BCMA-immunoglobulin polypeptide, and a Ztnfr12-immunoglobulin polypeptide.

In such fusion proteins, the TACI receptor moiety can comprise at least one of the following amino acid sequences of SEQ ID NO:8: amino acid residues 30 to 154, amino acid residues 34 to 66, amino acid residues 71 to 104, amino acid residues 47 to 62, and amino acid residues 86 to 100. The BCMA receptor moiety can comprise at least one of the following amino acid sequences of SEQ ID NO:7: amino acid residues 1 to 48, amino acid residues 8 to 41, and amino acid residues 21 to 37. The Ztnfr12 receptor moiety can comprise at least one of the following amino acid sequences of SEQ ID NO:2: amino acid residues 7 to 69, amino acid residues 7 to 79, amino acid residues 7 to 39, amino acid residues 19 to 35, amino acid residues 1 to 69, amino acid residues 1 to 79 of SEQ ID NO:2, amino acid residues 1 to 71 of SEQ ID NO:2, amino acid residues 7 to 71 of SEQ ID NO:2, or amino acid residues 1 to 39.

Immunoglobulin fusion proteins can be produced using standard methods. As an illustration, Example 4 describes the use of PCR methods used to construct the illustrative Ztnfr12-Fc5 fusion protein.

Other examples of antibody fusion proteins include polypeptides that comprise an antigen-binding domain and a Ztnfr12 fragment that contains a Ztnfr12 extracellular domain. Such molecules can be used to target particular tissues for the benefit of Ztnfr12 binding activity.

The present invention further provides a variety of other polypeptide fusions. For example, part or all of a domain(s) conferring a biological function can be swapped between Ztnfr12 of the present invention with the functionally equivalent domain(s) from another member of the tumor necrosis factor receptor family. Polypeptide fusions can be expressed in recombinant host cells to produce a variety of Ztnfr12 fusion analogs. A Ztnfr12 polypeptide can be fused to two or more moieties or domains, such as an affinity tag for purification and a targeting domain. Polypeptide fusions can also comprise one or more cleavage sites, particularly between domains. See, for example, Tuan et al., Connective Tissue Research 34:1 (1996).

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. General methods for enzymatic and chemical cleavage of fusion proteins are described, for example, by Ausubel (1995) at pages 16-19 to 16-25.

Ztnfr12 may bind ligands other than ZTNF4. Ztnfr12 polypeptides can be used to identify and to isolate such additional, potential Ztnfr12 ligands. For example, proteins and peptides of the present invention can be immobilized on a column and used to bind ligands from a biological sample that is run over the column (Hermanson et al. (eds.), Immobilized Affinity Ligand Techniques, pages 195-202 (Academic Press 1992)).

The activity of a Ztnfr12 polypeptide can be observed by a silicon-based biosensor microphysiometer, which measures the extracellular acidification rate or proton excretion associated with receptor binding and subsequent physiologic cellular responses. An exemplary device is the CYTOSENSOR Microphysiometer manufactured by Molecular Devices, Sunnyvale, Calif. A variety of cellular responses, such as cell proliferation, ion transport, energy production, inflammatory response, regulatory and receptor activation, and the like, can be measured by this method (see, for example, McConnell et al., Science 257:1906 (1992), Pitchford et al., Meth. Enzymol. 228:84 (1997), Arimilli et al., J. Immunol. Meth. 212:49 (1998), Van Liefde et al., Eur. J. Pharmacol. 346:87 (1998)). The microphysiometer can be used for assaying eukaryotic, prokaryotic, adherent, or non-adherent cells. By measuring extracellular acidification changes in cell media over time, the microphysiometer directly measures cellular responses to various stimuli, including agonists, ligands, or antagonists of Ztnfr12.

For example, the microphysiometer is used to measure responses of a Ztnfr12-expressing eukaryotic cell, compared to a control eukaryotic cell that does not express Ztnfr12 polypeptide. Suitable cells responsive to Ztnfr12-modulating stimuli include recombinant host cells comprising a Ztnfr12 expression vector, and cells that naturally express Ztnfr12. Extracellular acidification provides one measure for a Ztnfr12-modulated cellular response. In addition, this approach can be used to identify ligands, agonists, and antagonists of Ztnfr12 ligands. For example, a molecule can be identified as an agonist of Ztnfr12 ligand by providing cells that express a Ztnfr12 polypeptide, culturing a first portion of the cells in the absence of the test compound, culturing a second portion of the cells in the presence of the test compound, and determining whether the second portion exhibits a cellular response, in comparison with the first portion.

Alternatively, a solid phase system can be used to identify a new Ztnfr12 ligand, or an agonist or antagonist of ZTNF4. For example, a Ztnfr12 polypeptide or Ztnfr12 fusion protein can be immobilized onto the surface of a receptor chip of a commercially available biosensor instrument (BIACORE, Biacore AB; Uppsala, Sweden). The use of this instrument is disclosed, for example, by Karlsson, Immunol. Methods 145: 229 (1991), and Cunningham and Wells, J. Mol. Biol. 234: 554 (1993).

In brief, a Ztnfr12 polypeptide or fusion protein is covalently attached, using amine or sulfhydryl chemistry, to dextran fibers that are attached to gold film within a flow cell. A test sample is then passed through the cell. If a ligand is present in the sample, it will bind to the immobilized polypeptide or fusion protein, causing a change in the refractive index of the medium, which is detected as a change in surface plasmon resonance of the gold film. This system allows the determination of on- and off-rates, from which binding affinity can be calculated, and assessment of stoichiometry of binding. This system can also be used to examine antibody-antigen interactions, and the interactions of other complement/anti-complement pairs.

Ztnfr12 binding domains can be further characterized by physical analysis of structure, as determined by such techniques as nuclear magnetic resonance, crystallography, electron diffraction or photoaffinity labeling, in conjunction with mutation of putative contact site amino acids of Ztnfr12 ligand agonists. See, for example, de Vos et al., Science 255: 306 (1992), Smith et al., J. Mol. Biol. 224:899 (1992), and Wlodaver et al., FEBS Lett. 309:59 (1992).

The present invention also contemplates chemically modified Ztnfr12 compositions, in which a Ztnfr12 polypeptide is linked with a polymer. Illustrative Ztnfr12 polypeptides are soluble polypeptides that lack a functional transmembrane domain, such as a polypeptide consisting of amino acid residues 1 to about 69 of SEQ ID NO:2, or a polypeptide consisting of amino acid residues 1 to about 79 of SEQ ID NO:2. Typically, the polymer is water-soluble so that the Ztnfr12 conjugate does not precipitate in an aqueous environment, such as a physiological environment. An example of a suitable polymer is one that has been modified to have a single reactive group, such as an active ester for acylation, or an aldehyde for alkylation, In this way, the degree of polymerization can be controlled. An example of a reactive aldehyde is polyethylene glycol propionaldehyde, or mono-($C_1$-$C_{10}$) alkoxy, or aryloxy derivatives thereof (see, for example, Harris, et al., U.S. Pat. No. 5,252,714). The polymer may be branched or unbranched. Moreover, a mixture of polymers can be used to produce Ztnfr12 conjugates.

Ztnfr12 conjugates used for therapy can comprise pharmaceutically acceptable water-soluble polymer moieties. Suitable water-soluble polymers include polyethylene glycol (PEG), monomethoxy-PEG, mono-($C_1$-$C_{10}$)alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A Ztnfr12 conjugate can also comprise a mixture of such water-soluble polymers.

One example of a Ztnfr12 conjugate comprises a Ztnfr12 moiety and a polyalkyl oxide moiety attached to the N-terminus of the Ztnfr12 moiety. PEG is one suitable polyalkyl oxide. As an illustration, Ztnfr12 can be modified with PEG, a process known as "PEGylation." PEGylation of Ztnfr12 can be carried out by any of the PEGylation reactions known in the art (see, for example, EP 0 154 316, Delgado et al., Critical Reviews in Therapeutic Drug Carrier Systems 9:249 (1992), Duncan and Spreafico, Clin. Pharmacokinet. 27:290 (1994), and Francis et al., Int J Hematol 68:1 (1998)). For example, PEGylation can be performed by an acylation reaction or by an alkylation reaction with a reactive polyethylene glycol molecule. In an alternative approach, Ztnfr12 conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with a Ztnfr12 polypeptide. An example of an activated PEG ester is PEG esterified to N-hydroxysuccinimide. As used herein, the term "acylation" includes the following types of linkages between Ztnfr12 and a water-soluble polymer: amide, carbamate, urethane, and the like. Methods for preparing PEGylated Ztnfr12 by acylation will typically comprise the steps of (a) reacting a Ztnfr12 polypeptide with PEG (such as a reactive ester of an aldehyde derivative of PEG) under conditions whereby one or more PEG groups attach to Ztnfr12, and (b) obtaining the reaction product(s). Generally, the optimal reaction conditions for acylation reactions will be determined based upon known parameters and desired results. For example, the larger the ratio of PEG:Ztnfr12, the greater the percentage of polyPEGylated Ztnfr12 product.

The product of PEGylation by acylation is typically a polyPEGylated Ztnfr12 product, wherein the lysine ε-amino groups are PEGylated via an acyl linking group. An example of a connecting linkage is an amide. Typically, the resulting Ztnfr12 will be at least 95% mono-, di-, or tri-pegylated, although some species with higher degrees of PEGylation may be formed depending upon the reaction conditions. PEGylated species can be separated from unconjugated Ztnfr12 polypeptides using standard purification methods, such as dialysis, ultrafiltration, ion exchange chromatography, affinity chromatography, and the like.

PEGylation by alkylation generally involves reacting a terminal aldehyde derivative of PEG with Ztnfr12 in the presence of a reducing agent. PEG groups can be attached to the polypeptide via a —$CH_2$—NH group.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the ε-amino groups of the lysine residues and the α-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups. The present invention provides a substantially homogenous preparation of Ztnfr12 monopolymer conjugates.

Reductive alkylation to produce a substantially homogenous population of monopolymer Ztnfr12 conjugate molecule can comprise the steps of: (a) reacting a Ztnfr12 polypeptide with a reactive PEG under reductive alkylation conditions at a pH suitable to permit selective modification of the α-amino group at the amino terminus of the Ztnfr12, and (b) obtaining the reaction product(s). The reducing agent used for reductive alkylation should be stable in aqueous solution and able to reduce only the Schiff base formed in the initial process of reductive alkylation. Illustrative reducing agents include sodium borohydride, sodium cyanoborohydride, dimethylamine borane, trimethylamine borane, and pyridine borane.

For a substantially homogenous population of monopolymer Ztnfr12 conjugates, the reductive alkylation reaction conditions are those which permit the selective attachment of the water soluble polymer moiety to the N-terminus of Ztnfr12. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal α-group, the more polymer is needed to achieve optimal conditions. If the pH is higher, the polymer:Ztnfr12 need not be as large because more reactive groups are available. Typically, the pH will fall within the range of 3 to 9, or 3 to 6.

Another factor to consider is the molecular weight of the water-soluble polymer. Generally, the higher the molecular weight of the polymer, the fewer number of polymer molecules which may be attached to the protein. For PEGylation reactions, the typical molecular weight is about 2 kDa to about 100 kDa, about 5 kDa to about 50 kDa, or about 12 kDa to about 25 kDa. The molar ratio of water-soluble polymer to Ztnfr12 will generally be in the range of 1:1 to 100:1. Typically, the molar ratio of water-soluble polymer to Ztnfr12 will be 1:1 to 20:1 for polyPEGylation, and 1:1 to 5:1 for monoPEGylation.

General methods for producing conjugates comprising a polypeptide and water-soluble polymer moieties are known in the art. See, for example, Karasiewicz et al., U.S. Pat. No. 5,382,657, Greenwald et al., U.S. Pat. No. 5,738,846, Nieforth et al., Clin. Pharmacol. Ther. 59:636 (1996), Monkarsh et al., Anal. Biochem. 247:434 (1997)).

The present invention contemplates compositions comprising a peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

In addition, compositions can comprise a carrier, a Ztnfr12 polypeptide, and at least one of a TACI polypeptide or a BCMA polypeptide. Certain compositions can comprise soluble forms of these receptors. Examples of such compositions include compositions comprising carrier, a Ztnfr12 polypeptide comprising amino acid residues 7 to 69 of SEQ ID NO:2 (e.g., a polypeptide consisting of amino acid residues 1 to 79, 1 to 69, 7 to 79, 1 to 71, or 7 to 71, of SEQ ID NO:2(1) a BCMA polypeptide comprising amino acid residues 1 to 51 of SEQ ID NO:7, (2) a TACI polypeptide comprising amino acid residues 1 to 166 of SEQ ID NO:8, or (3) a BCMA polypeptide comprising amino acid residues 1 to 51 of SEQ ID NO:7, and a TACI polypeptide comprising amino acid residues 1 to 166 of SEQ ID NO:8.

7. Assays for Ztnfr12 Polypeptides and Fusion Proteins

The function of Ztnfr12 polypeptides and Ztnfr12-immunoglobulin fusion proteins can be examined using a variety of approaches to assess the ability of the fusion proteins to bind ZTNF4. For example, one approach measures the ability of Ztnfr12 polypeptides or Ztnfr12-immunoglobulin fusion protein to compete with Ztnfr12-coated plates for binding of $^{125}$I-labeled ZTNF4. As an illustration, 50 □g of the ZTNF4 can be labeled with 4 mCi of $^{125}$I using a single IODO-BEAD (Pierce; Rockford, Ill.). The reaction is quenched with a 0.25% solution of bovine serum albumin, and the free $^{125}$I is removed by gel filtration using a PD-10 column (Pierce). The specific radioactivity of $^{125}$I-ZTNF4 preparations is determined by trichloroacetic acid precipitation before and after the desalting step. An N-terminal fragment of the Ztnfr12 receptor, designated as "Ztnfr12-N," is added to 96-well plates (e.g., 100 □l at 0.1 □g/ml), and incubated overnight at 4° C. The plates are washed, blocked with SUPERBLOCK (Pierce), and washed again. The Ztnfr12 polypeptides or Ztnfr12-Fc constructs, at various concentrations ranging from 0 to about 12 ng/ml, are mixed with a fixed concentration of $^{125}$I-ZTNF4, and incubated for about two hours at 37° C. on the plate coated with Ztnfr12-N. Controls contain either Ztnfr12-N in solution, or lack Ztnfr12 polypeptides or Ztnfr12-Fc constructs. After incubation, the plates are washed and counted.

In another approach, increasing concentrations of $^{125}$I labeled ZTNF4 are incubated with Ztnfr12 polypeptides or Ztnfr12-Fc constructs, and the radioactivity associated with precipitated ZTNF4-Ztnfr12 polypeptide complexes, or ZTNF4-Ztnfr12-Fc complexes, is determined. As an illustration, about 0.05 nM of Ztnfr12 polypeptides or Ztnfr12-Fc construct can be incubated with about 0.4 pM to about 1.5 nM $^{125}$I-ZTNF4 for 30 minutes at room temperature in a total volume of 0.25 ml/tube. A Pansorbin (Staph A) suspension is added to each tube, and after 15 minutes, the samples are centrifuged, washed twice, and the pellets counted. Nonspecific binding is determined by the addition of 130 nM unlabeled ZTNF4 to the $^{125}$I-ZTNF4/Ztnfr12 polypeptide mix, or to the $^{125}$I-ZTNF4/Ztnfr12-Fc mix. Specific binding is calculated by subtracting the cpm bound in the presence of unlabeled ZTNF4 from the total cpm bound at each concentration of $^{125}$I-ZTNF4.

Alternatively, Ztnfr12 polypeptides and Ztnfr12-immunoglobulin fusion proteins can be characterized by the ability to inhibit the stimulation of human B cells by soluble ZTNF4, as described by Gross et al., international publication No. WO00/40716. Briefly, human B cells are isolated from peripheral blood mononuclear cells using CD19 magnetic beads and the VarioMacs magnetic separation system (Miltenyi Biotec; Auburn, Calif.) according to the manufacturer's instructions. Purified B cells are mixed with soluble ZTNF4 (25 ng/ml) and recombinant human IL-4 (10 ng/ml Pharmingen), and the cells are plated onto round bottom 96 well plates at $1\times10^5$ cells per well.

Ztnfr12 polypeptides or Ztnfr12-immunoglobulin proteins can be diluted from about 5 μg/ml to about 6 ng/ml, and incubated with the B cells for five days, pulsing overnight on day four with 1 μCi $^3$H-thymidine per well. As a control, Ztnfr12 polypeptides or Ztnfr12-immunoglobulin protein can also be incubated with B cells and IL-4 without ZTNF4. Plates are harvested using Packard plate harvester, and counted using the Packard reader.

Well-established animal models are available to test in vivo efficacy of Ztnfr12 polypeptides or Ztnfr12-immunoglobulin proteins in certain disease states. For example, Ztnfr12 polypeptides or Ztnfr12-immunoglobulin proteins can be tested in a number of animal models of autoimmune disease, such as MRL-lpr/lpr or NZBxNZW F1 congenic mouse strains, which serve as a model of SLE (systemic lupus erythematosus). Such animal models are known in the art (see, for example, Cohen and Miller (Eds.), Autoimmune Disease Models: A Guidebook (Academic Press, Inc. 1994).

Offspring of a cross between New Zealand Black (ZB) and New Zealand White (NZW) mice develop a spontaneous form of SLE that closely resembles SLE in humans. The offspring mice, known as NZBW begin to develop IgM autoantibodies against T-cells at one month of age, and by five to seven months of age, anti-DNA autoantibodies are the dominant immunoglobulin. Polyclonal B-cell hyperactivity leads to overproduction of autoantibodies. The deposition of these autoantibodies, particularly those directed against single stranded DNA, is associated with the development of glomerulonephritis, which manifests clinically as proteinuria, azotemia, and death from renal failure.

Kidney failure is the leading cause of death in mice affected with spontaneous SLE, and in the NZBW strain, this process is chronic and obliterative. The disease is more rapid and severe in females than males, with mean survival of only 245 days as compared to 406 days for the males. While many of the female mice will be symptomatic (proteinuria) by seven to nine months of age, some can be much younger or older when they develop symptoms. The fatal immune nephritis seen in the NZBW mice is very similar to the glomerulonephritis seen in human SLE, making this spontaneous murine model very attractive for testing of potential SLE therapeutics (Putterman and Naparstek, "Murine Models of Spontaneous Systemic Lupus Erythematosus," in Autoimmune Disease Models: A Guidebook, pages 217-234 (Academic Press, Inc., 1994); Mohan et al., J. Immunol. 154:1470 (1995); and Daikh et al., J. Immunol. 159:3104 (1997)).

As described by Gross et al., international publication No. WO00/40716, TACI-immunoglobulin proteins, which bind ZTNF4, can be administered to NZBW mice to monitor its suppressive effect on B cells over the five-week period when, on average, B-cell autoantibody production is believed to be at high levels in NZBW mice. This method can be applied to determine efficacy of a Ztnfr12 polypeptide of Ztnfr12-immunoglobulin fusion protein. Briefly, one hundred 8-week old female (NZBxNZW)F$_1$ mice can be divided into six groups of 15 mice. Prior to treatment, the mice are monitored once a month for urine protein, and blood is drawn for CBC and serum banking. Serum can be screened for the presence of autoantibodies. Because proteinuria is the hallmark sign of glomerulonephritis, urine protein levels are monitored by dipstick at regular intervals over the course of the study. Treatment can begin when mice are approximately five months of age. Mice can receive intraperitoneal injections of vehicle only (phosphate buffered saline) or human immunoglobulin (control protein) or Ztnfr12-immunoglobulin protein (e.g., 20 to 100 μg test protein per dose) three times a week for five weeks. Similar studies can be performed with Ztnfr12 polypeptides.

Blood is collected twice during treatment, and will be collected at least twice following treatment. Urine dipstick values for proteinuria and body weights are determined every two weeks after treatment begins. Blood, urine dipstick value and body weight are collected at the time of euthanasia. The spleen and thymus are divided for fluorescent activated cell sorting analysis and histology. Submandibular salivary glands, mesenteric lymph node chain, liver lobe with gall bladder, cecum and large intestine, stomach, small intestine, pancreas, right kidney, adrenal gland, tongue with trachea and esophagus, heart and lungs are also collected for histology.

Murine models for experimental allergic encephalomyelitis have been used as a tool to investigate both the mechanisms of immune-mediated disease, and methods of potential therapeutic intervention. The model resembles human multiple sclerosis, and produces demyelination as a result of T-cell activation to neuroproteins such as myelin basic protein, or proteolipid protein. Inoculation with antigen leads to induction of CD4+, class II MHC-restricted T-cells (Th1). Changes in the protocol for experimental allergic encephalomyelitis can produce acute, chronic-relapsing, or passive-transfer variants of the model (Weinberg et al., J. Immunol. 162:1818 (1999); Mijaba et al., Cell. Immunol. 186:94 (1999); and Glabinski, Meth. Enzym. 288:182 (1997)).

Gross et al., international publication No. WO00/40716, describe one approach to evaluating the efficacy of TACI-immunoglobulin proteins in the amelioration of symptoms associated with experimental allergic encephalomyelitis. Briefly, 25 female PLxSJL F1 mice (12 weeks old) are given a subcutaneous injection of 125 μg/mouse of antigen (myelin Proteolipid Protein, PLP, residues 139-151), formulated in complete Freund's Adjuvant. The mice are divided into five groups of five mice. Intraperitoneal injections of pertussis toxin (400 ng) are given on Day 0 and 2. The groups are given a 1×, 10×, or 100× dose of TACI-immunoglobulin protein, one group will receive vehicle only, and one group will receive no treatment. Prevention therapy begins on Day 0, intervention therapy begins on day 7, or at onset of clinical signs. Signs of disease, weight loss, and paralysis manifest in approximately 10 to 14 days, and last for about one week. Animals are assessed daily by collecting body weights and assigning a clinical score to correspond to the extent of their symptoms. Clinical signs of experimental allergic encephalomyelitis appear within 10 to 14 days of inoculation and persist for approximately one week. At the end of the study, all animals are euthanized by gas overdose, and necropsied. The brain and spinal column are collected for histology or frozen for mRNA analysis. Body weight and clinical score data are plotted by individual and by group. This approach can be used to test Ztnfr12 polypeptides or Ztnfr12-immunoglobulin fusion proteins.

In the collagen-induced arthritis model, mice develop chronic inflammatory arthritis, which closely resembles human rheumatoid arthritis. Since collagen-induced arthritis shares similar immunological and pathological features with rheumatoid arthritis, this makes it an ideal model for screening potential human anti-inflammatory compounds. Another advantage in using the collagen-induced arthritis model is that the mechanisms of pathogenesis are known. The T and B cell epitopes on type II collagen have been identified, and various immunological (delayed-type hypersensitivity and anti-collagen antibody) and inflammatory (cytokines, chemokines, and matrix-degrading enzymes) parameters relating to immune-mediating arthritis have been determined, and can be used to assess test compound efficacy in the models (Wooley, Curr. Opin. Rheum. 3:407 (1999); Williams et al., Immunol. 89:9784 (1992); Myers et al., Life Sci. 61:1861 (1997); and Wang et al., Immunol. 92:8955 (1995)).

Gross et al., international publication No. WO00/40716, describe a method for evaluating the efficacy of TACI-immunoglobulin proteins in the amelioration of symptoms associated with collagen-induced arthritis. In brief, eight-week old male DBA/1J mice (Jackson Labs) are divided into groups of five mice/group and are given two subcutaneous injections of 50 to 100 µl of 1 mg/ml collagen (chick or bovine origin), at three week intervals. One control does not receive collagen injections. The first injection is formulated in Complete Freund's Adjuvant, and the second injection is formulated in Incomplete Freund's Adjuvant. TACI-immunoglobulin protein is administered prophylactically at or before the second injection, or after the animal develops a clinical score of two or more that persists at least 24 hours. Animals begin to show symptoms of arthritis following the second collagen injection, usually within two to three weeks. For example, TACI-Fc, a control protein, human IgFc, or phosphate-buffered saline (vehicle) can be administered prophylactically beginning seven days before the second injection (day −7). Proteins can be administered at 100 µg, given three times a week as a 200 µl intraperitoneal injection, and continued for four weeks. The extent of disease is evaluated in each paw using a caliper to measure paw thickness and assigning a clinical score to each paw. For example, a clinical score of "0" indicates a normal mouse, a score of "1" indicates that one or more toes are inflamed, a score of "2" indicates mild paw inflammation, a score of "3" indicates moderate paw inflammation, and a score of "4" indicates severe paw inflammation. Animals are euthanized after the disease as been established for a set period of time, usually seven days. Paws are collected for histology or mRNA analysis, and serum is collected for immunoglobulin and cytokine assays. The collagen-induced arthritis model can be used to test Ztnfr12 polypeptides or Ztnfr12-immunoglobulin fusion proteins.

Myasthenia gravis is another autoimmune disease for which murine models are available. Myasthenia gravis is a disorder of neuromuscular transmission involving the production of autoantibodies directed against the nicotinic acetylcholine receptor. This disease is acquired or inherited with clinical features including abnormal weakness and fatigue on exertion.

A murine model of myasthenia gravis has been established. (Christadoss et al., "Establishment of a Mouse Model of Myasthenia gravis Which Mimics Human Myasthenia gravid Pathogenesis for Immune Intervention," in Immunobiology of Proteins and Peptides VIII, Atassi and Bixler (Eds.), pages 195-199 (1995)). Experimental autoimmune myasthenia gravis is an antibody mediated disease characterized by the presence of antibodies to acetylcholine receptor. These antibodies destroy the receptor leading to defective neuromuscular electrical impulses, resulting in muscle weakness. In the experimental autoimmune myasthenia gravis model, mice are immunized with the nicotinic acetylcholine receptor. Clinical signs of myasthenia gravis become evident weeks after the second immunization. Experimental autoimmune myasthenia gravis is evaluated by several methods including measuring serum levels of acetylcholine receptor antibodies by radioimmunoassay (Christadoss and Dauphinee, J. Immunol. 136:2437 (1986); Lindstrom et al., Methods Enzymol. 74:432 (1981)), measuring muscle acetylcholine receptor, or electromyography (Coligan et al. (Eds.), Protocols in Immunology. Vol. 3, page 15.8.1 (John Wiley & Sons, 1997)).

The effect of Ztnfr12 polypeptides or Zntfr12-immunoglobulin fusion proteins on experimental autoimmune myasthenia gravis can be determined by administering fusion proteins during ongoing clinical myasthenia gravis in B6 mice. For example, 100 B6 mice are immunized with 20 µg acetylcholine receptor in complete Freund's adjuvant on days 0 and 30. Approximately 40 to 60% of mice will develop moderate (grade 2) to severe (grade 3) clinical myasthenia gravis after the boost with acetylcholine receptor. Mice with grade 2 and 3 clinical disease are divided into three groups (with equal grades of weakness) and weighed (mice with weakness also lose weight, since they have difficulty in consuming food and water) and bled for serum (for pre-treatment anti-acetylcholine receptor antibody and isotype level). Group A is injected I.P with phosphate buffered saline, group B is injected intraperitoneally with human IgG-Fc as a control protein (100 µg), and group C is injected with 100 µg of Ztnfr12 polypeptides or Zntfr12-immunoglobulin fusion proteins three times a week for four weeks. Mice are screened for clinical muscle weakness twice a week, and weighed and bled for serum 15 and 30 days after the commencement of treatment. Whole blood is collected on day 15 to determine T/B cell ratio by fluorescence activated cell sorter analysis using markers B220 and CD5. Surviving mice are killed 30 to 45 days after the initiation of treatment, and their carcasses are frozen for later extraction of muscle acetylcholine receptor to determine the loss of muscle acetylcholine receptor, the primary pathology in myasthenia gravis (see, for example, Coligan et al. (Eds.), Protocols in Immunology. Vol. 3, page 15.8.1 (John Wiley & Sons, 1997)).

Serum antibodies to mouse muscle acetylcholine receptor can be determined by an established radioimmunoassay, and anti-acetylcholine receptor antibody isotypes (IgM, IgG1, IgG2b and IgG2c) is measured by ELISA. Such methods are known. The effects of Ztnfr12 polypeptides or Zntfr12-immunoglobulin fusion proteins on ongoing clinical myasthenia gravis, anti-acetylcholine receptor antibody and isotype level, and muscle acetylcholine receptor loss are determined.

Approximately 100 mice can be immunized with 20 µg acetylcholine receptor in complete Freund's adjuvant on day 0 and 30. Mice with clinical myasthenia gravis are divided into four groups. Group A is injected intraperitoneally with 100 µg control Fc, group B is injected with 20 µg control Fc, group C is injected with 100 µg Ztnfr12 polypeptide or Zntfr12-immunoglobulin fusion protein, and group D is injected with 20 µg Ztnfr12 polypeptide or Zntfr12-immunoglobulin fusion protein three times a week for four weeks. Mice are weighed and bled for serum before, and 15 and 30 days after the start of the treatment. Serum is tested for anti-acetylcholine receptor antibody and isotypes as described above. Muscle acetylcholine receptor loss can also be measured.

These in vitro and in vivo assays can also be used to evaluate Ztnfr12 antibody components, antibody fusion proteins, immunoconjugates, and the like. Other suitable assays of Ztnfr12 polypeptides, Zntfr12-immunoglobulin fusion proteins, or Ztnfr12 antibody components can be determined by those of skill in the art.

8. Isolation of Ztnfr12 Polypeptides

The polypeptides of the present invention can be purified to at least about 80% purity, to at least about 90% purity, to at least about 95% purity, or greater than 95% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. In certain preparations, purified polypeptide is substantially free of other polypeptides, particularly other polypeptides of animal origin.

Fractionation and/or conventional purification methods can be used to obtain preparations of Ztnfr12 purified from natural sources (e.g., lymph node tissue), synthetic Ztnfr12 polypeptides, and recombinant Ztnfr12 polypeptides and fusion Ztnfr12 polypeptides purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are suitable. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, for example, Affinity Chromatography: Principles & Methods (Pharmacia LKB Biotechnology 1988), and Doonan, Protein Purification Protocols (The Humana Press 1996).

Additional variations in Ztnfr12 isolation and purification can be devised by those of skill in the art. For example, anti-Ztnfr12 antibodies, obtained as described below, can be used to isolate large quantities of protein by immunoaffinity purification.

The polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, Trends in Biochem. 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (M. Deutscher, (ed.), Meth. Enzymol. 182:529 (1990)). Within additional embodiments of the invention, a fusion of the polypeptide of interest and an affinity tag (e.g., maltose-binding protein, an immunoglobulin domain) may be constructed to facilitate purification.

Ztnfr12 polypeptides or fragments thereof may also be prepared through chemical synthesis, as described above. Ztnfr12 polypeptides may be monomers or multimers; glycosylated or non-glycosylated; PEGylated or non-PEGylated; and may or may not include an initial methionine amino acid residue.

9. Production of Antibodies to Ztnfr12 Proteins

Antibodies to Ztnfr12 can be obtained, for example, using the product of a Ztnfr12 expression vector or Ztnfr12 isolated from a natural source as an antigen. Particularly useful anti-Ztnfr12 antibodies "bind specifically" with Ztnfr12. Antibodies are considered to be specifically binding if the antibodies exhibit at least one of the following two properties: (1) antibodies bind to Ztnfr12 with a threshold level of binding activity, and (2) antibodies do not significantly cross-react with polypeptides related to Ztnfr12.

With regard to the first characteristic, antibodies specifically bind if they bind to a Ztnfr12 polypeptide, peptide or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, Ann. NY Acad. Sci. 51:660 (1949)). With regard to the second characteristic, antibodies do not significantly cross-react with related polypeptide molecules, for example, if they detect Ztnfr12, but not presently known polypeptides using a standard Western blot analysis. Examples of known related polypeptides include known tumor necrosis factor receptors. For example, certain anti-Ztnfr12 antibodies bind with Ztnfr12, but not with TACI or BCMA.

Anti-Ztnfr12 antibodies can be produced using antigenic Ztnfr12 epitope-bearing peptides and polypeptides. Antigenic epitope-bearing peptides and polypeptides of the present invention contain a sequence of at least nine, or between 15 to about 30 amino acids contained within SEQ ID NO:2 or another amino acid sequence disclosed herein. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with Ztnfr12. It is desirable that the amino acid sequence of the epitope-bearing peptide is selected to provide substantial solubility in aqueous solvents (i.e., the sequence includes relatively hydrophilic residues, while hydrophobic residues are typically avoided). Moreover, amino acid sequences containing proline residues may be also be desirable for antibody production.

As an illustration, potential antigenic sites in Ztnfr12 were identified using the Jameson-Wolf method, Jameson and Wolf, CABIOS 4:181, (1988), as implemented by the PROTEAN program (version 3.14) of LASERGENE (DNASTAR; Madison, Wis.). Default parameters were used in this analysis.

The Jameson-Wolf method predicts potential antigenic determinants by combining six major subroutines for protein structural prediction. Briefly, the Hopp-Woods method, Hopp et al., Proc. Nat'l Acad. Sci. USA 78:3824 (1981), was first used to identify amino acid sequences representing areas of greatest local hydrophilicity (parameter: seven residues averaged). In the second step, Emini's method, Emini et al., J. Virology 55:836 (1985), was used to calculate surface probabilities (parameter: surface decision threshold (0.6)=1). Third, the Karplus-Schultz method, Karplus and Schultz, Naturwissenschaften 72:212 (1985), was used to predict backbone chain flexibility (parameter: flexibility threshold (0.2)=1). In the fourth and fifth steps of the analysis, secondary structure predictions were applied to the data using the methods of Chou-Fasman, Chou, "Prediction of Protein Structural Classes from Amino Acid Composition," in Prediction of Protein Structure and the Principles of Protein Conformation, Fasman (ed.), pages 549-586 (Plenum Press 1990), and Garnier-Robson, Garnier et al., J. Mol. Biol. 120: 97 (1978) (Chou-Fasman parameters: conformation table=64 proteins; α region threshold=103; β region threshold=105; Garnier-Robson parameters: α and β decision constants=0). In the sixth subroutine, flexibility parameters and hydropathy/solvent accessibility factors were combined to determine a surface contour value, designated as the "antigenic index." Finally, a peak broadening function was applied to the antigenic index, which broadens major surface peaks by adding 20, 40, 60, or 80% of the respective peak value to account for additional free energy derived from the mobility of surface regions relative to interior regions. This calculation was not applied, however, to any major peak that resides in a helical region, since helical regions tend to be less flexible.

The results of this analysis indicated that the following amino acid sequences of SEQ ID NO:2 would provide suitable antigenic molecules: amino acids 1 to 17, amino acids 39 to 64, 102 to 129, amino acids 135 to 142, amino acids 146 to 159, and amino acids 174 to 182. The present invention contemplates the use of any one of these antigenic amino acid sequences to generate antibodies to Ztnfr12. The present invention also contemplates polypeptides comprising at least one of these antigenic molecules.

Similarly, the results of Jameson-Wolf analysis indicated that the following amino acid sequences of SEQ ID NO:13 would provide suitable antigenic molecules: amino acids 10 to 26, amino acids 45 to 69, 106 to 113, and amino acids 139 to 151. The present invention contemplates the use of any one of these antigenic amino acid sequences to generate antibodies to murine Ztnfr12. The present invention also contemplates polypeptides comprising at least one of these antigenic molecules.

Useful antibodies can also be produced using antigenic molecules that comprise at least one Ztnfr12 exon of the human gene. For example, such antigenic molecules can comprise polypeptides that consist of the following amino acid sequences of SEQ ID NO:2: amino acid residues 1 to 45, amino acid residues 47 to 122, and amino acid residues 124 to 184.

Antibodies that block signal transduction by ZTNF4 can be useful in therapeutic applications. Blocking anti-Ztnfr12 antibodies can be identified, for example, by their inhibition of biotin-ZTNF4 binding to Ztnfr12 on tumor cell lines. Antibodies that bind with the Ztnfr12 intracellular domain can also be used to block ZTNF4-induced signal transduction. Such antibodies can bind the intracellular domain of Ztnfr12 within amino acid residues 101 to 184 of SEQ ID NO:2. In addition, a potential TRAF binding domain resides at amino acid residues 159 to 178 of SEQ ID NO:2. Thus, certain signal-blocking antibodies can bind the intracellular domain of Ztnfr12 within this region. The present invention includes antibodies that bind Ztnfr12 within amino acid residues 159 to 178 of SEQ ID NO:2. Standard methods are available to introduce antibodies to the intracellular compartment of cells. For example, such antibodies can be encapsulated in liposomes.

Signal-inducing anti-Ztnfr12 antibodies are also useful. Antibodies that induce a signal by binding to a Ztnfr12 receptor can also be identified using a suitable reporter cell line that contains a transcriptional reporter element and Ztnfr12. As an illustration, an engineered mammalian cell line (e.g., Jurkat), which expresses Ztnfr12, and a transcriptional reporter gene can be used to test anti-Ztnfr12 monoclonal antibodies for their ability to stimulate transcription of a reporter gene (e.g., luciferase).

Polyclonal antibodies to recombinant Ztnfr12 protein or to Ztnfr12 isolated from natural sources can be prepared using methods well-known to those of skill in the art. See, for example, Green et al., "Production of Polyclonal Antisera," in Immunochemical Protocols (Manson, ed.), pages 1-5 (Humana Press 1992), and Williams et al., "Expression of foreign proteins in E. coli using plasmid vectors and purification of specific polyclonal antibodies," in DNA Cloning 2: Expression Systems, 2nd Edition, Glover et al. (eds.), page 15 (Oxford University Press 1995). The immunogenicity of a Ztnfr12 polypeptide can be increased through the use of an adjuvant, such as alum (aluminum hydroxide) or Freund's complete or incomplete adjuvant. Polypeptides useful for immunization also include fusion polypeptides, such as fusions of Ztnfr12 or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, guinea pigs, goats, or sheep, an anti-Ztnfr12 antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., Int. J. Cancer 46:310 (1990).

Alternatively, monoclonal anti-Ztnfr12 antibodies can be generated. Rodent mono-clonal antibodies to specific antigens may be obtained by methods known to those skilled in the art (see, for example, Kohler et al., Nature 256:495 (1975), Coligan et al. (eds.), Current Protocols in Immunology, Vol. 1, pages 2.5.1-2.6.7 (John Wiley & Sons 1991) ["Coligan"], Picksley et al., "Production of monoclonal antibodies against proteins expressed in E. coli," in DNA Cloning 2: Expression Systems, 2nd Edition, Glover et al. (eds.), page 93 (Oxford University Press 1995)).

Briefly, monoclonal antibodies can be obtained by injecting mice with a composition comprising a Ztnfr12 gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-Ztnfr12 antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., Nature Genet. 7:13 (1994), Lonberg et al., Nature 368:856 (1994), and Taylor et al., Int. Immun. 6:579 (1994).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in Methods in Molecular Biology, Vol. 10, pages 79-104 (The Humana Press, Inc. 1992)).

For particular uses, it may be desirable to prepare fragments of anti-Ztnfr12 antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted $F(ab')_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., Arch Biochem. Biophys. 89:230 (1960), Porter, Biochem. J. 73:119 (1959), Edelman et al., in Methods in Enzymology Vol. 1, page 422 (Academic Press 1967), and by Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., Proc. Nat'l Acad. Sci. USA 69:2659 (1972). Alternatively, the variable chains can be linked by an intermolecular disulfide bond or cross-linked by chemicals such as glutaraldehyde (see, for example, Sandhu, Crit. Rev. Biotech. 12:437 (1992)).

The Fv fragments may comprise $V_H$ and $V_L$ chains, which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector, which is subsequently introduced into a host cell, such as E. coli. The recombinant host cells synthesize a single polypeptide chain with a linker peptide bridging the two V domains. Methods for producing scFvs are described, for example, by Whitlow et al., Methods: A Companion to Methods in Enzymology 2:97 (1991) (also see, Bird et al., Science 242:423 (1988), Ladner et al., U.S. Pat. No. 4,946,778, Pack et al., Bio/Technology 11:1271 (1993), and Sandhu, supra).

As an illustration, a scFV can be obtained by exposing lymphocytes to Ztnfr12 polypeptide in vitro, and selecting antibody display libraries in phage or similar vectors (for instance, through use of immobilized or labeled Ztnfr12 protein or peptide). Genes encoding polypeptides having potential Ztnfr12 polypeptide binding domains can be obtained by screening random peptide libraries displayed on phage (phage display) or on bacteria, such as E. coli. Nucleotide sequences encoding the polypeptides can be obtained in a number of ways, such as through random mutagenesis and random polynucleotide synthesis. These random peptide display libraries can be used to screen for peptides, which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., Phage Display of Peptides and Proteins (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the Ztnfr12 sequences disclosed herein to identify proteins which bind to Ztnfr12.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., Methods: A Companion to Methods in Enzymology 2:106 (1991), Courtenay-Luck, "Genetic Manipulation of Monoclonal Antibodies," in Monoclonal Antibodies: Production, Engineering and Clinical Application, Ritter et al. (eds.), page 166 (Cambridge University Press 1995), and Ward et al., "Genetic Manipulation and Expression of Antibodies," in Monoclonal Antibodies: Principles and Applications, Birch et al., (eds.), page 137 (Wiley-Liss, Inc. 1995)).

Another useful anti-receptor antibody is a chimeric antibody. A chimeric antibody comprises the variable domains and complementary determining regions derived from a rodent antibody, while the remainder of the antibody molecule is derived from a human antibody. See, for example, Verma and Boleti, "Engineering Antibody Molecules," in Diagnostic and Therapeutic Antibodies, George and Urch (Eds.), pages 35-52 (Humana Press, Inc. 2000).

Alternatively, an anti-Ztnfr12 antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Nat'l Acad. Sci. USA 86:3833 (1989). Techniques for producing humanized monoclonal antibodies are described, for example, by Jones et al., Nature 321:522 (1986), Carter et al., Proc. Nat'l Acad. Sci. USA 89:4285 (1992), Sandhu, Crit. Rev. Biotech. 12:437 (1992), Singer et al., J. Immun. 150:2844 (1993), Sudhir (ed.), Antibody Engineering Protocols (Humana Press, Inc. 1995), Kelley, "Engineering Therapeutic Antibodies," in Protein Engineering: Principles and Practice, Cleland et al. (eds.), pages 399-434 (John Wiley & Sons, Inc. 1996), and by Queen et al., U.S. Pat. No. 5,693,762 (1997).

The present invention includes the use of compositions that comprise an antibody component that binds the Ztnfr12 extracellular region, and an antibody component that binds at least one of a TACI extracellular region and a BCMA extracellular region. For example, such a "multispecific antibody composition" can comprise a heteroantibody mixture (i.e., an aggregate of at least two antibody components, each having a different binding specificity), a bispecific antibody (i.e., an antibody component with two different combining sites), a single chain bispecific polypeptide, and the like.

Bispecific antibodies can be made by a variety of conventional methods. As an illustration, bispecific antibodies have been prepared by oxidative cleavage of Fab' fragments resulting from reductive cleavage of different antibodies. See, for example, Winter et al., Nature 349:293 (1991). This can be carried out by mixing two different $F(ab')_2$ fragments produced by pepsin digestion of two different antibodies, reductive cleavage to form a mixture of Fab' fragments, followed by oxidative reformation of the disulfide linkages to produce a mixture of $F(ab')_2$ fragments including bispecific antibodies containing a Fab' potion specific to each of the original epitopes. General techniques for the preparation of such bispecific antibodies can be found, for example, in Nisonhoff et al., Arch Biochem. Biophys. 93:470 (1961), Hammerling et al., J. Exp. Med. 128:1461 (1968), and U.S. Pat. No. 4,331,647.

Alternatively, linkage can be achieved by using a heterobifunctional linker such as maleimide-hydroxysuccinimide ester. Reaction of the ester with an antibody or fragment will derivatize amine groups on the antibody or fragment, and the derivative can then be reacted with, for example, an antibody Fab fragment having free sulfhydryl groups (or, a larger fragment or intact antibody with sulfhydryl groups appended thereto by, for example, Traut's Reagent). Such a linker is less likely to crosslink groups in the same antibody and improves the selectivity of the linkage.

As another example, bispecific $F(ab')_2$ antibodies can be produced by linking two Fab' fragments via their hinge region SH groups using the bifunctional crosslinker o-phenylenedimaleimide. See, for example, Tso, "$F(ab')_2$ Fusion Proteins and Bispecific $F(ab')_2$," in Chamow and Ashkenazi (Eds.), Antibody Fusion Proteins, pages 127-150 (Wiley-Liss, Inc. 1999), and French, "How to Make Bispecific Antibodies," in George and Urch (Eds.), Diagnostic and Therapeutic Antibodies, pages 333-339 (Humana Press, Inc. 2000).

It is advantageous to link the antibodies or fragments at sites remote from the antigen binding sites. This can be accomplished by, for example, linkage to cleaved interchain sulfydryl groups, as noted above. Another method involves reacting an antibody having an oxidized carbohydrate portion with another antibody which has at lease one free amine function. This results in an initial Schiff base (imine) linkage, which can be stabilized by reduction to a secondary amine, for example, by borohydride reduction, to form the final composite. Such site-specific linkages are disclosed, for small molecules, in U.S. Pat. No. 4,671,958, and for larger addends in U.S. Pat. No. 4,699,784.

Alternatively, bispecific antibodies can be produced by fusing two hybridoma cell lines, one cell line that produces anti-Ztnfr12 monoclonal antibody, and one cell line that produces either anti-BCMA monoclonal antibody, or anti-TACI monoclonal antibody. Techniques for producing tetradomas are described, for example, by Milstein et al., Nature 305:537 (1983), and Pohl et al., Int. J. Cancer 54:418 (1993).

Bispecific antibodies can also be produced by genetic engineering. For example, vectors containing DNA coding for variable domains of an anti-Ztnfr12 monoclonal antibody can be introduced into hybridomas that secrete anti-TACI antibodies, or anti-BCMA antibodies. The resulting transfectomas produce bispecific antibodies that bind Ztnfr12 and either BCMA or TACI. Alternatively, chimeric genes can be designed that encode an anti-Ztnfr12 binding domain and at least one anti-BCMA binding domain or anti-TACI binding domain. A variety of genetic strategies for producing bispecifc antibodies are available to those of skill in the art. In one approach, for example, bispecific $F(ab')_2$ are produced using leucine zippers. See, for example, Tso, "$F(ab')_2$ Fusion Proteins and Bispecific $F(ab')_2$," in Chamow and Ashkenazi (Eds.), Antibody Fusion Proteins, pages 127-150 (Wiley-Liss, Inc. 1999). General techniques for producing bispecific antibodies by genetic engineering are described, for example, by Songsivilai et al., Biochem. Biophys. Res. Commun. 164:271 (1989), Traunecker et al., EMBO J. 10:3655 (1991), and Weiner et al., J. Immunol. 147:4035 (1991).

A bispecific molecule of the invention can also be a single chain bispecific molecule, such as a single chain bispecific antibody, a single chain bispecific molecule comprising one single chain antibody and a binding determinant, or a single chain bispecific molecule comprising two binding determinants.

Bispecific antibodies can be screened using standard techniques, such as a bispecific ELISA.

The present invention further includes polyclonal anti-idiotype antibodies, which can be prepared by immunizing animals with anti-Ztnfr12 antibodies or antibody fragments, using standard techniques. See, for example, Green et al., "Production of Polyclonal Antisera," in Methods In Molecular Biology: Immunochemical Protocols, Manson (ed.), pages 1-12 (Humana Press 1992). Also, see Coligan at pages 2.4.1-2.4.7. Alternatively, monoclonal anti-idiotype antibodies can be prepared using anti-Ztnfr12 antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, J. Gen. Virol. 77:1875 (1996).

Anti-Ztnfr12 antibody components and anti-idiotype antibodies of the present invention can be useful to neutralize the effects of a Ztnfr12 ligand (e.g., ZTNF4) for treating pre-B or B-cell leukemias, such as plasma cell leukemia, chronic or acute lymphocytic leukemia, myelomas such as multiple myeloma, plasma cell myeloma, endothelial myeloma and giant cell myeloma, and lymphomas such as non-Hodgkins lymphoma, which are associated with an increase in a Ztnfr12 ligand (e.g., ZTNF4). Additional examples of B cell lymphomas that may be treated with the molecules described herein include Burkitt's lymphoma, Non-Burkitt's lymphoma, follicular lymphoma, acute lymphoblastic leukemia, large cell lymphoma, marginal zone lymphoma, mantle cell lymphoma, large cell lymphoma (e.g., immunoblastic lymphoma), small lymphocytic lymphoma, and other B cell lymphomas.

10. Use of Ztnfr12 Nucleotide Sequences to Detect Gene Expression and Gene Structure Nucleic acid molecules can be used to detect the expression of a Ztnfr12 gene in a biological sample. Suitable probe molecules include double-stranded nucleic acid molecules comprising the nucleotide sequence of SEQ ID NO:1, or a portion thereof, as well as single-stranded nucleic acid molecules having the complement of the nucleotide sequence of SEQ ID NO:1, or a portion thereof. Probe molecules may be DNA, RNA, oligonucleotides, and the like. As used herein, the term "portion" refers to at least eight nucleotides to at least 20 or more nucleotides. Illustrative probes bind with regions of the Ztnfr12 gene that have a low sequence similarity to comparable regions in other tumor necrosis factor receptor genes.

In a basic assay, a single-stranded probe molecule is incubated with RNA, isolated from a biological sample, under conditions of temperature and ionic strength that promote base pairing between the probe and target Ztnfr12 RNA species. After separating unbound probe from hybridized molecules, the amount of hybrids is detected.

Well-established hybridization methods of RNA detection include northern analysis and dot/slot blot hybridization (see, for example, Ausubel (1995) at pages 4-1 to 4-27, and Wu et al. (eds.), "Analysis of Gene Expression at the RNA Level," in Methods in Gene Biotechnology, pages 225-239 (CRC Press, Inc. 1997)). Nucleic acid probes can be detectably labeled with radioisotopes such as $^{32}P$ or $^{35}S$. Alternatively, Ztnfr12 RNA can be detected with a nonradioactive hybridization method (see, for example, Isaac (ed.), Protocols for Nucleic Acid Analysis by Nonradioactive Probes (Humana Press, Inc. 1993)). Typically, nonradioactive detection is achieved by enzymatic conversion of chromogenic or chemiluminescent substrates. Illustrative nonradioactive moieties include biotin, fluorescein, and digoxigenin.

Ztnfr12 oligonucleotide probes are also useful for in vivo diagnosis. As an illustration, $^{18}F$-labeled oligonucleotides can be administered to a subject and visualized by positron emission tomography (Tavitian et al., Nature Medicine 4:467 (1998)).

Numerous diagnostic procedures take advantage of the polymerase chain reaction (PCR) to increase sensitivity of detection methods. Standard techniques for performing PCR are well-known (see, generally, Mathew (ed.), Protocols in Human Molecular Genetics (Humana Press, Inc. 1991), White (ed.), PCR Protocols: Current Methods and Applications (Humana Press, Inc. 1993), Cotter (ed.), Molecular Diagnosis of Cancer (Humana Press, Inc. 1996), Hanausek and Walaszek (eds.), Tumor Marker Protocols (Humana Press, Inc. 1998), Lo (ed.), Clinical Applications of PCR (Humana Press, Inc. 1998), and Meltzer (ed.), PCR in Bioanalysis (Humana Press, Inc. 1998)).

PCR primers can be designed to amplify a portion of the Ztnfr12 gene that has a low sequence similarity to a comparable region in other proteins, such as other tumor necrosis factor receptor proteins.

One variation of PCR for diagnostic assays is reverse transcriptase-PCR (RT-PCR). In the RT-PCR technique, RNA is isolated from a biological sample, reverse transcribed to cDNA, and the cDNA is incubated with Ztnfr12 primers (see, for example, Wu et al. (eds.), "Rapid Isolation of Specific cDNAs or Genes by PCR," in Methods in Gene Biotechnology, pages 15-28 (CRC Press, Inc. 1997)). PCR is then performed and the products are analyzed using standard techniques.

As an illustration, RNA is isolated from biological sample using, for example, the guanidinium-thiocyanate cell lysis procedure described above. Alternatively, a solid-phase technique can be used to isolate mRNA from a cell lysate. A reverse transcription reaction can be primed with the isolated RNA using random oligonucleotides, short homopolymers of dT, or Ztnfr12 anti-sense oligomers. Oligo-dT primers offer the advantage that various mRNA nucleotide sequences are amplified that can provide control target sequences. Ztnfr12 sequences are amplified by the polymerase chain reaction using two flanking oligonucleotide primers that are typically 20 bases in length.

PCR amplification products can be detected using a variety of approaches. For example, PCR products can be fractionated by gel electrophoresis, and visualized by ethidium bromide staining. Alternatively, fractionated PCR products can be transferred to a membrane, hybridized with a detectably-labeled Ztnfr12 probe, and examined by autoradiography. Additional alternative approaches include the use of digoxigenin-labeled deoxyribonucleic acid triphosphates to provide chemiluminescence detection, and the C-TRAK calorimetric assay.

Another approach for detection of Ztnfr12 expression is cycling probe technology, in which a single-stranded DNA target binds with an excess of DNA-RNA-DNA chimeric probe to form a complex, the RNA portion is cleaved with RNAase H, and the presence of cleaved chimeric probe is detected (see, for example, Beggs et al., J. Clin. Microbiol. 34:2985 (1996), Bekkaoui et al., Biotechniques 20:240 (1996)). Alternative methods for detection of Ztnfr12 sequences can utilize approaches such as nucleic acid sequence-based amplification, cooperative amplification of templates by cross-hybridization, and the ligase chain reaction (see, for example, Marshall et al., U.S. Pat. No. 5,686,272 (1997), Dyer et al., J. Virol. Methods 60:161 (1996), Ehricht et al., Eur. J. Biochem. 243:358 (1997), and Chadwick et al., J. Virol. Methods 70:59 (1998)). Other standard methods are known to those of skill in the art.

Ztnfr12 probes and primers can also be used to detect and to localize Ztnfr12 gene expression in tissue samples. Methods for such in situ hybridization are well-known to those of skill in the art (see, for example, Choo (ed.), In Situ Hybridization Protocols (Humana Press, Inc. 1994), Wu et al. (eds.), "Analysis of Cellular DNA or Abundance of mRNA by Radioactive In Situ Hybridization (RISH)," in Methods in Gene Biotechnology, pages 259-278 (CRC Press, Inc. 1997), and Wu et al. (eds.), "Localization of DNA or Abundance of mRNA by Fluorescence In Situ Hybridization (RISH)," in Methods in Gene Biotechnology, pages 279-289 (CRC Press, Inc. 1997)). Various additional diagnostic approaches are well-known to those of skill in the art (see, for example, Mathew (ed.), Protocols in Human Molecular Genetics (Humana Press, Inc. 1991), Coleman and Tsongalis, Molecular Diagnostics (Humana Press, Inc. 1996), and Elles, Molecular Diagnosis of Genetic Diseases (Humana Press, Inc., 1996)). Suitable test samples include blood, urine, saliva, tissue biopsy, and autopsy material.

The Ztnfr12 gene resides in chromosome 22q13.2, a region that is associated with diseases and disorders, such as Fechtner syndrome, Sorsby fundus dystrophy, deafness, and neutrophil immunodeficiency syndrome. In addition, mutations of cytokine receptors are associated with particular diseases. For example, polymorphisms of cytokine receptors are associated with pulmonary alveolar proteinosis, familial periodic fever, and erythroleukemia. Thus, Ztnfr12 nucleotide sequences can be used in linkage-based testing for various diseases, and to determine whether a subject's chromosomes contain a mutation in the Ztnfr12 gene. Detectable chromosomal aberrations at the Ztnfr12 gene locus include, but are not limited to, aneuploidy, gene copy number changes, insertions, deletions, restriction site changes and rearrangements. Of particular interest are genetic alterations that inactivate a Ztnfr12 gene.

Aberrations associated with the Ztnfr12 locus can be detected using nucleic acid molecules of the present invention by employing molecular genetic techniques, such as restriction fragment length polymorphism analysis, short tandem repeat analysis employing PCR techniques, amplification-refractory mutation system analysis, single-strand conformation polymorphism detection, RNase cleavage methods, denaturing gradient gel electrophoresis, fluorescence-assisted mismatch analysis, and other genetic analysis techniques known in the art (see, for example, Mathew (ed.), Protocols in Human Molecular Genetics (Humana Press, Inc. 1991), Marian, Chest 108:255 (1995), Coleman and Tsongalis, Molecular Diagnostics (Human Press, Inc. 1996), Elles (ed.) Molecular Diagnosis of Genetic Diseases (Humana Press, Inc. 1996), Landegren (ed.), Laboratory Protocols for Mutation Detection (Oxford University Press 1996), Birren et al. (eds.), Genome Analysis, Vol. 2: Detecting Genes (Cold Spring Harbor Laboratory Press 1998), Dracopoli et al. (eds.), Current Protocols in Human Genetics (John Wiley & Sons 1998), and Richards and Ward, "Molecular Diagnostic Testing," in Principles of Molecular Medicine, pages 83-88 (Humana Press, Inc. 1998)).

As an illustration, large deletions in a Ztnfr12 gene can be detected using Southern hybridization analysis or PCR amplification. Deletions in a particular Ztnfr12 exon can be detected using PCR primers that flank the exon. Table 1 provides the locations of Ztnfr12 exons present in the nucleotide sequences of SEQ ID NOs:1 and 9. This information can be used to design primers that amplify particular exons.

Mutations can also be detected by hybridizing an oligonucleotide probe comprising a normal Ztnfr12 sequence to a Southern blot or to membrane-bound PCR products. Discrimination is achieved by hybridizing under conditions of high stringency, or by washing under varying conditions of stringency. This analysis can be targeted to a particular coding sequence. Alternatively, this approach is used to examine splice-donor or splice-acceptor sites in the immediate flanking intron sequences, where disease-causing mutations are often located. Suitable oligonucleotides can be designed by extending the sequence into an exon of choice, using the information provided in Table 1 and SEQ ID NOs:1 and 9.

The duplication of all or part of a gene can cause a disorder when the insertion of the duplicated material is inserted into the reading frame of a gene and causes premature termination of translation. Duplication and insertion can be examined directly by analyzing a subject's genomic DNA with standard methods, such as Southern hybridization, fluorescence in situ hybridization, pulsed-field gel analysis, or PCR. In addition, the effect of duplication can be detected with the protein truncation assay described below.

A point mutation can lead to a nonconservative change resulting in the alteration of Ztnfr12 function or a change of an amino acid codon to a stop codon. If a point mutation occurs within an intron, the mutation may affect the fidelity of splicing. A point mutation can be detected using standard techniques, such as Southern hybridization analysis, PCR analysis, sequencing, ligation chain reaction, and other approaches. In single-strand conformation polymorphism analysis, for example, fragments amplified by PCR are separated into single strands and fractionated by polyacrylamide gel electrophoresis under denaturing conditions. The rate of migration through the gel is a function of conformation, which depends upon the base sequence. A mutation can alter the rate of migration of one or both single strands. In a chemical cleavage approach, hybrid molecules are produced between test and control DNA (e.g., DNA that encodes the amino acid sequence of SEQ ID NO:2). Sites of base pair mismatch due to a mutation will be mispaired, and the strands will be susceptible to chemical cleavage at these sites.

The protein truncation test is also useful for detecting the inactivation of a gene in which translation-terminating mutations produce only portions of the encoded protein (see, for example, Stoppa-Lyonnet et al., Blood 91:3920 (1998)). According to this approach, RNA is isolated from a biological sample, and used to synthesize cDNA. PCR is then used to amplify the Ztnfr12 target sequence and to introduce an RNA polymerase promoter, a translation initiation sequence, and an in-frame ATG triplet. PCR products are transcribed using an RNA polymerase, and the transcripts are translated in vitro with a T7-coupled reticulocyte lysate system. The translation products are then fractionated by SDS-PAGE to determine the lengths of the translation products. The protein truncation test is described, for example, by Dracopoli et al. (eds.), Current Protocols in Human Genetics, pages 9.11.1-9.11.18 (John Wiley & Sons 1998).

In an alternative approach, a mutation can be detected using ribonuclease A, which will cleave the RNA strand of an RNA-DNA hybrid at the site of a sequence mismatch. Briefly, a PCR-amplified sequence of a Ztnfr12 gene or cDNA of a subject is hybridized with in vitro transcribed labeled RNA probes prepared from the DNA of a normal, healthy individual chosen from the general population. The RNA-DNA hybrids are digested with ribonuclease A and analyzed using denaturing gel electrophoresis. Sequence mismatches between the two strands will cause cleavage of the protected fragment, and small additional fragments will be detected in the samples derived from a subject who has a mutated Ztnfr12 gene. The site of mutation can be deduced from the sizes of the cleavage products.

Analysis of chromosomal DNA using the Ztnfr12 polynucleotide sequence is useful for correlating disease with abnormalities localized to chromosome 22q, in particular to chromosome 22q13.2. In one embodiment, the methods of the present invention provide a method of detecting a chromosome 22q13.2 abnormality in a sample from an individual comprising: (a) obtaining Ztnfr12 RNA from the sample, (b) generating Ztnfr12 cDNA by polymerase chain reaction, and (c) comparing the nucleotide sequence of the Ztnfr12 cDNA to the nucleic acid sequence as shown in SEQ ID NO:1. In further embodiments, the difference between the sequence of the Ztnfr12cDNA or Ztnfr12 gene in the sample and the Ztnfr12 sequence as shown in SEQ ID NOs:1 or 9 is indicative of chromosome 22q13.2 abnormality.

In another embodiment, the present invention provides methods for detecting in a sample from an individual, a chromosome 22q13.2 abnormality associated with an alteration in ZTNF4 activity, comprising the steps of: (a) contacting nucleic acid molecules of the sample with a nucleic acid probe that hybridizes with a nucleic acid molecule consisting of the nucleotide sequence of SEQ ID NO:1, its complements or fragments, under stringent conditions, and (b) detecting the presence or absence of hybridization of the probe with nucleic acid molecules in the sample, wherein the absence of hybridization is indicative of a chromosome 22q13.2 abnormality, such as an abnormality that causes a decrease in response to ZTNF4.

The present invention also provides methods of detecting in a sample from an individual, a Ztnfr12 gene abnormality associated with an alteration in ZTNF4 activity, comprising: (a) isolating nucleic acid molecules that encode Ztnfr12 from the sample, and (b) comparing the nucleotide sequence of the isolated Ztnfr12-encoding sequence with the nucleotide sequence of SEQ ID NO:1, wherein the difference between the sequence of the isolated Ztnfr12-encoding sequence or a polynucleotide encoding the Ztnfr12 polypeptide generated from the isolated Ztnfr12-encoding sequence and the nucleotide sequence of SEQ ID NO:1 is indicative of an Ztnfr12 gene abnormality associated with disease or susceptibility to a disease in an individual, such as an abnormality that causes a decrease in response to ZTNF4.

The present invention also provides methods of detecting in a sample from a individual, an abnormality in expression of the Ztnfr12 gene associated with disease or susceptibility to disease, comprising: (a) obtaining Ztnfr12 RNA from the sample, (b) generating Ztnfr12 cDNA by polymerase chain reaction from the Ztnfr12 RNA, and (c) comparing the nucleotide sequence of the Ztnfr12 cDNA to the nucleotide sequence of SEQ ID NO:1, wherein a difference between the sequence of the Ztnfr12 cDNA and the nucleotide sequence of SEQ ID NO:1 is indicative of an abnormality in expression of the ZTNFR12 gene associated with disease or susceptibility to disease.

In other aspects, the present invention provides methods for detecting in a sample from an individual, a Ztnfr12 gene abnormality, comprising: (a) contacting sample nucleic acid molecules with a nucleic acid probe, wherein the probe hybridizes to a nucleic acid molecule having the nucleotide sequence of SEQ ID NO:1, its complements or fragments, under stringent conditions, and (b) detecting the presence or absence of hybridization is indicative of a Ztnfr12 abnormality.

In situ hybridization provides another approach for identifying Ztnfr12 gene abnormalities. According to this approach, a Ztnfr12 probe is labeled with a detectable marker by any method known in the art. For example, the probe can be directly labeled by random priming, end labeling, PCR, or nick translation. Suitable direct labels include radioactive labels such as $^{32}P$, $^{3}H$, and $^{35}S$ and non-radioactive labels such as fluorescent markers (e.g., fluorescein, Texas Red, AMCA blue (7-amino-4-methyl-coumanine-3-acetate), lucifer yellow, rhodamine, etc.), cyanin dyes, which are detectable with visible light, enzymes, and the like. Probes labeled with an enzyme can be detected through a colorimetric reaction by providing a substrate for the enzyme. In the presence of various substrates, different colors are produced by the reaction, and these colors can be visualized to separately detect multiple probes if desired. Suitable substrates for alkaline phosphatase include 5-bromo-4-chloro-3-indolylphosphate and nitro blue tetrazolium. One suitable substrate for horseradish peroxidase is diaminobenzoate.

An illustrative method for detecting chromosomal abnormalities with in situ hybridization is described by Wang et al., U.S. Pat. No. 5,856,089. Following this approach, for example, a method of performing in situ hybridization with a Ztnfr12 probe to detect a chromosome structural abnormality in a cell from a fixed tissue sample obtained from a subject can comprise the steps of: (1) obtaining a fixed tissue sample from the patient, (2) pretreating the fixed tissue sample obtained in step (1) with a bisulfite ion composition, (3) digesting the fixed tissue sample with proteinase, (4) performing in situ hybridization on cells obtained from the digested fixed tissue sample of step (3) with a probe which specifically hybridizes to the Ztnfr12 gene, wherein a signal pattern of hybridized probes is obtained, (5) comparing the signal pattern of the hybridized probe in step (4) to a predetermined signal pattern of the hybridized probe obtained when performing in situ hybridization on cells having a normal critical chromosome region of interest, and (6) detecting a chromosome structural abnormality in the patient's cells, by detecting a difference between the signal pattern obtained in step (4) and the predetermined signal pattern. Examples of Ztnfr12 gene abnormalities include deletions, amplifications, translocations, inversions, and the like. Such an assay may be used, for example, to test tissue from a subject suspected of having disease or disorder associated with altered responsiveness to ZTNF4.

The present invention contemplates kits for performing a diagnostic assay for Ztnfr12 gene expression or to detect mutations in the Ztnfr12 gene. Such kits comprise nucleic acid probes, such as double-stranded nucleic acid molecules comprising the nucleotide sequence of nucleotides 27 to 578 of SEQ ID NO:1, nucleotides 27 to 233 of SEQ ID NO:1, or a portion thereof, as well as single-stranded nucleic acid molecules having the complement of the nucleotide sequence of nucleotides 27 to 578 of SEQ ID NO:1, nucleotides 27 to 233 of SEQ ID NO:1, or a portion thereof. Probe molecules may be DNA, RNA, oligonucleotides, and the like. Kits may comprise nucleic acid primers for performing PCR.

Such kits can contain all the necessary elements to perform a nucleic acid diagnostic assay described above. A kit will comprise at least one container comprising a Ztnfr12 probe or primer. The kit may also comprise a second container comprising one or more reagents capable of indicating the presence of Ztnfr12 sequences. Examples of such indicator reagents include detectable labels such as radioactive labels, fluorochromes, chemiluminescent agents, and the like. A kit may also comprise a means for conveying to the user that the Ztnfr12 probes and primers are used to detect Ztnfr12 gene expression. For example, written instructions may state that the enclosed nucleic acid molecules can be used to detect either a nucleic acid molecule that encodes Ztnfr12, or a nucleic acid molecule having a nucleotide sequence that is complementary to a Ztnfr12-encoding nucleotide sequence. The written material can be applied directly to a container, or the written material can be provided in the form of a packaging insert.

11. Use of Anti-Ztnfr12 Antibodies to Detect Ztnfr12

The present invention contemplates the use of anti-Ztnfr12 antibodies to screen biological samples in vitro for the presence of Ztnfr12. In one type of in vitro assay, anti-Ztnfr12 antibodies are used in liquid phase. For example, the presence of Ztnfr12 in a biological sample can be tested by mixing the biological sample with a trace amount of labeled Ztnfr12 and an anti-Ztnfr12 antibody under conditions that promote binding between Ztnfr12 and its antibody. Complexes of Ztnfr12 and anti-Ztnfr12 in the sample can be separated from the reaction mixture by contacting the complex with an immobilized protein which binds with the antibody, such as an Fc antibody or *Staphylococcus* protein A. The concentration of Ztnfr12 in the biological sample will be inversely proportional to the amount of labeled Ztnfr12 bound to the antibody and directly related to the amount of free-labeled Ztnfr12.

Illustrative biological samples include blood, urine, saliva, tissue biopsy, and autopsy material.

Alternatively, in vitro assays can be performed in which anti-Ztnfr12 antibody is bound to a solid-phase carrier. For example, antibody can be attached to a polymer, such as aminodextran, in order to link the antibody to an insoluble support such as a polymer-coated bead, a plate or a tube. Other suitable in vitro assays will be readily apparent to those of skill in the art.

In another approach, anti-Ztnfr12 antibodies can be used to detect Ztnfr12 in tissue sections prepared from a biopsy specimen. Such immunochemical detection can be used to determine the relative abundance of Ztnfr12 and to determine the distribution of Ztnfr12 in the examined tissue. General immunochemistry techniques are well established (see, for example, Ponder, "Cell Marking Techniques and Their Application," in Mammalian Development: A Practical Approach, Monk (ed.), pages 115-38 (IRL Press 1987), Coligan at pages 5.8.1-5.8.8, Ausubel (1995) at pages 14.6.1 to 14.6.13 (Wiley Interscience 1990), and Manson (ed.), Methods In Molecular Biology, Vol. 10: Immunochemical Protocols (The Humana Press, Inc. 1992)).

Immunochemical detection can be performed by contacting a biological sample with an anti-Ztnfr12 antibody, and then contacting the biological sample with a detectably labeled molecule, which binds to the antibody. For example, the detectably labeled molecule can comprise an antibody moiety that binds to anti-Ztnfr12 antibody. Alternatively, the anti-Ztnfr12 antibody can be conjugated with avidin/streptavidin (or biotin) and the detectably labeled molecule can comprise biotin (or avidin/streptavidin). Numerous variations of this basic technique are well-known to those of skill in the art.

Alternatively, an anti-Ztnfr12 antibody can be conjugated with a detectable label to form an anti-Ztnfr12 immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3$H, $^{125}$I, 131I, $^{35}$S and $^{14}$C.

Anti-Ztnfr12 immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-Ztnfr12 immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-Ztnfr12 immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-Ztnfr12 immunoconjugates can be detectably labeled by linking an anti-Ztnfr12 antibody component to an enzyme. When the anti-Ztnfr12-enzyme conjugate is incubated in the presence of the appropriate substrate, the enzyme moiety reacts with the substrate to produce a chemical moiety, which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels, which can be employed in accordance with the present invention. The binding of marker moieties to anti-Ztnfr12 antibodies can be accomplished using standard techniques known to the art. Typical methodology in this regard is described by Kennedy et al., Clin. Chim. Acta 70:1 (1976), Schurs et al., Clin. Chim. Acta 81:1 (1977), Shih et al., Int'l J. Cancer 46:1101 (1990), Stein et al., Cancer Res. 50:1330 (1990), and Coligan, supra.

Moreover, the convenience and versatility of immunochemical detection can be enhanced by using anti-Ztnfr12 antibodies that have been conjugated with avidin, streptavidin, and biotin (see, for example, Wilchek et al. (eds.), "Avidin-Biotin Technology," Methods In Enzymology, Vol. 184 (Academic Press 1990), and Bayer et al., "Immunochemical Applications of Avidin-Biotin Technology," in Methods In Molecular Biology, Vol. 10, Manson (ed.), pages 149-162 (The Humana Press, Inc. 1992).

Methods for performing immunoassays are well-established. See, for example, Cook and Self, "Monoclonal Antibodies in Diagnostic Immunoassays," in Monoclonal Antibodies: Production, Engineering, and Clinical Application, Ritter and Ladyman (eds.), pages 180-208, (Cambridge University Press, 1995), Perry, "The Role of Monoclonal Antibodies in the Advancement of Immunoassay Technology," in Monoclonal Antibodies: Principles and Applications, Birch and Lennox (eds.), pages 107-120 (Wiley-Liss, Inc. 1995), and Diamandis, Immunoassay (Academic Press, Inc. 1996).

The present invention also contemplates kits for performing an immunological diagnostic assay for Ztnfr12 gene expression. Such kits comprise at least one container comprising an anti-Ztnfr12 antibody, or antibody fragment. A kit may also comprise a second container comprising one or more reagents capable of indicating the presence of Ztnfr12 antibody or antibody fragments. Examples of such indicator reagents include detectable labels such as a radioactive label, a fluorescent label, a chemiluminescent label, an enzyme label, a bioluminescent label, colloidal gold, and the like. A kit may also comprise a means for conveying to the user that Ztnfr12 antibodies or antibody fragments are used to detect Ztnfr12 protein. For example, written instructions may state that the enclosed antibody or antibody fragment can be used to detect Ztnfr12. The written material can be applied directly to a container, or the written material can be provided in the form of a packaging insert.

12. Therapeutic Uses of Polypeptides Having Ztnfr12 Activity

Amino acid sequences having Ztnfr12 activity can be used to modulate the immune system by binding a Ztnfr12 ligand (e.g., ZTNF4), and thus, preventing the binding of the Ztnfr12 ligand with endogenous Ztnfr12 receptor. Accordingly, the present invention includes the use of proteins, polypeptides, and peptides having Ztnfr12 activity (such as Ztnfr12 polypeptides, Ztnfr12 analogs (e.g., anti-Ztnfr12 anti-idiotype antibodies), and Ztnfr12 fusion proteins) to a subject which lacks an adequate amount of Ztnfr12 polypeptide, or which produces an excess of ZTNF4. Ztnfr12 antagonists (e.g., anti-Ztnfr12 antibodies) can be also used to treat a subject, which produces an excess of either ZTNF4 or Ztnfr12. These molecules can be administered to any subject in need of treatment, and the present invention contemplates both veterinary and human therapeutic uses. Illustrative subjects include mammalian subjects, such as farm animals, domestic animals, and human patients. Human or murine Ztnfr12 polypeptides can be used for these applications.

Molecules having Ztnfr12 activity can be used for the treatment of autoimmune diseases, B cell cancers, immunomodulation, IBD and any antibody-mediated pathologies (e.g., ITCP, myasthenia gravis and the like), renal diseases, indirect T cell immune response, graft rejection, and graft versus host disease. The polypeptides of the present invention can be targeted to specifically regulate B cell responses during the immune response. Additionally, the polypeptides of the present invention can be used to modulate B cell development, development of other cells, antibody production, and cytokine production. Polypeptides of the present invention can also modulate T and B cell communication by neutralizing the proliferative effects of ZTNF4.

Ztnfr12 polypeptides of the present invention can be useful to neutralize the effects of ZTNF4 for treating pre-B or B-cell leukemias, such as plasma cell leukemia, chronic or acute lymphocytic leukemia, myelomas such as multiple myeloma, plasma cell myeloma, endothelial myeloma and giant cell myeloma, and lymphomas such as non-Hodgkins lymphoma, for which an increase in ZTNF4 polypeptides is associated. Additional examples of B cell lymphomas that may be treated with the molecules described herein include Burkitt's lymphoma, Non-Burkiff's lymphoma, follicular lymphoma, acute lymphoblastic leukemia, large cell lymphoma, marginal zone lymphoma, mantle cell lymphoma, large cell lymphoma (e.g., immunoblastic lymphoma), small lymphocytic lymphoma, and other B cell lymphomas.

ZTNF4 is expressed in $CD8^+$ cells, monocytes, dendritic cells, activated monocytes, which indicates that, in certain autoimmune disorders, cytotoxic T-cells might stimulate B-cell production through excess production of ZTNF4. Immunosuppressant proteins that selectively block the action of B-lymphocytes would be of use in treating disease. Autoantibody production is common to several autoimmune diseases and contributes to tissue destruction and exacerbation of disease. Autoantibodies can also lead to the occurrence of immune complex deposition complications and lead to many symptoms of systemic lupus erythomatosis, including kidney failure, neuralgic symptoms and death. Modulating antibody production independent of cellular response would also be beneficial in many disease states. B cells have also been shown to play a role in the secretion of arthritogenic immunoglobulins in rheumatoid arthritis. As such, inhibition of ZTNF4-stimulated antibody production would be beneficial in treatment of autoimmune diseases such as myasthenia gravis and rheumatoid arthritis. Immunosuppressant therapeutics such as soluble Ztnfr12 that selectively block or neutralize the action of B-lymphocytes would be useful for such purposes.

The invention provides methods employing Ztnfr12 polypeptides, fusions, antibodies, agonists or antagonists for selectively blocking or neutralizing the actions of B-cells in association with end stage renal diseases, which may or may not be associated with autoimmune diseases. Such methods would also be useful for treating immunologic renal diseases. Such methods would be would be useful for treating glomerulonephritis associated with diseases such as membranous nephropathy, IgA nephropathy or Berger's Disease, IgM nephropathy, Goodpasture's Disease, post-infectious glomerulonephritis, mesangioproliferative disease, chronic lymphoid leukemia, minimal-change nephrotic syndrome. Such methods would also serve as therapeutic applications for treating secondary glomerulonephritis or vasculitis associated with such diseases as lupus, polyarteritis, Henoch-Schonlein, Scleroderma, HIV-related diseases, amyloidosis or hemolytic uremic syndrome. The methods of the present invention would also be useful as part of a therapeutic application for treating interstitial nephritis or pyelonephritis associated with chronic pyelonephritis, analgesic abuse, nephrocalcinosis, nephropathy caused by other agents, nephrolithiasis, or chronic or acute interstitial nephritis.

The methods of the present invention also include use of Ztnfr12 polypeptides, fusions, antibodies, agonists or antagonists in the treatment of hypertensive or large vessel diseases, including renal artery stenosis or occlusion and cholesterol emboli or renal emboli.

The present invention also provides methods for treatment of renal or urological neoplasms, multiple myelomas, lymphomas, light chain neuropathy or amyloidosis.

The invention also provides methods for blocking or inhibiting activated B cells using Ztnfr12 polypeptides, fusions, antibodies, agonists or antagonists for the treatment of asthma and other chronic airway diseases such as bronchitis and emphysema.

Also provided are methods for inhibiting or neutralizing an effector T cell response using Ztnfr12 polypeptides, fusions, antibodies, agonists or antagonists for use in immunosuppression, in particular for such therapeutic use as for graft-versus-host disease and graft rejection. Moreover, Ztnfr12 polypeptides, fusions, antibodies, agonists or antagonists would be useful in therapeutic protocols for treatment of such autoimmune diseases as insulin dependent diabetes mellitus (IDDM) and Crohn's Disease. Methods of the present invention would have additional therapeutic value for treating chronic inflammatory diseases, in particular to lessen joint pain, swelling, anemia and other associated symptoms as well as treating septic shock.

Compounds identified as Ztnfr12 agonists are also useful to boost the humoral immune response. B cell responses are important in fighting infectious diseases including bacterial, viral, protozoan and parasitic infections. Antibodies against infectious microorganisms can immobilize the pathogen by binding to antigen followed by complement mediated lysis or cell mediated attack. A Ztnfr12 agonist would serve to boost the humoral response and would be a useful therapeutic for individuals at risk for an infectious disease, an immunocompromised state, or as a supplement to vaccination.

Well established animal models are available to test in vivo efficacy of soluble Ztnfr12 polypeptides of the present invention in certain disease states. In particular, soluble Ztnfr12 polypeptides and polypeptide fragments can be tested in vivo in a number of animal models of autoimmune disease, such as MRL-lpr/lpr or NZB×NZW F1 congenic mouse strains which serve as a model of SLE (systemic lupus erythematosus). Such animal models are known in the art, and illustrative models are described above, including NZBW mice that develop a spontaneous form of SLE, murine models for experimental allergic encephalomyelitis, the collagen-induced arthritis murine model, murine experimental autoimmune myasthenia gravis, and the like.

Generally, the dosage of administered Ztnfr12 (or Ztnfr12 analog or fusion protein) will vary depending upon such factors as the subject's age, weight, height, sex, general medical condition and previous medical history. Typically, it is desirable to provide the recipient with a dosage of Ztnfr12 polypeptide, which is in the range of from about 1 pg/kg to 10 mg/kg (amount of agent/body weight of subject), although a lower or higher dosage also may be administered as circumstances dictate.

Administration of a Ztnfr12 polypeptide to a subject can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in Protein Delivery: Physical Systems, Sanders and Hendren (eds.), pages 255-288 (Plenum Press 1997)). The feasibility of an intranasal delivery is exemplified by such a mode of insulin administration (see, for example, Hinchcliffe and Illum, Adv. Drug Deliv. Rev. 35:199 (1999)). Dry or liquid particles comprising Ztnfr12 can be prepared and inhaled with the aid of dry-powder dispersers, liquid aerosol generators, or nebulizers (e.g., Pettit and Gombotz, TIBTECH 16:343 (1998); Patton et al., Adv. Drug Deliv. Rev. 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al., Science 269:850 (1995)). Transdermal delivery using electroporation provides another means to administer a molecule having Ztnfr12 binding activity (Potts et al., Pharm. Biotechnol. 10:213 (1997)).

A pharmaceutical composition comprising a protein, polypeptide, or peptide having Ztnfr12 binding activity can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), Remington's Pharmaceutical Sciences, 19th Edition (Mack Publishing Company 1995).

For purposes of therapy, molecules having Ztnfr12 binding activity and a pharmaceutically acceptable carrier are administered to a patient in a therapeutically effective amount. A combination of a protein, polypeptide, or peptide having Ztnfr12 binding activity and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates the inflammatory response. As another example, an agent used to inhibit the growth of tumor cells is physiologically significant if the administration of the agent results in a decrease in the number of tumor cells, decreased metastasis, a decrease in the size of a solid tumor, or increased necrosis of a tumor.

A pharmaceutical composition comprising Ztnfr12 (or Ztnfr12 analog or fusion protein) can be furnished in liquid form, in an aerosol, or in solid form. Liquid forms, are illustrated by injectable solutions and oral suspensions. Exemplary solid forms include capsules, tablets, and controlled-release forms. The latter form is illustrated by miniosmotic pumps and implants (Bremer et al., Pharm. Biotechnol. 10:239 (1997); Ranade, "Implants in Drug Delivery," in Drug Delivery Systems, Ranade and Hollinger (eds.), pages 95-123 (CRC Press 1995); Bremer et al., "Protein Delivery with Infusion Pumps," in Protein Delivery: Physical Systems, Sanders and Hendren (eds.), pages 239-254 (Plenum Press 1997); Yewey et al., "Delivery of Proteins from a Controlled Release Injectable Implant," in Protein Delivery: Physical Systems, Sanders and Hendren (eds.), pages 93-117 (Plenum Press 1997)).

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., Eur. J. Clin. Microbiol. Infect. Dis. 12 (Suppl. 1):S61 (1993), Kim, Drugs 46:618 (1993), and Ranade, "Site-Specific Drug Delivery Using Liposomes as Carriers," in Drug Delivery Systems, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s) (see, for example, Machy et al., Liposomes In Cell Biology And Pharmacology (John Libbey 1987), and Ostro et al., American J. Hosp. Pharm. 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., Ann. N.Y. Acad. Sci. 446:368 (1985)). After intravenous administration, small liposomes (0.1 to 1.0 μm) are typically taken up by cells of the reticuloendothelial system, located principally in the liver and spleen, whereas liposomes larger than 3.0 μm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., Biochim. Biophys. Acta 802:428 (1984)). In addition, incorporation of glycolipid- or polyethelene glycol-derivatized phospholipids into liposome membranes has been shown to result in a significantly reduced uptake by the reticuloendothelial system (Allen et al., Biochim. Biophys. Acta 1068:133 (1991); Allen et al., Biochim. Biophys. Acta 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., Biol. Pharm. Bull. 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., Biol. Pharm. Bull. 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, Crit. Rev. Ther. Drug Carrier Syst. 14:287 (1997); Murahashi et al., Biol. Pharm. Bull. 20:259 (1997)). Similarly, Wu et al., Hepatology 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., Biol. Pharm. Bull. 20:259 (1997)). Polyaconitylated human serum albumin liposomes provide another approach for targeting liposomes to liver cells (Kamps et al., Proc. Nat'l Acad. Sci. USA 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver. In addition, anti-Ztnfr12 antibody components can be used to direct liposomes to Ztnfr12-expressing cells, such as tumor cells of B cell origin.

In a more general approach to tissue targeting, target cells are prelabeled with biotinylated antibodies specific for a ligand expressed by the target cell (Harasym et al., Adv. Drug Deliv. Rev. 32:99 (1998)). After plasma elimination of free antibody, streptavidin-conjugated liposomes are administered. In another approach, targeting antibodies are directly attached to liposomes (Harasym et al., Adv. Drug Deliv. Rev. 32:99 (1998)).

Polypeptides having Ztnfr12 binding activity can be encapsulated within liposomes using standard techniques of protein microencapsulation (see, for example, Anderson et al., Infect. Immun. 31:1099 (1981), Anderson et al., Cancer Res. 50:1853 (1990), and Cohen et al., Biochim. Biophys. Acta 1063:95 (1991), Alving et al. "Preparation and Use of Liposomes in Immunological Studies," in Liposome Technology, 2nd Edition, Vol. III, Gregoriadis (ed.), page 317 (CRC Press 1993), Wassef et al., Meth. Enzymol. 149:124 (1987)). As noted above, therapeutically useful liposomes may contain a variety of components. For example, liposomes may comprise lipid derivatives of poly(ethylene glycol) (Allen et al., Biochim. Biophys. Acta 1150:9 (1993)).

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, Bioconjugate Chem. 6:332 (1995); Ranade, "Role of Polymers in Drug Delivery," in Drug Delivery Systems, Ranade and Hollinger (eds.), pages 51-93 (CRC Press 1995); Roskos and Maskiewicz, "Degradable Controlled Release Systems Useful for Protein Delivery," in Protein Delivery: Physical Systems, Sanders and Hendren (eds.), pages 45-92 (Plenum Press 1997); Bartus et al., Science 281:1161 (1998); Putney and Burke, Nature Biotechnology 16:153 (1998); Putney, Curr. Opin. Chem. Biol. 2:548 (1998)). Polyethylene glycol (PEG)-coated nanospheres can also provide carriers for intravenous administration of therapeutic proteins (see, for example, Gref et al., Pharm. Biotechnol. 10:167 (1997)).

The present invention also contemplates chemically modified polypeptides having binding Ztnfr12 activity and Ztnfr12 antagonists, in which a polypeptide is linked with a polymer, as discussed above. In addition, the present invention contemplates compositions, such as pharmaceutical compositions, comprising a carrier, a Ztnfr12 polypeptide, and at least one of a BCMA polypeptide and a TACI polypeptide, as discussed above.

Other dosage forms can be devised by those skilled in the art, as shown, for example, by Ansel and Popovich, Pharmaceutical Dosage Forms and Drug Delivery Systems, $5^{th}$ Edition (Lea & Febiger 1990), Gennaro (ed.), Remington's Pharmaceutical Sciences, $19^{th}$ Edition (Mack Publishing Company 1995), and by Ranade and Hollinger, Drug Delivery Systems (CRC Press 1996).

As an illustration, pharmaceutical compositions may be supplied as a kit comprising a container that comprises a polypeptide with a Ztnfr12 extracellular domain or a Ztnfr12 antagonist (e.g., an antibody or antibody fragment that binds a Ztnfr12 polypeptide). Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition. Moreover, such information may include a statement that the Ztnfr12 composition is contraindicated in patients with known hypersensitivity to Ztnfr12.

13. Therapeutic Uses of Ztnfr12 Nucleotide Sequences

The present invention includes the use of Ztnfr12 nucleotide sequences to provide Ztnfr12 to a subject in need of such treatment. An enhancement in Ztnfr12 activity can be useful as part of a treatment of immunosuppressive diseases. In addition, a therapeutic expression vector can be provided that inhibits Ztnfr12 gene expression, such as an anti-sense molecule, a ribozyme, or an external guide sequence molecule. Inhibition of ZTNF4 activity can be achieved by introducing an expression vector that encodes a form of the Ztnfr12 receptor that either does not bind ZTNF4, or does not produce a signal following binding with ZTNF4 (e.g., due to a mutation in the Ztnfr12 intracellular domain). For veterinary therapeutic use or human therapeutic use, such nucleic acid molecules can be administered to a subject having a disorder or disease, as discussed above. As one example discussed earlier, nucleic acid molecules encoding a Ztnfr12-immunoglobulin fusion protein can be used for long-term treatment of systemic lupus erythematosus.

There are numerous approaches to introduce a Ztnfr12 gene to a subject, including the use of recombinant host cells that express Ztnfr12, delivery of naked nucleic acid encoding Ztnfr12, use of a cationic lipid carrier with a nucleic acid molecule that encodes Ztnfr12, and the use of viruses that express Ztnfr12, such as recombinant retroviruses, recombinant adeno-associated viruses, recombinant adenoviruses, and recombinant Herpes simplex viruses (see, for example, Mulligan, Science 260:926 (1993), Rosenberg et al., Science 242:1575 (1988), LaSalle et al., Science 259:988 (1993), Wolff et al., Science 247:1465 (1990), Breakfield and Deluca, The New Biologist 3:203 (1991)). In an ex vivo approach, for example, cells are isolated from a subject, transfected with a vector that expresses a Ztnfr12 gene, and then transplanted into the subject.

In order to effect expression of a Ztnfr12 gene, an expression vector is constructed in which a nucleotide sequence encoding a Ztnfr12 gene is operably linked to a core promoter, and optionally a regulatory element, to control gene transcription. The general requirements of an expression vector are described above.

Alternatively, a Ztnfr12 gene can be delivered using recombinant viral vectors, including for example, adenoviral vectors (e.g., Kass-Eisler et al., Proc. Nat'l Acad. Sci. USA 90:11498 (1993), Kolls et al., Proc. Nat'l Acad. Sci. USA 91:215 (1994), Li et al., Hum. Gene Ther. 4:403 (1993), Vincent et al., Nat. Genet. 5:130 (1993), and Zabner et al., Cell 75:207 (1993)), adenovirus-associated viral vectors (Flotte et al., Proc. Nat'l Acad. Sci. USA 90:10613 (1993)), alphaviruses such as Semliki Forest Virus and Sindbis Virus (Hertz and Huang, J. Vir. 66:857 (1992), Raju and Huang, J. Vir. 65:2501 (1991), and Xiong et al., Science 243:1188 (1989)), herpes viral vectors (e.g., U.S. Pat. Nos. 4,769,331, 4,859,587, 5,288,641 and 5,328,688), parvovirus vectors (Koering et al., Hum. Gene Therap. 5:457 (1994)), pox virus vectors (Ozaki et al., Biochem. Biophys. Res. Comm. 193: 653 (1993), Panicali and Paoletti, Proc. Nat'l Acad. Sci. USA 79:4927 (1982)), pox viruses, such as canary pox virus or vaccinia virus (Fisher-Hoch et al., Proc. Nat'l Acad. Sci. USA 86:317 (1989), and Flexner et al., Ann. N.Y. Acad. Sci. 569:86 (1989)), and retroviruses (e.g., Baba et al., J. Neurosurg 79:729 (1993), Ram et al., Cancer Res. 53:83 (1993), Takamiya et al., J. Neurosci. Res 33:493 (1992), Vile and Hart, Cancer Res. 53:962 (1993), Vile and Hart, Cancer Res. 53:3860 (1993), and Anderson et al., U.S. Pat. No. 5,399, 346). Within various embodiments, either the viral vector itself, or a viral particle which contains the viral vector may be utilized in the methods and compositions described below.

As an illustration of one system, adenovirus, a double-stranded DNA virus, is a well-characterized gene transfer vector for delivery of a heterologous nucleic acid molecule (for a review, see Becker et al., Meth. Cell Biol. 43:161 (1994); Douglas and Curiel, Science & Medicine 4:44 (1997)). The adenovirus system offers several advantages including: (i) the ability to accommodate relatively large DNA inserts, (ii) the ability to be grown to high-titer, (iii) the ability to infect a broad range of mammalian cell types, and (iv) the ability to be used with many different promoters including ubiquitous, tissue specific, and regulatable promoters. In addition, adenoviruses can be administered by intravenous injection, because the viruses are stable in the bloodstream.

Using adenovirus vectors where portions of the adenovirus genome are deleted, inserts are incorporated into the viral DNA by direct ligation or by homologous recombination with a co-transfected plasmid. In an exemplary system, the essential E1 gene is deleted from the viral vector, and the virus will not replicate unless the E1 gene is provided by the host cell. When intravenously administered to intact animals, adenovirus primarily targets the liver. Although an adenoviral delivery system with an E1 gene deletion cannot replicate in the host cells, the host's tissue will express and process an encoded heterologous protein. Host cells will also secrete the heterologous protein if the corresponding gene includes a secretory signal sequence. Secreted proteins will enter the circulation from tissue that expresses the heterologous gene (e.g., the highly vascularized liver).

Moreover, adenoviral vectors containing various deletions of viral genes can be used to reduce or eliminate immune responses to the vector. Such adenoviruses are E1-deleted, and in addition, contain deletions of E2A or E4 (Lusky et al., J. Virol. 72:2022 (1998); Raper et al., Human Gene Therapy 9:671 (1998)). The deletion of E2b has also been reported to reduce immune responses (Amalfitano et al., J. Virol. 72:926 (1998)). By deleting the entire adenovirus genome, very large inserts of heterologous DNA can be accommodated. The generation of so called "gutless" adenoviruses, where all viral genes are deleted, is particularly advantageous for insertion of large inserts of heterologous DNA (for a review, see Yeh. and Perricaudet, FASEB J. 11:615 (1997)).

High titer stocks of recombinant viruses capable of expressing a therapeutic gene can be obtained from infected mammalian cells using standard methods. For example, recombinant herpes simplex virus can be prepared in Vero cells, as described by Brandt et al., J. Gen. Virol. 72:2043 (1991), Herold et al., J. Gen. Virol. 75:1211 (1994), Visalli and Brandt, Virology 185:419 (1991), Grau et al., Invest. Ophthalmol. Vis. Sci. 30:2474 (1989), Brandt et al., J. Virol. Meth. 36:209 (1992), and by Brown and MacLean (eds.), HSV Virus Protocols (Humana Press 1997).

Alternatively, an expression vector comprising a Ztnfr12 gene can be introduced into a subject's cells by lipofection in vivo using liposomes. Synthetic cationic lipids can be used to prepare liposomes for in vivo transfection of a gene encoding a marker (Felgner et al., Proc. Nat'l Acad. Sci. USA 84:7413 (1987); Mackey et al., Proc. Nat'l Acad. Sci. USA 85:8027 (1988)). The use of lipofection to introduce exogenous genes into specific organs in vivo has certain practical advantages. Liposomes can be used to direct transfection to particular cell types, which is particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

Electroporation is another alternative mode of administration. For example, Aihara and Miyazaki, Nature Biotechnology 16:867 (1998), have demonstrated the use of in vivo electroporation for gene transfer into muscle.

In an alternative approach to gene therapy, a therapeutic gene may encode a Ztnfr12 anti-sense RNA that inhibits the expression of Ztnfr12. Suitable sequences for anti-sense molecules can be derived from the nucleotide sequences of Ztnfr12 disclosed herein.

Alternatively, an expression vector can be constructed in which a regulatory element is operably linked to a nucleotide sequence that encodes a ribozyme. Ribozymes can be designed to express endonuclease activity that is directed to a certain target sequence in an mRNA molecule (see, for example, Draper and Macejak, U.S. Pat. No. 5,496,698, McSwiggen, U.S. Pat. No. 5,525,468, Chowrira and McSwiggen, U.S. Pat. No. 5,631,359, and Robertson and Goldberg, U.S. Pat. No. 5,225,337). In the context of the present invention, ribozymes include nucleotide sequences that bind with Ztnfr12 mRNA.

In another approach, expression vectors can be constructed in which a regulatory element directs the production of RNA transcripts capable of promoting RNase P-mediated cleavage of mRNA molecules that encode a Ztnfr12 gene. According to this approach, an external guide sequence can be constructed for directing the endogenous ribozyme, RNase P, to a particular species of intracellular mRNA, which is subsequently cleaved by the cellular ribozyme (see, for example, Altman et al., U.S. Pat. No. 5,168,053, Yuan et al., Science 263:1269 (1994), Pace et al., international publication No. WO 96/18733, George et al., international publication No. WO 96/21731, and Werner et al., international publication No. WO 97/33991). For example, the external guide sequence can comprise a ten to fifteen nucleotide sequence complementary to Ztnfr12 mRNA, and a 3'-NCCA nucleotide sequence, wherein N is preferably a purine. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region.

In general, the dosage of a composition comprising a therapeutic vector having a Ztnfr12 nucleotide sequence, such as a recombinant virus, will vary depending upon such factors as the subject's age, weight, height, sex, general medical condition and previous medical history. Suitable routes of administration of therapeutic vectors include intravenous injection, intraarterial injection, intraperitoneal injection, intramuscular injection, intratumoral injection, and injection into a cavity that contains a tumor. As an illustration, Horton et al., Proc. Nat'l Acad. Sci. USA 96:1553 (1999), demonstrated that intramuscular injection of plasmid DNA encoding interferon-α produces potent antitumor effects on primary and metastatic tumors in a murine model.

A composition comprising viral vectors, non-viral vectors, or a combination of viral and non-viral vectors of the present invention can be formulated according to known methods to prepare pharmaceutically useful compositions, whereby vectors or viruses are combined in a mixture with a pharmaceutically acceptable carrier. As noted above, a composition, such as phosphate-buffered saline is said to be a "pharmaceutically acceptable carrier" if its administration can be tolerated by a recipient subject. Other suitable carriers are well-known to those in the art (see, for example, Remington's Pharmaceutical Sciences, 19th Ed. (Mack Publishing Co. 1995), and Gilman's the Pharmacological Basis of Therapeutics, 7th Ed. (MacMillan Publishing Co. 1985)).

For purposes of therapy, a therapeutic gene expression vector, or a recombinant virus comprising such a vector, and a pharmaceutically acceptable carrier are administered to a subject in a therapeutically effective amount. A combination of an expression vector (or virus) and a pharmaceutically acceptable carrier is said to be administered in a "therapeutically effective amount" if the amount administered is physiologically significant. An agent is physiologically significant if its presence results in a detectable change in the physiology of a recipient subject. For example, an agent used to treat inflammation is physiologically significant if its presence alleviates the inflammatory response. As another example, an agent used to inhibit the growth of tumor cells is physiologically significant if the administration of the agent results in a decrease in the number of tumor cells, decreased metastasis, a decrease in the size of a solid tumor, or increased necrosis of a tumor.

When the subject treated with a therapeutic gene expression vector or a recombinant virus is a human, then the therapy is preferably somatic cell gene therapy. That is, the preferred treatment of a human with a therapeutic gene expression vector or a recombinant virus does not entail introducing into cells a nucleic acid molecule that can form part of a human germ line and be passed onto successive generations (i.e., human germ line gene therapy).

14. Therapeutically Useful Immunoconjugates

The present invention contemplates the use of naked anti-Ztnfr12 antibodies (or naked antibody fragments thereof), as well as the use of immunoconjugates to effect treatment of various disorders, including B-cell malignancies, as discussed above. Immunoconjugates can be prepared using standard techniques. For example, immunoconjugates can be produced by indirectly conjugating a therapeutic agent to an antibody component (see, for example, Shih et al., Int. J. Cancer 41:832-839 (1988); Shih et al., Int. J. Cancer 46:1101-1106 (1990); and Shih et al., U.S. Pat. No. 5,057,313). Briefly, one standard approach involves reacting an antibody component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer can be an aminodextran or polypeptide of at least 50 amino acid residues, although other substantially equivalent polymer carriers can also be used. Preferably, the final immunoconjugate is soluble in an aqueous solution, such as mammalian serum, for ease of administration and effective targeting for use in therapy. Thus, solubilizing functions on the carrier polymer will enhance the serum solubility of the final immunoconjugate.

In an alternative approach for producing immunoconjugates comprising a polypeptide therapeutic agent, the therapeutic agent is coupled to aminodextran by glutaraldehyde condensation or by reaction of activated carboxyl groups on the polypeptide with amines on the aminodextran. Chelators can be attached to an antibody component to prepare immunoconjugates comprising radiometals or magnetic resonance enhancers. Illustrative chelators include derivatives of ethylenediaminetetraacetic acid and diethylenetriaminepentaacetic acid. Boron addends, such as carboranes, can be attached to antibody components by conventional methods.

Immunoconjugates can also be prepared by directly conjugating an antibody component with a therapeutic agent. The general procedure is analogous to the indirect method of conjugation except that a therapeutic agent is directly attached to an oxidized antibody component.

As a further illustration, a therapeutic agent can be attached at the hinge region of a reduced antibody component via disulfide bond formation. For example, the tetanus toxoid peptides can be constructed with a single cysteine residue that is used to attach the peptide to an antibody component. As an alternative, such peptides can be attached to the antibody component using a heterobifunctional cross-linker, such as N-succinyl 3-(2-pyridyldithio)proprionate. Yu et al., Int. J. Cancer 56:244 (1994). General techniques for such conjugation are well-known in the art. See, for example, Wong, Chemistry Of Protein Conjugation And Cross-Linking (CRC Press 1991); Upeslacis et al., "Modification of Antibodies by Chemical Methods," in Monoclonal Antibodies: Principles And Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering And Clinical Application, Riffer et al. (eds.), pages 60-84 (Cambridge University Press 1995).

As described above, carbohydrate moieties in the Fc region of an antibody can be used to conjugate a therapeutic agent. However, the Fc region is absent if an antibody fragment is used as the antibody component of the immunoconjugate. Nevertheless, it is possible to introduce a carbohydrate moiety into the light chain variable region of an antibody or antibody fragment. See, for example, Leung et al., J. Immunol. 154:5919 (1995); Hansen et al., U.S. Pat. No. 5,443,953 (1995). The engineered carbohydrate moiety is then used to attach a therapeutic agent.

In addition, those of skill in the art will recognize numerous possible variations of the conjugation methods. For example, the carbohydrate moiety can be used to attach polyethyleneglycol in order to extend the half-life of an intact antibody, or antigen-binding fragment thereof, in blood, lymph, or other extracellular fluids. Moreover, it is possible to construct a divalent immunoconjugate by attaching therapeutic agents to a carbohydrate moiety and to a free sulfhydryl group. Such a free sulfhydryl group may be located in the hinge region of the antibody component.

One type of immunoconjugate comprises an antibody component and a polypeptide cytotoxin. An example of a suitable polypeptide cytotoxin is a ribosome-inactivating protein. Type I ribosome-inactivating proteins are single-chain proteins, while type II ribosome-inactivating proteins consist of two nonidentical subunits (A and B chains) joined by a disulfide bond (for a review, see Soria et al., Targeted Diagn. Ther. 7:193 (1992)). Useful type I ribosome-inactivating proteins include polypeptides from Saponaria officinalis (e.g., saporin-1, saporin-2, saporin-3, saporin-6), *Momordica charantia* (e.g, momordin), *Byronia dioica* (e.g., bryodin, bryodin-2), *Trichosanthes kirilowii* (e.g., trichosanthin, trichokirin), *Gelonium multiflorum* (e.g., gelonin), *Phytolacca americana* (e.g., pokeweed antiviral protein, pokeweed antiviral protein-II, pokeweed antiviral protein-S), *Phytolacca dodecandra* (e.g., dodecandrin, Mirabilis antiviral protein), and the like. Ribosome-inactivating proteins are described, for example, by Walsh et al., U.S. Pat. No. 5,635,384.

Suitable type II ribosome-inactivating proteins include polypeptides from *Ricinus communis* (e.g., ricin), *Abrus precatorius* (e.g., abrin), *Adenia digitata* (e.g., modeccin), and the like. Since type II ribosome-inactiving proteins include a B chain that binds galactosides and a toxic A chain that depurinates adensoine, type II ribosome-inactivating protein conjugates should include the A chain. Additional useful ribosome-inactivating proteins include bouganin, clavin, maize ribosome-inactivating proteins, *Vaccaria pyramidata* ribosome-inactivating proteins, nigrine b, basic nigrine 1, ebuline, racemosine b, luffin-a, luffin-b, luffin-S, and other ribosome-inactivating proteins known to those of skill in the art. See, for example, Bolognesi and Stirpe, international publication No. WO98/55623, Colnaghi et al., international publication No. WO97/49726, Hey et al., U.S. Pat. No. 5,635, 384, Bolognesi and Stirpe, international publication No. WO95/07297, Arias et al., international publication No. WO94/20540, Watanabe et al., J. Biochem. 106:6977 (1989); Islam et al., Agric. Biol. Chem. 55:229 (1991), and Gao et al., FEBS Lett. 347:257 (1994).

Analogs and variants of naturally-occurring ribosome-inactivating proteins are also suitable for the targeting compositions described herein, and such proteins are known to those of skill in the art. Ribosome-inactivating proteins can be produced using publicly available amino acid and nucleotide sequences. As an illustration, a nucleotide sequence encoding saporin-6 is disclosed by Lorenzetti et al., U.S. Pat. No. 5,529,932, while Walsh et al., U.S. Pat. No. 5,635,384, describe maize and barley ribosome-inactivating protein nucleotide and amino acid sequences. Moreover, ribosome-inactivating proteins are also commercially available.

Additional polypeptide cytotoxins include ribonuclease, DNase I, Staphylococcal enterotoxin-A, diphtheria toxin, *Pseudomonas* exotoxin, and *Pseudomonas* endotoxin. See, for example, Pastan et al., Cell 47:641 (1986), and Goldenberg, Calif.—A Cancer Journal for Clinicians 44:43 (1994).

Another general type of useful cytotoxin is a tyrosine kinase inhibitor. Since the activation of proliferation by tyrosine kinases has been suggested to play a role in the development and progression of tumors, this activation can be inhibited by anti-Ztnfr12 antibody components that deliver tyrosine kinase inhibitors. Suitable tyrosine kinase inhibitors include isoflavones, such as genistein (5, 7, 4'-trihydroxyisoflavone), daidzein (7,4'-dihydroxyisoflavone), and biochanin A (4-methoxygenistein), and the like. Methods of conjugating tyrosine inhibitors to a growth factor are described, for example, by Uckun, U.S. Pat. No. 5,911,995.

Another group of useful polypeptide cytotoxins includes immunomodulators. As used herein, the term "immunomodulator" includes cytokines, stem cell growth factors, lymphotoxins, co-stimulatory molecules, hematopoietic factors, and the like, as well as synthetic analogs of these molecules. Examples of immunomodulators include tumor necrosis factor, interleukins (e.g., interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21), colony stimulating factors (e.g., granulocyte-colony stimulating factor and granulocyte macrophage-colony stimulating factor), interferons (e.g., interferons-$\alpha$, -$\beta$, -$\gamma$, -$\omega$, -$\epsilon$, and -$\tau$), the stem cell growth factor designated "S1 factor," erythropoietin, and thrombopoietin. Illustrative immunomodulator moieties include IL-2, IL-6, IL-10, interferon-□, TNF-□, and the like.

Immunoconjugates that include an immunomodulator provide a means to deliver an immunomodulator to a target cell, and are particularly useful against tumor cells. The cytotoxic effects of immunomodulators are well known to those of skill in the art. See, for example, Klegerman et al., "Lymphokines and Monokines," in Biotechnology And Pharmacy, Pessuto et al. (eds.), pages 53-70 (Chapman & Hall 1993). As an illustration, interferons can inhibit cell proliferation by inducing increased expression of class I histocompatibility antigens on the surface of various cells and thus, enhance the rate of destruction of cells by cytotoxic T lymphocytes. Furthermore, tumor necrosis factors, such as tumor necrosis factor-$\alpha$, are believed to produce cytotoxic effects by inducing DNA fragmentation.

The present invention also includes immunocongugates that comprise a nucleic acid molecule encoding a cytotoxin. As an example of this approach, Hoganson et al., Human Gene Ther. 9:2565 (1998), describe FGF-2 mediated delivery of a saporin gene by producing an FGF-2-polylysine conjugate which was condensed with an expression vector comprising a saporin gene.

Other suitable toxins are known to those of skill in the art.

Conjugates of cytotoxic polypeptides and antibody components can be prepared using standard techniques for conjugating polypeptides. For example, Lam and Kelleher, U.S. Pat. No. 5,055,291, describe the production of antibodies conjugated with either diphtheria toxin fragment A or ricin toxin. The general approach is also illustrated by methods of conjugating fibroblast growth factor with saporin, as described by Lappi et al., Biochem. Biophys. Res. Commun. 160:917 (1989), Soria et al., Targeted Diagn. Ther. 7:193 (1992), Buechler et al., Eur. J. Biochem. 234:706 (1995), Behar-Cohen et al., Invest. Ophthalmol. Vis. Sci. 36:2434 (1995), Lappi and Baird, U.S. Pat. No. 5,191,067, Calabresi et al., U.S. Pat. No. 5,478,804, and Lappi and Baird, U.S. Pat. No. 5,576,288. Also see, Ghetie and Vitteta, "Chemical Construction of Immunotoxins," in Drug Targeting: Strategies, Principles, and Applications, Francis and Delgado (Eds.), pages 1-26 (Humana Press, Inc. 2000), Hall (Ed.), Immunotoxin Methods and Protocols (Humana Press, Inc. 2000), and Newton and Rybak, "Construction of Ribonuclease-Antibody Conjugates for Selective Cytotoxicity," in Drug Targeting: Strategies, Principles, and Applications, Francis and Delgado (Eds.), pages 27-35 (Humana Press, Inc. 2000).

Alternatively, fusion proteins comprising an antibody component and a cytotoxic polypeptide can be produced using standard methods. Methods of preparing fusion proteins comprising a cytotoxic polypeptide moiety are well-known in the art of antibody-toxin fusion protein production. For example, antibody fusion proteins comprising an interleukin-2 moiety are described by Boleti et al., Ann. Oncol. 6:945 (1995), Nicolet et al., Cancer Gene Ther. 2:161 (1995), Becker et al., Proc. Nat'l Acad. Sci. USA 93:7826 (1996), Hank et al., Clin. Cancer Res. 2:1951 (1996), and Hu et al., Cancer Res. 56:4998 (1996). In addition, Yang et al., Hum. Antibodies Hybridomas 6:129 (1995), describe a fusion protein that includes an $F(ab')_2$ fragment and a tumor necrosis factor alpha moiety. Antibody-Pseudomonas exotoxin A fusion proteins have been described by Chaudhary et al., Nature 339:394 (1989), Brinkmann et al., Proc. Nat'l Acad. Sci. USA 88:8616 (1991), Batra et al., Proc. Nat'l Acad. Sci. USA 89:5867 (1992), Friedman et al., J. Immunol. 150:3054 (1993), Wels et al., Int. J. Can. 60:137 (1995), Fominaya et al., J. Biol. Chem. 271:10560 (1996), Kuan et al., Biochemistry 35:2872 (1996), and Schmidt et al., Int. J. Can. 65:538 (1996). Antibody-toxin fusion proteins containing a diphtheria toxin moiety have been described by Kreitman et al., Leukemia 7:553 (1993), Nicholls et al., J. Biol. Chem. 268:5302 (1993), Thompson et al., J. Biol. Chem. 270:28037 (1995), and Vallera et al., Blood 88:2342 (1996). Deonarain et al., Tumor Targeting 1:177 (1995), have described an antibody-toxin fusion protein having an RNase moiety, while Linardou et al., Cell Biophys. 24-25:243 (1994), produced an antibody-toxin fusion protein comprising a DNase I component. Gelonin was used as the toxin moiety in the antibody-toxin fusion protein of Better et al., J. Biol. Chem. 270:14951 (1995). As a further example, Dohlsten et al., Proc. Nat'l Acad. Sci. USA 91:8945 (1994), reported an antibody-toxin fusion protein comprising Staphylococcal enterotoxin-A. Also see, Newton and Rybak, "Preparation of Recombinant RNase Single-Chain Antibody Fusion Proteins," in Drug Targeting: Strategies, Principles, and Applications, Francis and Delgado (Eds.), pages 77-95 (Humana Press, Inc. 2000).

As an alternative to a polypeptide cytotoxin, immunoconjugates can comprise a radioisotope as the cytotoxic moiety. For example, an immunoconjugate can comprise an anti-Ztnfr12 antibody component and an α-emitting radioisotope, a β-emitting radioisotope, a γ-emitting radioisotope, an Auger electron emitter, a neutron capturing agent that emits α-particles or a radioisotope that decays by electron capture. Suitable radioisotopes include $^{198}Au$, $^{199}Au$, $^{32}P$, $^{33}P$, $^{125}I$, $^{131}I$, $^{123}I$, $^{90}Y$, $^{186}Re$, $^{188}Re$, $^{67}Cu$, $^{211}At$, $^{47}Sc$, $^{103}Pb$, $^{109}Pd$, $^{212}Pb$, $^{71}Ge$, $^{77}As$, $^{105}Rh$, $^{113}Ag$, $^{119}Sb$, $^{121}Sn$, $^{131}Cs$, $^{143}Pr$, $^{161}Tb$, $^{177}Lu$, $^{191}Os$, $^{193M}Pt$, $^{197}Hg$, and the like.

A radioisotope can be attached to an antibody component directly or indirectly, via a chelating agent. For example, $^{67}Cu$, which provides β-particles and γ-rays, can be conjugated to an antibody component using the chelating agent, p-bromoacetamido-benzyl-tetraethylaminetetraacetic acid. Chase and Shapiro, "Medical Applications of Radioisotopes," in Gennaro (Ed.), Remington: The Science and Practice of Pharmacy, 19th Edition, pages 843-865 (Mack Publishing Company 1995). As an alternative, $^{90}Y$, which emits an energetic β-particle, can be coupled to an antibody component using diethylenetriaminepentaacetic acid. Moreover, an exemplary suitable method for the direct radiolabeling of an antibody component with $^{131}I$ is described by Stein et al., Antibody Immunoconj. Radiopharm. 4:703 (1991). Alternatively, boron addends such as carboranes can be attached to antibody components, using standard techniques.

Another type of suitable cytotoxin for the preparation of immunoconjugates is a chemotherapeutic drug. Illustrative chemotherapeutic drugs include nitrogen mustards, alkyl sulfonates, nitrosoureas, triazenes, folic acid analogs, pyrimidine analogs, purine analogs, antibiotics, epipodophyllotoxins, platinum coordination complexes, and the like. Specific examples of chemotherapeutic drugs include methotrexate, doxorubicin, daunorubicin, cytosinarabinoside, cis-platin, vindesine, mitomycin, bleomycin, melphalan, chlorambucil, maytansinoids, calicheamicin, taxol, and the like. Suitable chemotherapeutic agents are described in Remington: The Science and Practice of Pharmacy, 19th Edition (Mack Publishing Co. 1995), and in Goodman And Gilman's The Pharmacological Basis Of Therapeutics, 9th Ed. (MacMillan Publishing Co. 1995). Other suitable chemotherapeutic agents are known to those of skill in the art.

In another approach, immunoconjugates are prepared by conjugating photoactive agents or dyes to an antibody component. Fluorescent and other chromogens, or dyes, such as porphyrins sensitive to visible light, have been used to detect and to treat lesions by directing the suitable light to the lesion. This type of "photoradiation," "phototherapy," or "photodynamic" therapy is described, for example, by Mew et al., J. Immunol. 130:1473 (1983), Jori et al. (eds.), Photodynamic Therapy Of Tumors And Other Diseases (Libreria Progetto 1985), Oseroff et al., Proc. Natl. Acad. Sci. USA 83:8744 (1986), van den Bergh, Chem. Britain 22:430 (1986), Hasan et al., Prog. Clin. Biol. Res. 288:471 (1989), Tatsuta et al., Lasers Surg. Med. 9:422 (1989), and Pelegrin et al., Cancer 67:2529 (1991).

Immunoconjugates used for therapy can comprise pharmaceutically acceptable water-soluble polymer moieties. Methods for attaching such polymers are known to those of skill in the art, and have been described previously.

The approaches described above can also be used to prepare multispecific antibody compositions that comprise an immunoconjugate. Polypeptide cytotoxins can also be conjugated with a soluble polymer using the above methods either before or after conjugation to an antibody component. Soluble polymers can also be conjugated with antibody fusion proteins.

In general, anti-Ztnfr12 immunoconjugates can be administered as discussed previously with regard to the therapeutic uses of Ztnfr12 polypeptides. Naked anti-Ztnfr12 antibodies, or antibody fragments, can be supplemented with immunoconjugate or antibody fusion protein administration. In one variation, naked anti-Ztnfr12 antibodies (or naked antibody fragments) are administered with low-dose radiolabeled anti-Ztnfr12 antibodies or antibody fragments. As a second alternative, naked anti-Ztnfr12 antibodies (or antibody fragments) are administered with low-dose radiolabeled anti-Ztnfr12 antibody-cytokine immunoconjugates. As a third alternative, naked anti-Ztnfr12 antibodies (or antibody fragments) are administered with anti-Ztnfr12-cytokine immunoconjugates that are not radiolabeled. With regard to "low doses" of $^{131}$I-labeled immunoconjugates, a preferable dosage is in the range of 15 to 40 mCi, while the most preferable range is 20 to 30 mCi. In contrast, a preferred dosage of $^{90}$Y-labeled immunoconjugates is in the range from 10 to 30 mCi, while the most preferable range is 10 to 20 mCi. Similarly, bispecific antibody components can be supplemented with immunoconjugate or antibody fusion protein administration.

Immunoconjugates having a boron addend-loaded carrier for thermal neutron activation therapy will normally be effected in similar ways. However, it will be advantageous to wait until non-targeted immunoconjugate clears before neutron irradiation is performed. Clearance can be accelerated using an antibody that binds to the immunoconjugate. See U.S. Pat. No. 4,624,846 for a description of this general principle.

The present invention also contemplates a method of treatment in which immunomodulators are administered to prevent, mitigate or reverse radiation-induced or drug-induced toxicity of normal cells, and especially hematopoietic cells. Adjunct immunomodulator therapy allows the administration of higher doses of cytotoxic agents due to increased tolerance of the recipient mammal. Moreover, adjunct immunomodulator therapy can prevent, palliate, or reverse dose-limiting marrow toxicity. Examples of suitable immunomodulators for adjunct therapy include granulocyte-colony stimulating factor, granulocyte macrophage-colony stimulating factor, thrombopoietin, IL-1, IL-3, IL-12, and the like. The method of adjunct immunomodulator therapy is disclosed by Goldenberg, U.S. Pat. No. 5,120,525.

Anti-Ztnfr12 antibodies and immunoconjugates can be tested using the in vitro approaches and animal models described above for the evaluation of Ztnfr12 polypeptides and Ztnfr12 fusion proteins.

The efficacy of anti-Ztnfr12 antibody therapy can be enhanced by supplementing naked antibody components with immunoconjugates and other forms of supplemental therapy described herein. In such multimodal regimens, the supplemental therapeutic compositions can be administered before, concurrently or after administration of naked anti-Ztnfr12 antibodies. Multimodal therapies of the present invention further include immunotherapy with naked anti-Ztnfr12 antibody components supplemented with administration of anti-Ztnfr12 immunoconjugates. In another form of multimodal therapy, subjects receive naked anti-Ztnfr12 antibodies and standard cancer chemotherapy.

Pharmaceutical compositions may be supplied as a kit comprising a container that comprises anti-Ztnfr12 antibody components, or bispecific antibody components. Therapeutic molecules can be provided in the form of an injectable solution for single or multiple doses, or as a sterile powder that will be reconstituted before injection. Alternatively, such a kit can include a dry-powder disperser, liquid aerosol generator, or nebulizer for administration of an anti-Ztnfr12 antibody component. Such a kit may further comprise written information on indications and usage of the pharmaceutical composition. Moreover, such information may include a statement that the composition is contraindicated in patients with known hypersensitivity to exogenous antibodies.

15. Production of Transgenic Mice

Transgenic mice can be engineered to over-express the Ztnfr12 gene in all tissues or under the control of a tissue-specific or tissue-preferred regulatory element. These overproducers of Ztnfr12 can be used to characterize the phenotype that results from over-expression, and the transgenic animals can serve as models for human disease caused by excess Ztnfr12. Transgenic mice that over-express Ztnfr12 also provide model bioreactors for production of Ztnfr12, such as soluble Ztnfr12, in the milk or blood of larger animals. Methods for producing transgenic mice are well-known to those of skill in the art (see, for example, Jacob, "Expression and Knockout of Interferons in Transgenic Mice," in Overexpression and Knockout of Cytokines in Transgenic Mice, Jacob (ed.), pages 111-124 (Academic Press, Ltd. 1994), Monastersky and Robl (eds.), Strategies in Transgenic Animal Science (ASM Press 1995), and Abbud and Nilson, "Recombinant Protein Expression in Transgenic Mice," in Gene Expression Systems: Using Nature for the Art of Expression, Fernandez and Hoeffler (eds.), pages 367-397 (Academic Press, Inc. 1999)).

For example, a method for producing a transgenic mouse that expresses a Ztnfr12 gene can begin with adult, fertile males (studs) (B6C3f1, 2-8 months of age (Taconic Farms, Germantown, N.Y.)), vasectomized males (duds) (B6D2f1, 2-8 months, (Taconic Farms)), prepubescent fertile females (donors) (B6C3f1, 4-5 weeks, (Taconic Farms)) and adult fertile females (recipients) (B6D2f1, 2-4 months, (Taconic Farms)). The donors are acclimated for one week and then injected with approximately 8 IU/mouse of Pregnant Mare's Serum gonadotrophin (Sigma Chemical Company; St. Louis, Mo.) I.P., and 46-47 hours later, 8 IU/mouse of human Chorionic Gonadotropin (hCG (Sigma)) I.P. to induce superovulation. Donors are mated with studs subsequent to hormone injections. Ovulation generally occurs within 13 hours of hCG injection. Copulation is confirmed by the presence of a vaginal plug the morning following mating.

Fertilized eggs are collected under a surgical scope. The oviducts are collected and eggs are released into urinanalysis slides containing hyaluronidase (Sigma). Eggs are washed once in hyaluronidase, and twice in Whitten's W640 medium (described, for example, by Menino and O'Claray, Biol. Reprod. 77:159 (1986), and Dienhart and Downs, Zygote 4:129 (1996)) that has been incubated with 5% $CO_2$, 5% $O_2$, and 90% $N_2$ at 37° C. The eggs are then stored in a 37° C./5% $CO_2$ incubator until microinjection.

Ten to twenty micrograms of plasmid DNA containing a Ztnfr12 encoding sequence is linearized, gel-purified, and resuspended in 10 mM Tris-HCl (pH 7.4), 0.25 mM EDTA (pH 8.0), at a final concentration of 5-10 nanograms per microliter for microinjection. For example, the Ztnfr12 encoding sequences can encode a polypeptide comprising amino acid residues 1 to 69 of SEQ ID NO:2, comprising amino acid residues 1 to 79 of SEQ ID NO:2, or comprising amino acid residues 1 to 69 of SEQ ID NO:13.

Plasmid DNA is microinjected into harvested eggs contained in a drop of W640 medium overlaid by warm, $CO_2$-equilibrated mineral oil. The DNA is drawn into an injection needle (pulled from a 0.75 mm ID, 1 mm OD borosilicate glass capillary), and injected into individual eggs. Each egg is penetrated with the injection needle, into one or both of the haploid pronuclei.

Picoliters of DNA are injected into the pronuclei, and the injection needle withdrawn without coming into contact with the nucleoli. The procedure is repeated until all the eggs are injected. Successfully microinjected eggs are transferred into an organ tissue-culture dish with pre-gassed W640 medium for storage overnight in a 37° C./5% $CO_2$ incubator.

The following day, two-cell embryos are transferred into pseudopregnant recipients. The recipients are identified by the presence of copulation plugs, after copulating with vasectomized duds. Recipients are anesthetized and shaved on the dorsal left side and transferred to a surgical microscope. A small incision is made in the skin and through the muscle wall in the middle of the abdominal area outlined by the ribcage, the saddle, and the hind leg, midway between knee and spleen. The reproductive organs are exteriorized onto a small surgical drape. The fat pad is stretched out over the surgical drape, and a baby serrefine (Roboz, Rockville, Md.) is attached to the fat pad and left hanging over the back of the mouse, preventing the organs from sliding back in.

With a fine transfer pipette containing mineral oil followed by alternating W640 and air bubbles, 12-17 healthy two-cell embryos from the previous day's injection are transferred into the recipient. The swollen ampulla is located and holding the oviduct between the ampulla and the bursa, a nick in the oviduct is made with a 28 g needle close to the bursa, making sure not to tear the ampulla or the bursa.

The pipette is transferred into the nick in the oviduct, and the embryos are blown in, allowing the first air bubble to escape the pipette. The fat pad is gently pushed into the peritoneum, and the reproductive organs allowed to slide in. The peritoneal wall is closed with one suture and the skin closed with a wound clip. The mice recuperate on a 37° C. slide warmer for a minimum of four hours.

The recipients are returned to cages in pairs, and allowed 19-21 days gestation. After birth, 19-21 days postpartum is allowed before weaning. The weanlings are sexed and placed into separate sex cages, and a 0.5 cm biopsy (used for genotyping) is snipped off the tail with clean scissors.

Genomic DNA is prepared from the tail snips using, for example, a QIAGEN DNEASY kit following the manufacturer's instructions. Genomic DNA is analyzed by PCR using primers designed to amplify a Ztnfr12 gene or a selectable marker gene that was introduced in the same plasmid. After animals are confirmed to be transgenic, they are back-crossed into an inbred strain by placing a transgenic female with a wild-type male, or a transgenic male with one or two wild-type female(s). As pups are born and weaned, the sexes are separated, and their tails snipped for genotyping.

To check for expression of a transgene in a live animal, a partial hepatectomy is performed. A surgical prep is made of the upper abdomen directly below the zyphoid process. Using sterile technique, a small 1.5-2 cm incision is made below the sternum and the left lateral lobe of the liver exteriorized. Using 4-0 silk, a tie is made around the lower lobe securing it outside the body cavity. An atraumatic clamp is used to hold the tie while a second loop of absorbable Dexon (American Cyanamid; Wayne, N.J.) is placed proximal to the first tie. A distal cut is made from the Dexon tie and approximately 100 mg of the excised liver tissue is placed in a sterile petri dish. The excised liver section is transferred to a 14 ml polypropylene round bottom tube and snap frozen in liquid nitrogen and then stored on dry ice. The surgical site is closed with suture and wound clips, and the animal's cage placed on a 37° C. heating pad for 24 hours post operatively. The animal is checked daily post operatively and the wound clips removed 7-10 days after surgery. The expression level of Ztnfr12 mRNA is examined for each transgenic mouse using an RNA solution hybridization assay or polymerase chain reaction.

In addition to producing transgenic mice that over-express Ztnfr12, it is useful to engineer transgenic mice with either abnormally low or no expression of the gene. Such transgenic mice provide useful models for diseases associated with a lack of Ztnfr12. As discussed above, Ztnfr12 gene expression can be inhibited using anti-sense genes, ribozyme genes, or external guide sequence genes. To produce transgenic mice that under-express the Ztnfr12 gene, such inhibitory sequences are targeted to Ztnfr12 mRNA. Methods for producing transgenic mice that have abnormally low expression of a particular gene are known to those in the art (see, for example, Wu et al., "Gene Underexpression in Cultured Cells and Animals by Antisense DNA and RNA Strategies," in Methods in Gene Biotechnology, pages 205-224 (CRC Press 1997)).

An alternative approach to producing transgenic mice that have little or no Ztnfr12 gene expression is to generate mice having at least one normal Ztnfr12 allele replaced by a nonfunctional Ztnfr12 gene. One method of designing a nonfunctional Ztnfr12 gene is to insert another gene, such as a selectable marker gene, within a nucleic acid molecule that encodes Ztnfr12. Standard methods for producing these so-called "knockout mice" are known to those skilled in the art (see, for example, Jacob, "Expression and Knockout of Interferons in Transgenic Mice," in Overexpression and Knockout of Cytokines in Transgenic Mice, Jacob (ed.), pages 111-124 (Academic Press, Ltd. 1994), and Wu et al., "New Strategies for Gene Knockout," in Methods in Gene Biotechnology, pages 339-365 (CRC Press 1997)).

The present invention, thus generally described, will be understood more readily by reference to the following examples, which are provided by way of illustration and is not intended to be limiting of the present invention.

Example 1

Isolation of a Nucleic Acid Molecule Encoding Ztnfr12

This study used a human B-lymphoid precursor cell line, designated as "Reh" (ATCC No. CRL-8286). A cDNA library was prepared from Reh cells, and arrayed using sixteen 96-well plates. Each well contained about 250 *E. coli* colonies with each colony containing one cDNA clone. DNA minipreps were prepared in 96-well format using the Qiaprep96 Turbo kit (Qiagen, Inc.; Valencia, Calif.). The DNA was then divided into 128 pools that represented 3000 clones each. These pools were transfected into COS-7 cells in 12-well plates, and the positive pools were determined by cell-surface ZTNF4 binding.

The COS cell transfection was performed as follows. Five microliters of pooled DNA (about 0.5-1.0 □g) and 5 □l of lipofectamine were mixed in 92 □l of serum free DMEM medium (55 mg sodium pyruvate, 146 mg L-glutamine, 5 mg transferrin, 2.5 mg insulin, 1 □g selenium, and 5 mg fetuin in 500 ml DMEM), incubated at room temperature for 30 minutes, and then 400 □l of serum free DMEM medium were added. Five hundred microliters of this mixture were added to $1.5 \times 10^5$ COS cells/well plated on 12-well fibrinectin-pretreated tissue culture plates, and the cells were incubated for 5 hours at 37° C. Then, 500 □l of 20% FBS DMEM medium (100 ml FBS, 55 mg sodium pyruvate, and 146 mg L-glutamine in 500 ml DMEM) were added per well, and the cells were incubated overnight.

The cell-surface binding assay was performed using biotinylated FLAG-tagged ZTNF4 as follows. Media were rinsed from the cells with 1% BSA/PBS and the cells were blocked for 1 hour with TNB (0.1 M Tris-HCL, 0.15 M NaCl, and 0.5% Blocking Reagent—NEN Renaissance TSA-Direct Kit Cat# NEL701—in $H_2O$). Then, the cells were incubated for 1 hour with 3 □g/ml biotinylated FLAG-tagged ZTNF4 in TNB. Cells were washed with 1% BSA/PBS, and then incubated for another hour with 1:300 diluted streptavidin-HRP (NEN kit) in TNB. Cells were washed with 1% BSA/PBS and then fixed for 15 minutes with 1.8% formaldehyde in PBS. Next, the cells were washed with TNT (0.1 M Tris-HCL, 0.15 M NaCl, and 0.05% Tween-20 in water). Binding was detected by incubating cells for four to five minutes with fluorescein tyramide reagent diluted 1:50 in dilution buffer (NEN kit). Cells were washed with TNT, and were preserved with VECTASHIELD Mounting Media (Vector Labs; Burlingame, Calif.) diluted 1:5 in TNT. The cells were visualized using an FITC filter on a fluorescent microscope.

One of the positive DNA pools, "10A11," was identified using the method described above. The DNA of pool 10A11 was electroporated into E. coli DH10B, and the colonies were filter-lifted and washed. DNA isolated from E. coli was then transfected into COS cells, and the positive pool DNA "4D" was identified using the ZTNF4 binding assay. The colonies of pool 4D were transferred into a 96-well, and the DNA was isolated using the Qiaprep96 Turbo kit. The positive clone 4D2H-6 was identified using the method mentioned above. To test the specificity of ZTNF4 binding, the 4D2H-6 clone DNA was transfected into COS cells, and the binding of ZTNF4 and ZTNF2 was tested. Although ZTNF4 binds to COS cells transfected with 4D2H-6 DNA, ZTNF2 did not bind with the cells. In contrast, both ZTNF4 and ZTNF2 bound to COS cells transfected with TACI DNA.

Example 2

Ztnfr 12 Gene Expression in Human and Murine Tissues

Northern blot analysis was performed using Human Multiple Tissue Blots (MTN I, MTN II, and MTN III) (CLONTECH Laboratories, Inc.; Palo Alto, Calif.), Human Immune System blot (CLONTECH), Human normal mRNA blot (Invitrogen, San Diego, Calif.) and Human Fetal Multiple Tissue Blots (CLONTECH). A 570 base pair human probe was generated by PCR with oligonucleotides 37550 (5' GCGAAT-TCGTCGGCACCATGAGGCGAGGG 3'; SEQ ID NO:10) and 37549 (5' CGCTCGAGCTGCCGGCTCCCTGCTAT-TGTTG 3'; SEQ ID NO:11), under the following reaction conditions: 94° C. for 2 minutes; 35 cycles of 94° C. for 30 seconds, 60° C. for 30 seconds, 72° C. for 30 seconds; followed by 72° C. for 5 minutes. The PCR fragment was gel-purified using QIAQUICK gel extraction kit (QIAGEN, Inc.; Santa Clarita, Calif.). The probe was radioactively labeled with $^{32}$P using the REDIPRIME II DNA Labeling system (AMERSHAM, Inc.; UK) according to the manufacturer's specifications. The probe was purified using a NUCTRAP push column (Stratagene; La Jolla, Calif.). EXPRESSHYB (CLONTECH) solution was used for the hybridizing solution for the blots. Hybridization took place overnight at 65° C.

The blots were then washed four times with 2×SCC and 0.05% SDS at room temperature, followed by two washes in 0.1×SSC and 0.1% SDS at 50° C. One transcript size was detected at approximately 4.4 kilobases.

Tumor Blots were also examined with human uterus tumor blot (Invitrogen, San Diego, Calif.), human tumor panel blot 4 and 5 (Invitrogen Corporation; San Diego, Calif.), human lymphoma blot (Invitrogen), human cancer cell line blot (CLONTECH) and a human leukemia blot. Dot blots were also analyzed using a Human Multiple Tissue Expression Blot (CLONTECH) and a Human Cancer Gene Screening Blot (Biochain Institute, Inc.; Hayward, Calif.). The methods and conditions for the dot blot analyses were the same as for the multiple tissue blots disclosed above.

Ztnfr12 gene expression was observed in spleen, lymph node, peripheral blood lymphocytes, kidney, heart, liver, skeletal muscle, pancreas, adrenal gland, testis, brain, uterus, stomach, bone marrow, trachea thymus, placenta, fetal liver and Raji cells. The strongest signals were associated with spleen tissue, lymph node tissue, and in peripheral blood.

Example 3

Ztnfr12 Gene Expression in Cell Lines

TAQMAN RT-PCR (Applied Biosystems; Foster City, Calif.) was used to further examine expression of the Ztnfr12 gene, as well as TACI and BCMA genes. In these studies, the expression of endogenous human □-glucuronidase or glyceraldehyde-3-phosphate dehydrogenase were used as controls. Ztnfr12, TACI, and BCMA RNA levels were compared against the RNA levels of these control genes.

As shown in Table 6, the results indicated that Ztnfr12 is primarily exclusively expressed on B lineage cells. In particular, Ztnfr12 gene expression was observed in transformed B lymphoma cell lines, such as cells derived from Burkitt's lymphoma (e.g., RAMOS cells, DAUDI cells, RAJI cells, BJAB cells, and HS Sultan cells), cells derived from Non-Hodgkin's lymphoma (RL cells), B-cell lymphoblastic leukemia cells (IM9, SUP-B15, and REH cells), and the B-cell lymphoma cell lines, DOHH-2, and WSU-NHL. In contrast, Ztnfr12 gene expression was not detectable in acute T-cell lymphoma cells (Jurkat), monocytic leukemia cells (THP-1 and U937), promyelocytic leukemia cells (HL-60), and chronic myelogenous leukemia cells (K562).

These results indicate that the Ztnfr12 protein could provide a useful target in monoclonal antibody therapy against Burkitt's lymphoma, Non-Hodgkin's lymphoma, acute lymphoblastic leukemia, and a variety of other B-cell lymphomas. Ztnfr12 expression is also quite high in many of these cells lines compared with the expression levels of similar receptors. For example, BCMA seems to be primarily expressed on plasma cells.

TABLE 6

Ztnfr12, TACI, and BCMA Gene Expression

| | Level of Receptor Gene Expression | | |
|---|---|---|---|
| Cell Line | Ztnfr12 | TACI | BCMA |
| IM9 | +++ | ++ | + |
| RAMOS | +++ | + | − |
| DAUDI | +++ | + | − |
| RAJI | +++ | + | − |
| HS Sultan | ++ | − | ++ |
| MC-116 | − | − | + |
| BJAB | +++ | − | +/− |
| RL | +++ | − | + |
| SUP-B15 | ++ | + | + |
| DOHH-2 | ++ | − | + |
| WSU-NHL | + | + | − |
| REH | + | − | − |
| K562 | − | − | − |
| HL-60 | − | −/+ | − |
| THP-1 | − | − | − |
| U937 | − | − | − |

Example 4

Construction and Expression of Ztnfr12-Fc Fusion Protein

A. Ig □1 Fragment Construction

To prepare the Ztnfr12-Fc4 fusion protein, the Fc region of human IgG1 (the hinge region and the $CH_2$ and $CH_3$ domains) was modified to remove Fc□1 receptor (Fc□RI) and complement (C1q) binding functions. This modified version of human IgG1 Fc was designated "Fc4."

The Fc region was isolated from a human fetal liver library (Clontech) PCR using oligo primers 5' ATCAGCGGAA TTCAGATCTT CAGACAAAAC TCACACATGC CCAC 3' (SEQ ID NO:15) and 5' GGCAGTCTCT AGATCATTTA CCCGGAGACA GGGAG 3' (SEQ ID 15 NO:16). The nucleotide and amino acid sequences of a wild-type human □1 constant region are presented in SEQ ID Nos: 17 and 18, respectively. Mutations within the Fc region were introduced by PCR to reduce Fc□RI binding. The Fc□RI binding site (Leu-Leu-Gly-Gly; amino acid residues 38 to 41 of SEQ ID NO:18, which correspond to EU index positions 234 to 237) was mutated to Ala-Glu-Gly-Ala to reduce Fc□R1 binding (see, for example, Duncan et al., Nature 332:563 (1988); Baum et al., EMBO J. 13:3992 (1994)). Oligonucleotide primers 5' CCGTGCCCAG CACCTGAAGC CGAGGGGGCA CCGTCAGTCT TCCTCTTCCC C 3' (SEQ ID NO:19) and 5' GGATTCTAGA TTATTTACCC GGAGACAGGG A 3' (SEQ ID NO:20) were used to introduce the mutation. To a 50 □l final volume was added 570 ng of IgFc template, 5 □l of 10× Pfu reaction Buffer (Stratagene), 8 □l of 1.25 mM dNTPs, 31 □l of distilled water, 2 □l of 205 mM oligonucleotide primers. A volume of mineral oil was added and the reaction was heated to 94° C. for one minute. Pfu polymerase (2.5 units, Stratagene) was added followed by 25 cycles at 94° C. for 30 seconds, 55° C. for 30 seconds, 72° C. for one minute followed by a seven minute extension at 72° C. The reaction products were fractioned by electrophoresis, and the band corresponding to the predicted size of about 676 base pairs was detected. This band was excised from the gel and recovered using a QIAGEN QIAQUICK Gel Extraction Kit (Qiagen) according to the manufacturer's instructions. This fragment was designated as the Fc□RI binding site mutated IgFc sequence.

PCR was also used to introduce a mutation of Ala to Ser (amino acid residue 134 of SEQ ID NO:18, which corresponds to EU index position 330) and Pro to Ser (amino acid residue 135 of SEQ ID NO:18, which corresponds to EU index position 331) to reduce complement C1q binding or complement fixation (Duncan and Winter, Nature 332:788 (1988)). Two first round reactions were performed using the FcγRI binding side-mutated IgFc sequence as a template. To a 50 □l final volume was added 1 □l of FcγRI binding site mutated IgFc template, 5 □l of 10× Pfu Reaction Buffer (Stratagene), 8 □l of 1.25 mM dNTPs, 31 of □l distilled water, 2 □l of 20 mM 5' GGTGGCGGCT CCCAGATGGG TCCTGTCCGA GCCCAGATCT TCAGACAAAA CTCAC 3' (SEQ ID NO:21), a 5' primer beginning at nucleotide 36 of SEQ ID NO:17, and 2 □l of 20 mM 5' TGGGAGGGCT TTGTTGGA 3' (SEQ ID NO:22), a 3' primer beginning at the complement of nucleotide 405 of SEQ ID NO:17. The second reaction contained 2 □l each of 20 mM stocks of oligonucleotide primers 5' TCCAACAAAG CCCTCCCATC CTCCATCGAG AAAACCATCT CC 3' (SEQ ID NO:23), a 5' primer beginning at nucleotide 388 of SEQ ID NO:17 and 5' GGATGGATCC ATGAAGCACC TGTGGTTCTT CCTCCTGCTG GTGGCGGCTC CCAGATG 3' (SEQ ID NO:24), a 3' primer, to introduce the Ala to Ser mutation, XbaI restriction site and stop codon. An equal volume of mineral oil was added and the reactions were heated to 94° C. for one minute. Pfu polymerase (2.5 units, Stratagene) was added followed by 25 cycles at 94° C. for 30 seconds, 55° C. for 30 seconds, 72° C. for 2 minutes followed by a seven minute extension at 72° C. The reaction products were fractionated by electrophoresis, and bands corresponding to the predicted sizes, about 370 and about 395 base pairs respectively, were detected. The bands were excised from the gel and extracted using a QIAGEN QIAQUICK Gel Extraction Kit (Qiagen) according to the manufacturer's instructions.

A second round reaction was performed to join the above fragments and add the 5' BamHI restriction site and a signal sequence from the human immunoglobulin JBL 2'C$_L$ heavy chain variable region (Cogne et al., Eur. J. Immunol. 18:1485 (1988)). To a 50 □l final volume was added 30 □l of distilled water, 8 □l of 1.25 mM dNTPs, 5 □l of 10× Pfu polymerase reaction buffer (Stratagene) and 1 □l each of the two first two PCR products. An equal volume of mineral oil was added and the reaction was heated to 94° C. for one minute. Pfu polymerase (2.5 units, Stratagene) was added followed by five cycles at 94° C. for 30 seconds, 55° C. for 30 seconds, and 72° C. for 2 minutes. The temperature was again brought to 94° C. and 2 □l each of 20 mM stocks of 5' GGATGGATCC ATGAAGCACC TGTGGTTCTT CCTCCTGCTG GTGGCGGCTC CCAGATG 3' (SEQ ID NO:25), a 5' primer beginning at nucleotide 1 of SEQ ID NO:17 that introduces a BamHI restriction site, and 5' GGATTCTAGA TTATTTACCC GGAGACAGGG A 3' (SEQ ID NO:26) were added followed by 25 cycles at 94° C. for 30 seconds, 55° C. for 30 seconds and 72° C. for two minutes, and a final seven minute extension at 72° C. A portion of the reaction was visualized using gel electrophoresis. A 789 base pair band corresponding the predicted size was detected. The remainder of the mutated Fc PCR fragment was digested with the restriction enzymes BamHI and XbaI. The digested fragment was cloned and verified by sequence analysis. The mutated Fc was designated as "Fc4." The nucleotide and amino acid sequences of Fc4 are provided as SEQ ID NOs:27 and 28, respectively.

The Ig fusion segment designated as "Fc5" was generated by using PCR to amplify the Fc4 Ig fusion segment with oligonucleotide primers 5' GAGCCCAAAT CTTCAGACAA AACTCACACA TGCCCA 3' (SEQ ID NO:29) and 5' TAATTGGCGC GCCTCTAGAT TATTTACCCG GAGACA 3' (SEQ ID NO:30). The conditions of the PCR amplification were as follows. To a 50 □L final volume was added 236 ng Fc4 template, 5 □L 10× Pfu reaction buffer, 4 □L of 2.5 mM dNTPs, 1 □L 20 □M each of the primers and 1 □L Pfu polymerase (2.5 units, Stratagene). The amplification thermal profile consisted of 94° C. for 2 minutes, 5 cycles at 94° C. for 15 seconds, 42° C. for 20 seconds, 72° C. for 45 seconds, 20 cycles at 94° C. for 1 minute 20 seconds, followed by a seven minute extension at 72° C. The reaction product was electrophoresed on a preparative agarose gel and the band corresponding to the predicted size of 718 bp was detected. The band was excised from the gel and recovered using a QIAGEN QIAQUICK Gel Extraction Kit (Qiagen) according to the manufacturer's instructions. The mutated Fc fragment was cloned and verified by sequence analysis. The nucleotide and amino acid sequences of Fc5 are provided as SEQ ID NOs:31 and 32, respectively.

B. Ztnfr12-Fc5 Expression Vector Construction

A protein encoding expression cassette for Ztnfr12-tcs-Fc5 was generated by overlap PCR (Horton et al., Gene 77:61 (1989)) using a mouse immunoglobulin heavy chain variable region (Ig VH) signal sequence cDNA, a Ztnfr12 cDNA, and an Fc5 DNA fragment as PCR templates. The term "tcs" indicates the presence of a thrombin cleavage site between the Ztnfr12 segment and the Fc5 segment.

The first round PCR amplifications consisted of four separate reactions that generated the four PCR products (designated as First Round PCR Products 1, 2, 3, and 4) to be used in the second round, overlap PCR.

First Round PCR Products 1, 2, 3, and 4 were separately generated using different oligonucleotide primers and DNA templates. To a 25 μl final volume each was added approximately 2 ng template DNA, 2.5 μl 10× Pfu Polymerase Reaction Buffer (Stratagene), 2 μl of 2.5 mM dNTPs, 2.5 μl Rediload (ReGen; Huntsville, Ala.), 20 pmole each 5' oligonucleotide and 3' oligonucleotide primers (see below), and 0.5 μl Pfu polymerase (2.5 units, Stratagene). The reaction to generate First Round PCR Product 4 also included the addition of 2.5 μl GC-Melt Reagent (Clontech). Information on the templates and primers used in the PCR amplifications is provided in Tables 7 and 8.

TABLE 7

Templates and Primers Used in the First Round of PCR Amplification

| PCR Product Number | Template | 5' Primer | 3' Primer |
|---|---|---|---|
| 1 | Murine Ig VH 26-10 signal sequence cDNA | ZC38,989 | ZC38,987 |
| 2 | Ztnfr12 cDNA | ZC38,986 | ZC38,990 |
| 3 | Ztnfr12 cDNA | ZC39,428 | ZC39,425 |
| 4 | Fc5 DNA fragment | ZC39,027 | ZC38,874 |

TABLE 8

Oligonucleotide Sequences

| Primer | Nucleotide Sequence | SEQ ID NO. |
|---|---|---|
| ZC38,989 | 5' GGCCGGCCACCATGGGAT 3' | 33 |
| ZC38,987 | 5' TCGCCTCATAGAGAGGACACCTGCAGT 3' | 34 |
| ZC38,986 | 5' GTCCTCTCTATGAGGCGAGGGCCCCGGA 3' | 35 |
| ZC38,990 | 5' CGGCGTGCGTAGGAGCCCGCAGGCCAC 3' | 36 |
| ZC39,428 | 5' GGGCTCCTACGCACGCCGCGGCCGAAACC 3' | 37 |
| ZC39,425 | 5' GGAACCACGCGGAACCAGCGCCGCCTCGCCGGC CCCC 3' | 38 |
| ZC39,027 | 5' CTGGTTCCGCGTGGTTCCGAGCCCAAATCTTCA GAC 3' | 39 |
| ZC38,874 | 5' GGCGCGCCTCTAGATTATTTACCCGGAGACA 3' | 40 |

The amplification thermal profile consisted of 94° C. for 3 minutes, 30 cycles at 94° C. for 30 seconds, 55° C. for 30 seconds, 72° C. for 2 minutes, followed by a 4 minute extension at 72° C. The reaction products were fractionated using agarose gel electrophoresis and the bands corresponding to the predicted sizes were excised from the gel and recovered using a QIAGEN QIAQUICK Gel Extraction Kit (Qiagen) according to the manufacturer's instructions.

The second round PCR amplification, or overlap PCR amplification reaction, was performed using the gel-purified fragments from the first round PCR as DNA templates. The conditions of the second round PCR amplification were as follows. To a 50 μl final volume was added 1 μl of each First Round PCR Products 1, 2, 3, and 4, 5 μl 10× Pfu Polymerase Reaction Buffer (Stratagene), 4 μl of 2.5 mM dNTPs, 5 μl Rediload (ResGen), 5 μl GC-Melt Rea (Clontech), approximately 40 pmoles each ZC38,989, ZC38,874 and 0.5 μl Pfu Polymerase (2.5 units, Stratagene). The amplification thermal profile consisted of 94° C. for 3 minutes, 35 cycles at 94° C. for 30 seconds, 55° C. for 30 seconds, 72° C. for 3 minutes, followed by a 6 minute extension at 72° C. The reaction product, designated as "Ztnfr12-tcs-Fc5 PCR," was fractionated using agarose gel electrophoresis, and the band corresponding to the predicted size was excised from the gel and recovered using a QIAGEN QIAQUICK Gel Extraction Kit (Qiagen) according to the manufacturer's instructions.

The Ztnfr12-tcs-Fc5 PCR product was cloned using Invitrogen's ZEROBLUNT TOPO PCR Cloning Kit following the manufacturer's recommended protocol and the DNA sequence was verified. The nucleotide and amino acid sequences of Ztnfr12-tcs-Fc5 are provided as SEQ ID NOs: 41 and 42, respectively. In SEQ ID NO:42, the murine VH 26-10 signal sequence is represented by amino acid residues 1 to 19, a Ztnfr12 extracellular domain is represented by amino acid residues 20 to 90 (i.e., amino acid residues 1 to 71 of SEQ ID NO:2), the thrombin cleavage site is represented by amino acid residues 91 to 96, and the Fc5 immunoglobulin moiety is represented by amino acid residues 97 to 328.

The plasmid encoding the sequence-verified Ztnfr12-tcs-Fc5 was digested with FseI and AscI to release the coding segment. The FseI-AscI fragment was ligated into a mammalian expression vector containing a cytomegalovirus promoter (CMV) promoter, an SV40 poly A segment, and the murine dihydrofolate reductase gene.

Example 5

Production of Ztnfr12-Fc Proteins by Chinese Hamster Ovary Cells

The Ztnfr12-Fc5 expression construct was used to transfect, via electroporation, suspension-adapted Chinese hamster ovary (CHO) DG44 cells grown in animal protein-free medium (Urlaub et al., Som. Cell. Molec. Genet. 12:555 (1986)). CHO DG44 cells lack a functional dihydrofolate reductase gene due to deletions at both dihydrofolate reductase chromosomal locations. Growth of the cells in the presence of increased concentrations of methotrexate results in the amplification of the dihydrofolate reductase gene, and the linked recombinant protein-encoded gene on the expression construct.

CHO DG44 cells were passaged in PFCHO media (JRH Biosciences, Lenexa, Kans.), 4 mM L-Glutamine (JRH Biosciences), and 1× hypothanxine-thymidine supplement (Life Technologies), and the cells were incubated at 37° C. and 5% $CO_2$ in Corning shake flasks at 120 RPM on a rotating shaker platform. The cells were transfected separately with linearized expression plasmids. To ensure sterility, a single ethanol precipitation step was performed on ice for 25 minutes by combining 200 μg of plasmid DNA in an Eppendorf tube with 20 μl of sheared salmon sperm carrier DNA (5'→3' Inc. Boulder, Co., 10 mg/ml), 22 μl of 3M NaOAc (pH 5.2), and 484 μl of 100% ethanol (Gold Shield Chemical Co., Hayward, Calif.). After incubation, the tube was centrifuged at 14,000 RPM in a microfuge placed in a 4° C. cold room, the supernatant removed and the pellet washed twice with 0.5 ml of 70% ethanol and allowed to air dry.

The CHO DG44 cells were prepared while the DNA pellet was drying by centrifuging $10^6$ total cells (16.5 ml) in a 25 ml conical centrifuge tube at 900 RPM for five minutes. The CHO DG44 cells were resuspended into a total volume of 300 μl of PFCHO growth media, and placed in a Gene-Pulser Cuvette with a 0.4 cm electrode gap (Bio-Rad). The DNA, after approximately 50 minutes of drying time, was resuspended into 500 μl of PFCHO growth media and added to the cells in the cuvette so that the total volume did not exceed 800

□l and was allowed to sit at room temperature for five minutes to decrease bubble formation. The cuvette was placed in a BioRad Gene Pulser II unit set at 0.296 kV (killiVolts) and 0.950 HC (high capacitance) and electroporated immediately.

The cells were incubated five minutes at room temperature before placement in 20 ml total volume of PFCHO media in a CoStar T-75 flask. The flask was placed at 37° C. and 5% $CO_2$ for 48 hours when the cells were then counted by hemocytometer utilizing trypan blue exclusion and put into PFCHO selection media without hypothanxine-thymidine supplement and containing 200 mM methotrexate (Cal Biochem). Upon recovery of the methotrexate selection process, the conditioned media containing the secreted Ztnfr12-Fc5 proteins were examined by Western Blot analysis.

In one study, fusion proteins were purified as follows. Ten liters of conditioned media from CHO cells were clarified and sterile-filtered via passage through a 0.22 □m filter. The filtered medium sample was then applied to a 72 ml protein A column (Poros 50A) for the capture of Ztnfr12-Fc5 target molecule. Flow-through material from the original application was reprocessed twice on the protein A column to enhance maximal recovery. Analysis with non-reducing SDS-PAGE indicated that the bound material recovered at this step was both multimeric and dimeric. After fractionation with reducing SDS-PAGE, only monomeric fusion protein having a molecular weight of 36 kD was observed. The recovered mixture of Ztnfr12-Fc5 species was then applied to a Superdex-200 size exclusion chromatography column (318 ml) to further purify and buffer-exchange the material. This step provided resolution of the dimeric material from the mulitmeric material.

Example 6

Characterization of Ztnfr12-Fc Fusion Proteins

Edman degradation was performed to identify the N-terminus of the Ztnfr12-Fc fusion protein. The results indicate that the N-terminus was digested, and that the first amino acid was $Ser^7$.

Ztnfr12-Fc was digested with thrombin using standard techniques. Briefly, thrombin digestion was performed by adding the thrombin at a 1:25 ratio by weight to protein, and incubating at room temperature for 30 minutes. The reaction was stopped by immediate injection onto reverse-phase HPLC column for the LC separation part of the analysis. The eluate from the reverse phase column was directed into an LCQ mass spectrometer and MS and MS/MS data were collected. Each digest was analyzed with and without reduction and peaks observed to be differentially recovered were identified by mass matching and sequence (MS/MS) confirmation analysis where possible. Thrombin digestion of the protein identified the presence of the following two cleavage sites in the Ztnfr12-domain in addition to the engineered site: $Arg^{39}$-$Thr^{40}$, and $Arg^{54}$-$Thr^{55}$.

Due to the protease resistance of the Fc domain, no glycosylation modifications could be observed for that part of the protein. The single predicted N-linked carbohydrate is in the Fc domain at $Asn^{159}$.

However, numerous heterogeneous O-glycans were observed attached to the Ztnfr12 domain. The fully formed structure of these O-glycans is consistent with previously characterized O-glycans found on proteins recombinantly produced in CHO cells and is a tetra-saccharide of the form, (N-acetyl hexosamine)-(N-acetyl neuramic acid (i.e., sialic acid))-(hexose)-(N-acetyl neuramic acid). The most predominant form observed was the tri-saccharide, (N-acetyl hexosamine)-(hexose)-(N-acetyl neuramic acid). Each site was observed to be partially and heterogeneously occupied with multiple forms of the carbohydrate ranging from a single N-acetyl hexosamine to the fully formed tetra-saccharide. Due to the heterogeneity of the carbohydrates and the incomplete nature of this analysis, a clear assignment of percent site occupancy was not possible. The residues that were observed to be modified at some level were $Thr^{17}$, $Thr^{40}$, $Ser^{49}$, $Ser^{50}$, $Thr^{55}$, and $Ser^{62}$. These carbohydrate modifications distinguish this fusion protein from TACI-FC, which has only a single N-linked carbohydrate in the Fc domain.

Ztnfr12-Fc5 was immobilized to a plate coated with goat anti-human IgG Fc, and incubated with ZTNF4-biotin. The results of this study showed that Ztnfr12-Fc5 binds ZTNF4. Additional studies showed that Ztnfr12-Fc5 inhibited the proliferation of human peripheral blood cells, which had been co-activated with soluble ZTNF4 and recombinant human IL-4, and that Ztnfr12-Fc5 inhibited ZTNF4-biotin binding to soluble TACI receptor.

Example 7

Baculovirus Expression of Soluble Ztnfr12

An expression vector, pZBV37L:sTNFR12cee, was designed to express soluble Ztnfr12 polypeptide (amino acid residues 1 to 71 of SEQ ID NO:2) with a C-terminal "EE" tag (EYMPMD; SEQ ID NO:45), after cleavage of the signal peptide.

A. Construction of pZBV37L:sTNFR12cee

A 257 base pair sTNFR12cee fragment containing BspeI and XbaI restriction sites on the 5' and 3' ends, respectively, was generated by PCR amplification from a plasmid containing Ztnfr12 cDNA, using primers 5' ATGCATTCCG GAATGAGGCG AGGGCCCCGG AGCCTG 3' (SEQ ID NO:43) and 5' ATGCATTCTA GATCAGTCCA TCGGCATGTA TTCCGCCGCC TCGCCGGCCC CCGC 3' (SEQ ID NO:44). The PCR reaction conditions were as follows, using the Expand High Fidelity PCR System (Boehringer Mannheim) for a 100 □l volume reaction containing 10% DMSO: 1 cycle at 94° C. for 2 minutes; 35 cycles of 94° C. for 15 seconds, 50° C. for 30 seconds and 72° C. for 45 seconds; 1 cycle at 72° C. for 5 min; followed by 4° C. soak. Five microliters of the reaction mix were visualized by gel electrophoresis (1% NuSieve agarose). The remainder of the reaction mix was purified via Qiagen PCR purification kit as per manufacturer's instructions and eluted in 30 □l of water. The cDNA was digested in a 35 □l volume using BspeI and XbaI (New England Biolabs, Beverly, Mass.) in appropriate buffer conditions for 1hr at 37° C. The digested PCR product band was run through a 1% agarose TAE gel, excised and extracted using a QIAQUICK Gel Extraction Kit (Qiagen) and eluted in 30 □l of water. The purified, digested sTNFR12cee PCR product was ligated into the MCS of a previously prepared and restriction enzyme digested (BspeI and XbaI) vector pZBV37L.

The pZBV37L vector is a modification of the PFASTBAC1 (Life Technologies) expression vector, where the polyhedron promoter has been removed and replaced with the late activating Basic Protein Promoter and the EGT leader signal sequence upstream of the multiple cloning site. Five microliters of the restriction digested sTNFR12cee and about 50 ng of the corresponding pZBV37L vector were ligated overnight at 16° C. in a 20 □l volume in appropriate buffer conditions. Five microliters of the ligation mix were transformed into 50 □l of ELECTOMAX DH12S cells (Life Technologies) by electroporation at 400 Ohms, 2V and 25 µF in a 2 mm gap electroporation cuvette (BTX). The transformed cells were diluted in 350 µl of SOC media (2% Bacto Tryptone, 0.5% Bacto Yeast Extract, 10 ml 1M NaCl, 1.5 mM KCl, 10 mM MgCl₂, 10 mM MgSO₄ and 20 mM glucose) incubated for one hour at 37° C., and 50 µl of the dilution were plated onto LB plates containing 100 µg/ml ampicillin.

Clones were analyzed by PCR and restriction digestion. Positive clones were selected, plated and submitted for sequencing. Once proper sequence was confirmed, 25 ng of positive clone DNA was transformed into 100 µl DH10BAC MAX EFFICIENCY competent cells (GIBCO-BRL) by heat shock for 45 seconds in a 42° C. heat block. The transformed DH10BAC cells were diluted in 900 µl of SOC media (2% Bacto Tryptone, 0.5% Bacto Yeast Extract, 10 ml 1M NaCl, 1.5 mM KCl, 10 mM MgCl₂, 10 mM MgSO₄ and 20 mM glucose) incubated for 37° C. for one hour, and 100 µl were plated onto Luria Agar plates containing 50 µg/ml kanamycin, 7 µg/ml gentamicin, 10 µg/ml tetracycline, 40 µg/mL IPTG and 200 µg/mL BLUO-GAL (5-bromo-3-indolyl-☐-D-galactopyranoside). The plates were incubated for 48 hours at 37° C. A color selection was used to identify those cells having transposed viral DNA (referred to as a "bacmid"). Those colonies, which were white in color, were picked. Positive white colonies (containing desired bacmid) were selected for outgrowth and subsequent bacmid DNA purification. *Spodoptera Frugiperda* (Sf9) cells were transfected after culture outgrowth and bacmid isolation.

B. Transfection of Sf9 Cells

Sf9 cells were seeded at 1×10⁶ cells per well in a 6-well plate and allowed to attach for 1 hour at 27° C. About 5 ☐g of bacmid DNA were diluted with 100 µl Sf-900 II SFM (Life Technologies). Twenty microliters of LIPOFECTAMINE Reagent (Life Technologies) were diluted with 100 µl of Sf-900 II SFM. The bacmid DNA and lipid solutions were gently mixed and incubated for 45 minutes at room temperature. Eight hundred microliters of Sf-900 II SFM were added to the lipid-DNA mixture. The media was aspirated from the well and the 1 ml of DNA-lipid mix added to the cells. The cells were incubated at 27° C. overnight. The DNA-lipid mix was aspirated and 2 ml of Sf-900 II media were added to each plate. The plates were incubated at 27° C., 90% humidity, for about seven days, and then the virus was harvested.

C. Amplification

Sf9 cells were seeded at 1×10⁶ cells per well in a 6-well plate in 2 ml of SF-900II. Five hundred microliters of virus from the transfection plate were placed in the well, and the plate was incubated at 27° C., 90% humidity, for 96 hours after which the virus was harvested for the primary amplification. Additional amplification can be achieved using the following procedure.

A second round of amplification can proceed as follows: Sf9 cells are seeded at 1×10⁶ cells per well in a 6-well plate in 2 ml of SF-900II. One hundred microliters of virus from the primary amplification plate are placed in the well and the plate is incubated at 27° C., 90% humidity, for 96 hours, and then the virus was harvested to complete the secondary amplification.

An additional round of amplification can be performed. Sf9 cells are grown in 50 ml Sf-900 II SFM in a 250 ml shake flask to an approximate density of 1×10⁶ cells/ml. They are then infected with 500 µl of the viral stock from the above plate and incubated at 27° C. for 3 days after which time the virus is harvested.

This viral stock is titered by a growth inhibition curve and the titer culture that indicated a MOI of 1 is allowed to proceed for a total of 48 hours. The supernatant is analyzed via a non-reduced Western using a primary monoclonal antibody specific for the GFD of zVegf4 (E3595) and a HRP conjugated goat anti-Mu secondary antibody. Results should indicate a dimer band of about 79 kDa and additional higher molecular weight species. Supernatant can also be used for activity analysis.

A large viral stock is generated by the following method: Sf9 cells are grown in 1 L Sf-900 II SFM in a 2800 ml shake flask to an approximate density of 1×10⁶ cells/ml. They are then infected with 10 ml of the viral stock from the last amplification, and incubated at 27° C. for 96 hours, after which time the virus is harvested.

Larger scale infections can be completed to provide material for downstream purification.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated nucleic acid that encodes a polypeptide selected from the group consisting of (a) a polypeptide consisting of amino acid residues 1 to 69 of the amino acid sequence of SEQ ID NO:2, and (b) a polypeptide consisting of amino acid residues 7 to 69 of the amino acid sequence of SEQ ID NO:2.

2. An isolated nucleic acid that encodes a fusion protein consisting of the polypeptide of claim 1 and an immunoglobulin moiety.

3. The nucleic acid of claim 2, wherein said fusion protein consists of amino acid residues 1 to 69 of SEQ ID NO:2 and an immunoglobulin moiety.

4. The nucleic acid of claim 2, wherein said fusion protein consists of amino acid residues 7 to 69 of SEQ ID NO:2 and an immunoglobulin moiety.

5. The nucleic acid of claim 2 wherein said immunoglobulin moiety is a Fc fragment.

6. The nucleic acid of claim 5 wherein said Fc fragment is Fc5.

7. A method of producing a polypeptide selected from the group consisting of (a) a polypeptide consisting of amino acid residues 1 to 69 of the amino acid sequence of SEQ ID NO:2, and a (b) polypeptide consisting of amino acid residues 7 to 69 of the amino acid sequence of SEQ ID NO:2, the method comprising culturing recombinant host cells that comprise an expression vector comprising the nucleic acid of claim 1 and producing the polypeptide.

8. The method of claim 7, further comprising isolating the polypeptide from the cultured recombinant host cells.

* * * * *

SEQUENCE LISTING

```
<160> NUMBER OF SEQ ID NOS: 46

<210> SEQ ID NO 1
<211> LENGTH: 586
<212> TYPE: DNA
<213> ORGANISM: Homo sapiens
<220> FEATURE:
<221> NAME/KEY: CDS
<222> LOCATION: (27)...(578)

<400> SEQUENCE: 1
gcagcttgtg cggcggcgtc ggcacc atg agg cga ggg ccc cgg agc ctg cgg      53
                              Met Arg Arg Gly Pro Arg Ser Leu Arg
                                1               5 ggc agg gac gcg cca gcc ccc acg ccc tgc gtc ccg gcc gag tgc ttc     101
Gly Arg Asp Ala Pro Ala Pro Thr Pro Cys Val Pro Ala Glu Cys Phe
 10              15                  20                  25 gac ctg ctg gtc cgc cac tgc gtg gcc tgc ggg ctc ctg cgc acg ccg     149
Asp Leu Leu Val Arg His Cys Val Ala Cys Gly Leu Leu Arg Thr Pro
             30                  35                  40
```

| | | |
|---|---|---|
| cgg ccg aaa ccg gcc ggg gcc agc agc cct gcg ccc agg acg gcg ctg<br>Arg Pro Lys Pro Ala Gly Ala Ser Ser Pro Ala Pro Arg Thr Ala Leu<br>              45                    50                    55 | | 197 |
| cag ccg cag gag tcg gtg ggc gcg ggg gcc ggc gag gcg gcg ctg ccc<br>Gln Pro Gln Glu Ser Val Gly Ala Gly Ala Gly Glu Ala Ala Leu Pro<br>        60                    65                    70 | | 245 |
| ctg ccc ggg ctg ctc ttt ggc gcc ccc gcg ctg ctg ggc ctg gca ctg<br>Leu Pro Gly Leu Leu Phe Gly Ala Pro Ala Leu Leu Gly Leu Ala Leu<br> 75                    80                    85 | | 293 |
| gtc ctg gcg ctg gtc ctg gtg ggt ctg gtg agc tgg agg cgg cga cag<br>Val Leu Ala Leu Val Leu Val Gly Leu Val Ser Trp Arg Arg Arg Gln<br>      90                    95                  100                 105 | | 341 |
| cgg cgg ctt cgc ggc gcg tcc tcc gca gag gcc ccc gac gga gac aag<br>Arg Arg Leu Arg Gly Ala Ser Ser Ala Glu Ala Pro Asp Gly Asp Lys<br>                    110                    115                    120 | | 389 |
| gac gcc cca gag ccc ctg gac aag gtc atc att ctg tct ccg gga atc<br>Asp Ala Pro Glu Pro Leu Asp Lys Val Ile Ile Leu Ser Pro Gly Ile<br>               125                    130                    135 | | 437 |
| tct gat gcc aca gct cct gcc tgg cct cct cct ggg gaa gac cca gga<br>Ser Asp Ala Thr Ala Pro Ala Trp Pro Pro Pro Gly Glu Asp Pro Gly<br>                    140                    145                    150 | | 485 |
| acc acc cca cct ggc cac agt gtc cct gtg cca gcc aca gag ctg ggc<br>Thr Thr Pro Pro Gly His Ser Val Pro Val Pro Ala Thr Glu Leu Gly<br> 155                    160                    165 | | 533 |
| tcc act gaa ctg gtg acc acc aag acg gcc ggc cct gag caa caa<br>Ser Thr Glu Leu Val Thr Thr Lys Thr Ala Gly Pro Glu Gln Gln<br>170                    175                    180 | | 578 |
| tagcaggg | | 586 |

<210> SEQ ID NO 2
<211> LENGTH: 184
<212> TYPE: PRT
<213> ORGANISM: Homo sapiens

<400> SEQUENCE: 2

Met Arg Arg Gly Pro Arg Ser Leu Arg Gly Arg Asp Ala Pro Ala Pro
1                  5                    10                    15

Thr Pro Cys Val Pro Ala Glu Cys Phe Asp Leu Leu Val Arg His Cys
                20                    25                    30

Val Ala Cys Gly Leu Leu Arg Thr Pro Arg Pro Lys Pro Ala Gly Ala
                  35                    40                    45

Ser Ser Pro Ala Pro Arg Thr Ala Leu Gln Pro Gln Glu Ser Val Gly
    50                    55                    60

Ala Gly Ala Gly Glu Ala Ala Leu Pro Leu Pro Gly Leu Leu Phe Gly
65                  70                    75                    80

Ala Pro Ala Leu Leu Gly Leu Ala Leu Val Leu Ala Leu Val Leu Val
                85                    90                    95

Gly Leu Val Ser Trp Arg Arg Arg Gln Arg Arg Leu Arg Gly Ala Ser
                100                  105                  110

Ser Ala Glu Ala Pro Asp Gly Asp Lys Asp Ala Pro Glu Pro Leu Asp
     115                   120                    125

Lys Val Ile Ile Leu Ser Pro Gly Ile Ser Asp Ala Thr Ala Pro Ala
    130                   135                   140

Trp Pro Pro Pro Gly Glu Asp Pro Gly Thr Thr Pro Pro Gly His Ser
145                150                    155                    160

Val Pro Val Pro Ala Thr Glu Leu Gly Ser Thr Glu Leu Val Thr Thr
            165                 170                 175

Lys Thr Ala Gly Pro Glu Gln Gln
            180

<210> SEQ ID NO 3
<211> LENGTH: 552
<212> TYPE: DNA
<213> ORGANISM: Artificial Sequence
<220> FEATURE:
<223> OTHER INFORMATION: This degenerate nucleotide sequence encodes the
      amino acid sequence of SEQ ID NO:2.
<220> FEATURE:
<221> NAME/KEY: misc_feature
<222> LOCATION: 6, 9, 12, 15, 18, 21, 24, 27, 30, 33, 39, 42, 45, 48,
      51, 54, 60, 63, 66, 81, 84, 87, 90, 99, 102, 108, 111, 114,
      117, 120, 123, 126, 129, 135, 138, 141, 144, 147, 150, 153,
      156, 159, 162, 165, 168, 171, 177, 186, 189, 192, 195, 198
<223> OTHER INFORMATION: n = A,T,C or G
<220> FEATURE:
<221> NAME/KEY: misc_feature
<222> LOCATION: 201, 204, 210, 213, 216, 219, 222, 225, 228, 231, 234,
      240, 243, 246, 249, 252, 255, 258, 261, 264, 267, 270, 273, 276,
      279, 282, 285, 288, 291, 294, 297, 300, 306, 309, 312, 318,
      321, 324, 327, 330, 333, 336, 339, 342, 348, 351, 357
<223> OTHER INFORMATION: n = A,T,C or G
<220> FEATURE:
<221> NAME/KEY: misc_feature
<222> LOCATION: 369, 372, 378, 381, 390, 399, 402, 405, 408, 414, 420,
      423, 426, 429, 432, 438, 441, 444, 447, 456, 459, 462, 465, 468,
      471, 474, 480, 483, 486, 489, 492, 495, 498, 504, 507, 510,
      513, 519, 522, 525, 528, 534, 537, 540, 543
<223> OTHER INFORMATION: n = A,T,C or G

<400> SEQUENCE: 3
atgmgnmgng gnccnmgnws nytnmgnggn mgngaygcnc cngcnccnac nccntgygtn      60
ccngcngart gyttygayyt nytngtnmgn caytgygtng cntgyggnyt nytnmgnacn     120
ccnmgnccna arccngcngg ngcnwsnwsn ccngcnccnm gnacngcnyt ncarccncar     180
garwsngtng gngcnggngc nggngargcn gcnytnccny tnccnggnyt nytnttyggn     240 gnccngcny tnytnggnyt ngcnytngtn ytngcnytng tnytngtngg nytngtnwsn      300
tggmgnmgnm gncarmgnmg nytnmgnggn gcnwsnwsng cngargcncc ngayggngay     360
aargaygcnc cngarccnyt ngayaargtn athathytnw snccnggnat hwsngaygcn     420
acngcnccng cntggccncc nccnggngar gayccnggna cnacnccncc nggncaywsn     480
gtnccngtnc cngcnacnga rytnggnwsn acngarytng tnacnacnaa racngcnggn     540
ccngarcarc ar                                                        552

<210> SEQ ID NO 4
<211> LENGTH: 16
<212> TYPE: PRT
<213> ORGANISM: Artificial Sequence
<220> FEATURE:
<223> OTHER INFORMATION: Peptide linker.

<400> SEQUENCE: 4

Gly Gly Ser Gly Gly Ser Gly Gly Gly Gly Ser Gly Gly Gly Gly Ser
  1               5                  10                  15

<210> SEQ ID NO 5
<211> LENGTH: 285
<212> TYPE: PRT
<213> ORGANISM: Homo sapiens

<400> SEQUENCE: 5

```
Met Asp Asp Ser Thr Glu Arg Glu Gln Ser Arg Leu Thr Ser Cys Leu
  1               5                  10                 15

Lys Lys Arg Glu Glu Met Lys Leu Lys Glu Cys Val Ser Ile Leu Pro
             20                 25                 30

Arg Lys Glu Ser Pro Ser Val Arg Ser Ser Lys Asp Gly Lys Leu Leu
             35                 40                 45

Ala Ala Thr Leu Leu Ala Leu Leu Ser Cys Cys Leu Thr Val Val
 50                 55                 60

Ser Phe Tyr Gln Val Ala Ala Leu Gln Gly Asp Leu Ala Ser Leu Arg
 65                 70                 75                 80

Ala Glu Leu Gln Gly His His Ala Glu Lys Leu Pro Ala Gly Ala Gly
                 85                 90                 95

Ala Pro Lys Ala Gly Leu Glu Glu Ala Pro Ala Val Thr Ala Gly Leu
            100                105                110

Lys Ile Phe Glu Pro Pro Ala Pro Gly Glu Gly Asn Ser Ser Gln Asn
            115                120                125

Ser Arg Asn Lys Arg Ala Val Gln Gly Pro Glu Glu Thr Val Thr Gln
130                135                140

Asp Cys Leu Gln Leu Ile Ala Asp Ser Glu Thr Pro Thr Ile Gln Lys
145                150                155                160

Gly Ser Tyr Thr Phe Val Pro Trp Leu Leu Ser Phe Lys Arg Gly Ser
                165                170                175

Ala Leu Glu Glu Lys Glu Asn Lys Ile Leu Val Lys Glu Thr Gly Tyr
            180                185                190

Phe Phe Ile Tyr Gly Gln Val Leu Tyr Thr Asp Lys Thr Tyr Ala Met
            195                200                205

Gly His Leu Ile Gln Arg Lys Lys Val His Val Phe Gly Asp Glu Leu
210                215                220

Ser Leu Val Thr Leu Phe Arg Cys Ile Gln Asn Met Pro Glu Thr Leu
225                230                235                240

Pro Asn Asn Ser Cys Tyr Ser Ala Gly Ile Ala Lys Leu Glu Glu Gly
                245                250                255

Asp Glu Leu Gln Leu Ala Ile Pro Arg Glu Asn Ala Gln Ile Ser Leu
            260                265                270

Asp Gly Asp Val Thr Phe Phe Gly Ala Leu Lys Leu Leu
            275                280                285
```

<210> SEQ ID NO 6
<211> LENGTH: 250
<212> TYPE: PRT
<213> ORGANISM: Homo sapiens

<400> SEQUENCE: 6

```
Met Pro Ala Ser Ser Pro Phe Leu Leu Ala Pro Lys Gly Pro Pro Gly
  1               5                  10                 15

Asn Met Gly Gly Pro Val Arg Glu Pro Ala Leu Ser Val Ala Leu Trp
             20                 25                 30

Leu Ser Trp Gly Ala Ala Leu Gly Ala Val Ala Cys Ala Met Ala Leu
             35                 40                 45

Leu Thr Gln Gln Thr Glu Leu Gln Ser Leu Arg Arg Glu Val Ser Arg
 50                 55                 60

Leu Gln Gly Thr Gly Gly Pro Ser Gln Asn Gly Glu Gly Tyr Pro Trp
 65                 70                 75                 80
```

```
Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 7
<211> LENGTH: 184
<212> TYPE: PRT
<213> ORGANISM: Homo sapiens

<400> SEQUENCE: 7

Met Leu Gln Met Ala Gly Gln Cys Ser Gln Asn Glu Tyr Phe Asp Ser
  1               5                  10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
 50                  55                  60

Ile Ile Ser Leu Ala Val Phe Val Leu Met Phe Leu Leu Arg Lys Ile
65                  70                  75                  80

Ser Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180
```

```
<210> SEQ ID NO 8
<211> LENGTH: 293
<212> TYPE: PRT
<213> ORGANISM: Homo sapiens

<400> SEQUENCE: 8

Met Ser Gly Leu Gly Arg Ser Arg Arg Gly Arg Ser Arg Val Asp
 1               5                  10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
            35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
            180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
    210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
            260                 265                 270

His Ile Pro Asp Ser Gly Leu Gly Ile Val Cys Val Pro Ala Gln Glu
        275                 280                 285

Gly Gly Pro Gly Ala
    290

<210> SEQ ID NO 9
<211> LENGTH: 5759
<212> TYPE: DNA
<213> ORGANISM: Homo sapiens
<220> FEATURE:
<221> NAME/KEY: exon
<222> LOCATION: (1001)...(1136)
<220> FEATURE:
<221> NAME/KEY: exon
<222> LOCATION: (1443)...(1673)
<220> FEATURE:
<221> NAME/KEY: exon
<222> LOCATION: (2220)...(2404)
```

<400> SEQUENCE: 9

```
taatcccagc actttgggag gccgaggagg gcggatcacc tgaggtcagg agttcgagac      60
cagcctggcc aaatggtgaa accccacctc tactaaaaat acaaaaatta gccgggcatg     120
gtggtgcatg cctgtaatcc cagttactcg ggaggctgag gcaggagaat cgcttgaatc     180
tgggaggcag aggttgcagt gagccgagat tgcaccactg cacagagcca gactcttttt     240
caaaaaaaaa aaaaaaaaa gcaggtgtct gatatcccca accagctctg tccaggaagg     300
gcaggaagag aggaggagac aggtggggttg ggggagatgg caggggagca ctcggggtca     360
tggagaggct ttggctagac ggagcagagg aaccactcag ggtctgtgtc ctggctgcgg     420
ggtccatccc cctccctacc aagaggagg ctctggtctg ccccagaca cctcccagca     480
cccagcagag ggcccaccca ggcggtgctg gttgaggggc tgaattgggg aaccacaggt     540
agaaagagag gccaggccgg gtgcggtggc tcacgcctgt aatcctagca ctttgggagg     600
ccgaggcagg tggatcacga ggtcaggagt tcaaaaccag tctgaccaag atggtgaaac     660
cccgtctcta ctaaaaatac aaaaattagc cgggcgtggc agtgggcgcc tacaatctca     720
gctactcggg aggctgaggc agagaattgt ttgaacccgg gaggcagagc ttgcagtgag     780
ccgagatagc gccattgcac tccagcctgg gcgacagagc gagactccgt ctcaaaaaaa     840
aaaaagaaa agaaggggg gccccaggcg agctcggtcc cacccagcag gcgggggcgg     900
ggcagggcag agtgctcccc ccgcccccg cttcctcccc gagggccccg gagcccagct     960
cagcctcagt ccccgcagct tgtgcggcgg cgtcggcacc atgaggcgag ggccccggag    1020
cctgcggggc agggacgcgc cagcccccac gccctgcgtc ccggccgagt gcttcgacct    1080
gctggtccgc cactgcgtgg cctgcgggct cctgcgcacg ccgcggccga aaccgggtaa    1140
ggggggaccca cggggcgcgc ggcgccggca gctgcgggga gaacggggcc ccgatcgcca    1200
gggcgcaggc agagcccgga cccccgggg gcgccgagggc tgaaaggacc ctgtgggcag    1260
ggcctggagg ggcccgcgat caccgcgtgg ccctcaccgc cgcctctctc cctcccttg    1320
tccaccgccc cccggctgtc cctccccctcc ccggccagcc tcgccccccct ccgccctcc    1380
ccgtccccgc tcctccctcc cctcggcccc ctggcctccc tccctgtccc ctcccgaagc    1440
agccggggcc agcagccctg cgcccaggac ggcgctgcag ccgcaggagt cggtgggcgc    1500
gggggccggc gaggcggcgc tgcccctgcc cgggctgctc tttggcgccc ccgcgctgct    1560
gggcctggca ctggtcctgg cgctggtcct ggtgggtctg gtgagctgga gcggcgaca    1620
gcggcggctt cgcggcgcgt cctccgcaga ggcccccgac ggagacaagg acggtgagtt    1680
ccgtgtgtag gggaaccagt ctgagcgggg cgcagggct ggggtgtcgg gacggtctag    1740
ggggagatgc atggccctg aggggagag aagggcttta aggggaaacg agacagagt    1800
ggaaaagagt ttgcgctgag gagctcaggc tggggaggga gacatagtcc tgcccctgag    1860
accctggtcg gagccaggaa cagctctgcc ctgacagacc ccagtgtgag gaagagacag    1920
gttgcaggaa ggggcccccg tctgagggag gagtctgtcc tgccctttgg gagtctaacg    1980
gagcttggtt cccccataaa tccctgaaga gtttgccaga ctgagcccca gctccccaac    2040
tccctgccct gccagctccc cactggccag gcctctggac tcagggtcag ccaggtgcca    2100
cccctcccca ccctgcattg ggcttcattt gacggaggac tgcccctcca gaggagtctt    2160
ctaggggagg gagggaaggc tgtgactgag tacggagcct ctaccccctc tgcctgcagc    2220
cccagagccc ctggacaagg tcatcattct gtctccggga atctctgatg ccacagctcc    2280
tgcctggcct cctcctgggg aagacccagg aaccaccca cctggcccaca gtgtccctgt    2340
```

```
gccagccaca gagctgggct ccactgaact ggtgaccacc aagacggccg gccctgagca    2400
acaatagcag ggagccggca ggaggtggcc cctgccctcc ctctggaccc ccagccaggg    2460
gcttggaaat caaattcagc tcttcactcc agcatgcaca tgccctcttt ctgggaccag    2520
gctaactctg cagaagcaca gacactacag accacagcat tcagccccca tggagtttgg    2580
tgtgcttgcc tttggcttca gacctcacca tctttgacag cccttgaagg tggtagccca    2640
gctcctgttc ctgtgccttc aaaaggctgg ggcactatga gtaaaagacc gcttttaaaa    2700
tggggaaggc accattaagc caaaatgaat ctgaaaaaag accaagtggg aggatgccta    2760
atttgtagtt gggtggtttt ttgtgtttgt ttgatttttt tttttttttt tttttttttt    2820
ttttgagacg agtcttgctc tgtcgccagg ctggagtaca gtggcgcgat ctcgcctcac    2880
tgtaacctcc gactccttgg ttcaagtgat tctcctgcct cagcctcccg aatagctggg    2940
attacaggca cgcaccacca cagccagcta attttttgtat ttttagtaga cgggattt    3000 caccatgttg gccaggatgg tctcgatctc ctgacctcgt gatccgccct gctcggcctc    3060
ccaaagtgct gggattacag gcatgagcca ccatgcccgg cctgttttg tgttttggtt    3120 tttttgaga cagggtcttg ctgtatcacg caggctggag tgcaacgatg gtccccagc    3180 taattgcagc ctgggctcaa gcaatctttc tgcttcagcc tcctgagtag gtgggactac    3240
aggtgctcca ccttgcccag ctaatttttt tttttttttt tttttgaga cagagtctcg    3300 ctctgtcgcc taggctggag tgcagtgacg caatttcggc tcacttcaag ctccgcctcc    3360
tgggttcaca ccattctcct gcctgagcct cctgagtagc tgggactata gcgcccgcc    3420 atcacgcccg gctaattttt tttgtatttt tagtagagac ggggtgtcac cgtattagcc    3480
aggatggtct cgatctcctg acctcgtgat ccgcccgcct cagcctccca aagtgctagg    3540
attacaggcg tgagccaccg tggctggcct tttttttttt ttaaagacag ggtctcggta    3600
tgttgcccag gccagtctca aactcctggc ctcaggcagt cctccccgaa gggctgggat    3660
tataggcagg aggcgccggg cctggcctct atttctttaa tacctgccct cagagccgtc    3720
ctgcttttaa actgatgcaa atggcagcag tgaataatca attcatgggt tcgcttgctt    3780
tgggatttag tacaagatta ttttaagaaa taacaaagga gaaagattg agctggattt    3840 tgctgattct caggtatctg taccccaggg tcaaccctga gattggccca atctgccaga    3900
acctaagatg ccatttgac cccagtggca gcttccagag ccacaagcct gcatttggga    3960
ggaggtgcgc agcctccagg gctgactcc aaactcgagc tgaaggaaca tgctggcagg    4020
tagctctctc agggtccacc tggggttcca gctgctccaa gacacagcac atttagccat    4080
aaacatggaa gggctgggac ctacaggagg ctccttgtg tagaggccag ggcaggcgtg    4140
tgaccttgaa ccaggtggac atgaggtccc ttgaactccc ttctctctct ggcttgttcc    4200
cctgaagcac tggcccccca gtgctgggct tatttggcca tcctgtgcca gcccctggt    4260 cacccaccgt cacagtggaa gctgctccct cctcttacaa tggtgttcct tgctctgggg    4320
tctggggaca agaccatctc tttccactcc tggacgacac tgtgcactca gtcagccgcc    4380
tcctacctgc cctcctgcac agggtcagaa cctcctgacc tggacttcgc cctgggcagc    4440
ttccttggaa cttgttgcag cttagcatct ttggaaggga gcactggact aggagtcaga    4500
aggtggagtt ctgggtgctg ttttcccact cttgggccct gggcatgttc tgttctgtgc    4560
atcagatgtt ttctgcctgc ctccccctga gctgccacca gagccacctg tagacccctg    4620
cttctcctgc ccctcctgtc ccttgccagg cctctggact cagtgcttcc tgtcccaagg    4680
acctgttgtg tgcccagctt ggaagacagt ggccactcac atccaggtct ctgcctggct    4740
```

-continued

```
atttgctcca tgaacccatc tcagatgccc ctgcccccag ggagccaggt gacagggtga      4800
ggtcaagtga caagcagtag gtgtgggaga ggtttggtgg ggtcaggccc acatgggccc      4860
agccatccac tccccttcca tctggagttg ggggagtctg agctgctcct ggccacccca      4920
tctgccccac cccatctttt cctggccacc ccagctccca ccccatcttc tcctggccac      4980
cccatctccc accccatctt ctcttgacac cccatctccc accccatctt ctcctggcca      5040
ccccatctcc caccccatct tctcctggcc accccatctt ctcctggcca ccccatctcc      5100
cccaccccat cttctcctgg acaccccat ctcccacccc atcttttgct acagccaggg       5160
ttagctcagc aggtgaaaac cccgagggtg ggtgaaaccc ctctgggct cagacatgca       5220 aaccttgggc atctctctgt cccagctggc cccgccagcc ggtaggaagt ttcccctgag      5280
ttctcagttt tttcttctga aaatgaggg gttgtatgca aggttctcct cctggcctgt       5340
ggtccccaga gaagggcagg aaggaacctt agataattct catatgcatt taacagacga      5400
ggaaactgag acccagagcc gtcacatcaa tacctcattt gatcttcata agagcacctg      5460 gaggagggggg gtggggtgtt tgtgtttgtt taaattttt tttgtgaaaa aatgaagat        5520 aggcattttg tagacaatct ggaagttctg gaccggaatc catgatgtag tcagggaaga      5580
aatgacccgt gtccagtaac cccaggcctc gagtgtgtgg tgtattttc tacataattg      5640 taatcattct atacatacaa attcatgtct tgaccatcat attaatattt ggtaagtttc      5700
tctctcttta gagactccac aataaagttt tcaacatggt aaggttttcc acctgggca       5759
```

<210> SEQ ID NO 10
<211> LENGTH: 29
<212> TYPE: DNA
<213> ORGANISM: Artificial Sequence
<220> FEATURE:
<223> OTHER INFORMATION: PCR primer.

<400> SEQUENCE: 10
gcgaattcgt cggcaccatg aggcgaggg                                         29

<210> SEQ ID NO 11
<211> LENGTH: 31
<212> TYPE: DNA
<213> ORGANISM: Artificial Sequence
<220> FEATURE:
<223> OTHER INFORMATION: PCR primer.

<400> SEQUENCE: 11
cgctcgagct gccggctccc tgctattgtt g                                      31

<210> SEQ ID NO 12
<211> LENGTH: 685
<212> TYPE: DNA
<213> ORGANISM: Mouse
<220> FEATURE:
<221> NAME/KEY: CDS
<222> LOCATION: (36)...(560)

<400> SEQUENCE: 12
gaattcgccc ttcccagct gcatgaggcg cgac atg ggc gcc agg aga ctc            53
                                   Met Gly Ala Arg Arg Leu
                                    1               5 cgg gtc cga agc cag agg agc cgg gac agc tcg gtg ccc acc cag tgc        101
Arg Val Arg Ser Gln Arg Ser Arg Asp Ser Ser Val Pro Thr Gln Cys
         10                  15                  20

```
aat cag acc gag tgc ttc gac cct ctg gtg aga aac tgc gtg tcc tgt      149
Asn Gln Thr Glu Cys Phe Asp Pro Leu Val Arg Asn Cys Val Ser Cys
        25                  30                  35 gag ctc ttc cac acg ccg gac act gga cat aca agc agc ctg gag cct      197
Glu Leu Phe His Thr Pro Asp Thr Gly His Thr Ser Ser Leu Glu Pro
 40                  45                  50 ggg aca gct ctg cag cct cag gag ggc tcc gcg ctg aga ccc gac gtg      245
Gly Thr Ala Leu Gln Pro Gln Glu Gly Ser Ala Leu Arg Pro Asp Val
 55                  60                  65                  70 gcg ctg ctc gtc ggt gcc ccc gca ctc ctg gga ctg ata ctg gcg ctg      293
Ala Leu Leu Val Gly Ala Pro Ala Leu Leu Gly Leu Ile Leu Ala Leu
                 75                  80                  85 acc ctg gtg ggt cta gtg agt ctg gtg agc tgg agg tgg cgt caa cag      341
Thr Leu Val Gly Leu Val Ser Leu Val Ser Trp Arg Trp Arg Gln Gln
         90                  95                 100 ctc agg acg gcc tcc cca gac act tca gaa gga gtc cag caa gag tcc      389
Leu Arg Thr Ala Ser Pro Asp Thr Ser Glu Gly Val Gln Gln Glu Ser
     105                 110                 115 ctg gaa aat gtc ttt gta ccc tcc tca gaa acc cct cat gcc tca gct      437
Leu Glu Asn Val Phe Val Pro Ser Ser Glu Thr Pro His Ala Ser Ala
 120                 125                 130 cct acc tgg cct ccg ctc aaa gaa gat gca gac agc gcc ctg cca cgc      485
Pro Thr Trp Pro Pro Leu Lys Glu Asp Ala Asp Ser Ala Leu Pro Arg
135                 140                 145                 150 cac agc gtc ccg gtg ccc gcc aca gaa ctg ggc tcc acc gag ctg gtg      533
His Ser Val Pro Val Pro Ala Thr Glu Leu Gly Ser Thr Glu Leu Val
                155                 160                 165 acc acc aag aca gct ggc cca gag caa tagcagcagt ggaggctgga            580
Thr Thr Lys Thr Ala Gly Pro Glu Gln
                170                 175 acccagggat ctctactggg cttgtggact tcacccaaca gcttgggaaa gaacttggcc    640
cttcagtgac ggagtccttt gcctgggggg cgaaagggcg aattc                    685

<210> SEQ ID NO 13
<211> LENGTH: 175
<212> TYPE: PRT
<213> ORGANISM: Mouse

<400> SEQUENCE: 13

Met Gly Ala Arg Arg Leu Arg Val Arg Ser Gln Arg Ser Arg Asp Ser
 1               5                  10                  15

Ser Val Pro Thr Gln Cys Asn Gln Thr Glu Cys Phe Asp Pro Leu Val
                 20                  25                  30

Arg Asn Cys Val Ser Cys Glu Leu Phe His Thr Pro Asp Thr Gly His
         35                  40                  45

Thr Ser Ser Leu Glu Pro Gly Thr Ala Leu Gln Pro Gln Glu Gly Ser
     50                  55                  60

Ala Leu Arg Pro Asp Val Ala Leu Leu Val Gly Ala Pro Ala Leu Leu
 65                  70                  75                  80

Gly Leu Ile Leu Ala Leu Thr Leu Val Gly Leu Val Ser Leu Val Ser
                 85                  90                  95

Trp Arg Trp Arg Gln Gln Leu Arg Thr Ala Ser Pro Asp Thr Ser Glu
            100                 105                 110

Gly Val Gln Gln Glu Ser Leu Glu Asn Val Phe Val Pro Ser Ser Glu
        115                 120                 125

Thr Pro His Ala Ser Ala Pro Thr Trp Pro Pro Leu Lys Glu Asp Ala
    130                 135                 140
```

Asp Ser Ala Leu Pro Arg His Ser Val Pro Val Pro Ala Thr Glu Leu
145                 150                 155                 160

Gly Ser Thr Glu Leu Val Thr Thr Lys Thr Ala Gly Pro Glu Gln
                165                 170                 175

<210> SEQ ID NO 14
<211> LENGTH: 525
<212> TYPE: DNA
<213> ORGANISM: Artificial Sequence
<220> FEATURE:
<223> OTHER INFORMATION: This degenerate nucleotide sequence encodes the
      amino acid sequence of SEQ ID NO:13.
<220> FEATURE:
<221> NAME/KEY: misc_feature
<222> LOCATION: 6, 9, 12, 15, 18, 21, 24, 27, 30, 36, 39, 42, 48, 51,
      54, 57, 60, 75, 90, 93, 96, 99, 108, 111, 120, 129, 132, 138,
      141, 147, 150, 153, 156, 162, 165, 168, 171, 174, 180, 189,
      192, 195, 198, 201, 204, 210, 213, 216, 219, 222, 225
<223> OTHER INFORMATION: n = A,T,C or G
<220> FEATURE:
<221> NAME/KEY: misc_feature
<222> LOCATION: 228, 231, 234, 237, 240, 243, 246, 252, 255, 258, 261,
      264, 267, 270, 273, 276, 279, 282, 285, 288, 294, 300, 309, 312,
      315, 318, 321, 324, 330, 333, 339, 342, 354, 357, 366, 372,
      375, 378, 381, 387, 390, 396, 399, 402, 405, 408, 414
<223> OTHER INFORMATION: n = A,T,C or G
<220> FEATURE:
<221> NAME/KEY: misc_feature
<222> LOCATION: 417, 420, 432, 438, 441, 444, 447, 450, 456, 459, 462,
      465, 468, 471, 474, 480, 483, 486, 489, 495, 498, 501, 504, 510,
      513, 516, 519
<223> OTHER INFORMATION: n = A,T,C or G

<400> SEQUENCE: 14
atgggngcnm gnmgnytnmg ngtnmgnwsn carmgnwsnm gngaywsnws ngtnccnacn      60
cartgyaayc aracngartg yttygayccn ytngtnmgna aytgygtnws ntgygarytn     120
ttycayacnc cngayacngg ncayacnwsn wsnytngarc cnggnacngc nytncarccn     180
cargarggnw sngcnytnmg nccngaygtn gcnytnytng tnggngcncc ngcnytnytn     240
ggnytnathy tngcnytnac nytngtnggn ytngtnwsny tngtnwsntg gmgntggmgn     300
carcarytnm gnacngcnws nccngayacn wsngarggng tncarcarga rwsnytngar    360
aaygtnttyg tnccnwsnws ngaracnccn caygcnwsng cnccnacntg gccnccnytn     420
aargargayg cngaywsngc nytnccnmgn caywsngtnc cngtnccngc nacngarytn     480
ggnwsnacng arytngtnac nacnaaracn gcnggnccng arcar                     525

<210> SEQ ID NO 15
<211> LENGTH: 44
<212> TYPE: DNA
<213> ORGANISM: Artificial Sequence
<220> FEATURE:
<223> OTHER INFORMATION: PCR primer.

<400> SEQUENCE: 15
atcagcggaa ttcagatctt cagacaaaac tcacacatgc ccac                      44

<210> SEQ ID NO 16
<211> LENGTH: 35
<212> TYPE: DNA
<213> ORGANISM: Artificial Sequence
<220> FEATURE:
<223> OTHER INFORMATION: PCR primer.

<400> SEQUENCE: 16
ggcagtctct agatcattta cccggagaca gggag                                35

<210> SEQ ID NO 17
<211> LENGTH: 762
<212> TYPE: DNA
<213> ORGANISM: Homo sapiens
<220> FEATURE:
<221> NAME/KEY: CDS
<222> LOCATION: (7)...(759)

<400> SEQUENCE: 17

```
ggatcc atg aag cac ctg tgg ttc ttc ctc ctg ctg gtg gcg gct ccc         48
       Met Lys His Leu Trp Phe Phe Leu Leu Leu Val Ala Ala Pro
        1               5                  10 aga tgg gtc ctg tcc gag ccc aaa tct tgt gac aaa act cac aca tgc         96
Arg Trp Val Leu Ser Glu Pro Lys Ser Cys Asp Lys Thr His Thr Cys
 15                  20                  25                  30 cca ccg tgc cca gca cct gaa ctc ctg ggg gga ccg tca gtc ttc ctc        144
Pro Pro Cys Pro Ala Pro Glu Leu Leu Gly Gly Pro Ser Val Phe Leu
                     35                  40                  45 ttc ccc cca aaa ccc aag gac acc ctc atg atc tcc cgg acc cct gag        192
Phe Pro Pro Lys Pro Lys Asp Thr Leu Met Ile Ser Arg Thr Pro Glu
         50                  55                  60 gtc aca tgc gtg gtg gtg gac gtg agc cac gaa gac cct gag gtc aag        240
Val Thr Cys Val Val Val Asp Val Ser His Glu Asp Pro Glu Val Lys
     65                  70                  75 ttc aac tgg tac gtg gac ggc gtg gag gtg cat aat gcc aag aca aag        288
Phe Asn Trp Tyr Val Asp Gly Val Glu Val His Asn Ala Lys Thr Lys
 80                  85                  90 ccg cgg gag gag cag tac aac agc acg tac cgt gtg gtc agc gtc ctc        336
Pro Arg Glu Glu Gln Tyr Asn Ser Thr Tyr Arg Val Val Ser Val Leu
 95                 100                 105                 110 acc gtc ctg cac cag gac tgg ctg aat ggc aag gag tac aag tgc aag        384
Thr Val Leu His Gln Asp Trp Leu Asn Gly Lys Glu Tyr Lys Cys Lys
                    115                 120                 125 gtc tcc aac aaa gcc ctc cca gcc ccc atc gag aaa acc atc tcc aaa        432
Val Ser Asn Lys Ala Leu Pro Ala Pro Ile Glu Lys Thr Ile Ser Lys
        130                 135                 140 gcc aaa ggg cag ccc cga gaa cca cag gtg tac acc ctg ccc cca tcc        480
Ala Lys Gly Gln Pro Arg Glu Pro Gln Val Tyr Thr Leu Pro Pro Ser
    145                 150                 155 cgg gat gag ctg acc aag aac cag gtc agc ctg acc tgc ctg gtc aaa        528
Arg Asp Glu Leu Thr Lys Asn Gln Val Ser Leu Thr Cys Leu Val Lys
160                 165                 170 ggc ttc tat ccc agc gac atc gcc gtg gag tgg gag agc aat ggg cag        576
Gly Phe Tyr Pro Ser Asp Ile Ala Val Glu Trp Glu Ser Asn Gly Gln
175                 180                 185                 190 ccg gag aac aac tac aag acc acg cct ccc gtg ctg gac tcc gac ggc        624
Pro Glu Asn Asn Tyr Lys Thr Thr Pro Pro Val Leu Asp Ser Asp Gly
                195                 200                 205 tcc ttc ttc ctc tac agc aag ctc acc gtg gac aag agc agg tgg cag        672
Ser Phe Phe Leu Tyr Ser Lys Leu Thr Val Asp Lys Ser Arg Trp Gln
        210                 215                 220 cag ggg aac gtc ttc tca tgc tcc gtg atg cat gag gct ctg cac aac        720
Gln Gly Asn Val Phe Ser Cys Ser Val Met His Glu Ala Leu His Asn
    225                 230                 235 cac tac acg cag aag agc ctc tcc ctg tct ccg ggt aaa tga                762
His Tyr Thr Gln Lys Ser Leu Ser Leu Ser Pro Gly Lys
240                 245                 250
```

<210> SEQ ID NO 18
<211> LENGTH: 251
<212> TYPE: PRT
<213> ORGANISM: Homo sapiens

<400> SEQUENCE: 18

| | | | | | | | | | | | | | | | |
|---|---|---|---|---|---|---|---|---|---|---|---|---|---|---|---|
|Met|Lys|His|Leu|Trp|Phe|Phe|Leu|Leu|Leu|Val|Ala|Ala|Pro|Arg|Trp|
|1| | | |5| | | | |10| | | | |15| |
|Val|Leu|Ser|Glu|Pro|Lys|Ser|Cys|Asp|Lys|Thr|His|Thr|Cys|Pro|Pro|
| | | |20| | | | |25| | | | |30| | |
|Cys|Pro|Ala|Pro|Glu|Leu|Leu|Gly|Gly|Pro|Ser|Val|Phe|Leu|Phe|Pro|
| | |35| | | | |40| | | | |45| | | |
|Pro|Lys|Pro|Lys|Asp|Thr|Leu|Met|Ile|Ser|Arg|Thr|Pro|Glu|Val|Thr|
| |50| | | | |55| | | | |60| | | | |
|Cys|Val|Val|Val|Asp|Val|Ser|His|Glu|Asp|Pro|Glu|Val|Lys|Phe|Asn|
|65| | | |70| | | | |75| | | | |80| |
|Trp|Tyr|Val|Asp|Gly|Val|Glu|Val|His|Asn|Ala|Lys|Thr|Lys|Pro|Arg|
| | | | |85| | | | |90| | | | |95| |
|Glu|Glu|Gln|Tyr|Asn|Ser|Thr|Tyr|Arg|Val|Val|Ser|Val|Leu|Thr|Val|
| | | |100| | | | |105| | | | |110| | |
|Leu|His|Gln|Asp|Trp|Leu|Asn|Gly|Lys|Glu|Tyr|Lys|Cys|Lys|Val|Ser|
| | |115| | | | |120| | | | |125| | | |
|Asn|Lys|Ala|Leu|Pro|Ala|Pro|Ile|Glu|Lys|Thr|Ile|Ser|Lys|Ala|Lys|
| |130| | | | |135| | | | |140| | | | |
|Gly|Gln|Pro|Arg|Glu|Pro|Gln|Val|Tyr|Thr|Leu|Pro|Pro|Ser|Arg|Asp|
|145| | | |150| | | | |155| | | | |160| |
|Glu|Leu|Thr|Lys|Asn|Gln|Val|Ser|Leu|Thr|Cys|Leu|Val|Lys|Gly|Phe|
| | | |165| | | | |170| | | | |175| | |
|Tyr|Pro|Ser|Asp|Ile|Ala|Val|Glu|Trp|Glu|Ser|Asn|Gly|Gln|Pro|Glu|
| | |180| | | | |185| | | | |190| | | |
|Asn|Asn|Tyr|Lys|Thr|Thr|Pro|Pro|Val|Leu|Asp|Ser|Asp|Gly|Ser|Phe|
| |195| | | | |200| | | | |205| | | | |
|Phe|Leu|Tyr|Ser|Lys|Leu|Thr|Val|Asp|Lys|Ser|Arg|Trp|Gln|Gln|Gly|
|210| | | | |215| | | | |220| | | | | |
|Asn|Val|Phe|Ser|Cys|Ser|Val|Met|His|Glu|Ala|Leu|His|Asn|His|Tyr|
|225| | | |230| | | | |235| | | | |240| |
|Thr|Gln|Lys|Ser|Leu|Ser|Leu|Ser|Pro|Gly|Lys| | | | | |
| | | |245| | | | |250| | | | | | | |

<210> SEQ ID NO 19
<211> LENGTH: 51
<212> TYPE: DNA
<213> ORGANISM: Artificial Sequence
<220> FEATURE:
<223> OTHER INFORMATION: PCR primer.

<400> SEQUENCE: 19
ccgtgcccag cacctgaagc cgaggggggca ccgtcagtct tcctcttccc c          51

<210> SEQ ID NO 20
<211> LENGTH: 31
<212> TYPE: DNA
<213> ORGANISM: Artificial Sequence
<220> FEATURE:
<223> OTHER INFORMATION: PCR primer.

<400> SEQUENCE: 20
ggattctaga ttatttaccc ggagacaggg a                                 31

<210> SEQ ID NO 21
<211> LENGTH: 55
<212> TYPE: DNA
<213> ORGANISM: Artificial Sequence -continued
<220> FEATURE:
<223> OTHER INFORMATION: PCR primer.

<400> SEQUENCE: 21
ggtggcggct cccagatggg tcctgtccga gcccagatct tcagacaaaa ctcac    55

<210> SEQ ID NO 22
<211> LENGTH: 18
<212> TYPE: DNA
<213> ORGANISM: Artificial Sequence
<220> FEATURE:
<223> OTHER INFORMATION: PCR primer.

<400> SEQUENCE: 22
tgggagggct tgttgga    18

<210> SEQ ID NO 23
<211> LENGTH: 42
<212> TYPE: DNA
<213> ORGANISM: Artificial Sequence
<220> FEATURE:
<223> OTHER INFORMATION: PCR primer.

<400> SEQUENCE: 23
tccaacaaag ccctcccatc ctccatcgag aaaaccatct cc    42

<210> SEQ ID NO 24
<211> LENGTH: 47
<212> TYPE: DNA
<213> ORGANISM: Artificial Sequence
<220> FEATURE:
<223> OTHER INFORMATION: PCR primer.

<400> SEQUENCE: 24
atgaagcacc tgtggttctt cctcctgctg gtggcggctc ccagatg    47

<210> SEQ ID NO 25
<211> LENGTH: 57
<212> TYPE: DNA
<213> ORGANISM: Artificial Sequence
<220> FEATURE:
<223> OTHER INFORMATION: PCR primer.

<400> SEQUENCE: 25
ggatggatcc atgaagcacc tgtggttctt cctcctgctg gtggcggctc ccagatg    57

<210> SEQ ID NO 26
<211> LENGTH: 31
<212> TYPE: DNA
<213> ORGANISM: Artificial Sequence
<220> FEATURE:
<223> OTHER INFORMATION: PCR primer.

<400> SEQUENCE: 26
ggattctaga ttatttaccc ggagacaggg a    31

<210> SEQ ID NO 27
<211> LENGTH: 718
<212> TYPE: DNA
<213> ORGANISM: Artificial Sequence
<220> FEATURE:
<223> OTHER INFORMATION: Modified immunoglobulin moiety.
<220> FEATURE:
<221> NAME/KEY: CDS
<222> LOCATION: (1)...(696)

```
<400> SEQUENCE: 27 gag ccc aga tct tca gac aaa act cac aca tgc cca ccg tgc cca gca      48
Glu Pro Arg Ser Ser Asp Lys Thr His Thr Cys Pro Pro Cys Pro Ala
 1               5                  10                  15 cct gaa gcc gag ggg gca ccg tca gtc ttc ctc ttc ccc cca aaa ccc      96
Pro Glu Ala Glu Gly Ala Pro Ser Val Phe Leu Phe Pro Pro Lys Pro
             20                  25                  30 aag gac acc ctc atg atc tcc cgg acc cct gag gtc aca tgc gtg gtg     144
Lys Asp Thr Leu Met Ile Ser Arg Thr Pro Glu Val Thr Cys Val Val
         35                  40                  45 gtg gac gtg agc cac gaa gac cct gag gtc aag ttc aac tgg tac gtg     192
Val Asp Val Ser His Glu Asp Pro Glu Val Lys Phe Asn Trp Tyr Val
     50                  55                  60 gac ggc gtg gag gtg cat aat gcc aag aca aag ccg cgg gag gag cag     240
Asp Gly Val Glu Val His Asn Ala Lys Thr Lys Pro Arg Glu Glu Gln
 65                  70                  75                  80 tac aac agc acg tac cgt gtg gtc agc gtc ctc acc gtc ctg cac cag     288
Tyr Asn Ser Thr Tyr Arg Val Val Ser Val Leu Thr Val Leu His Gln
                 85                  90                  95 gac tgg ctg aat ggc aag gag tac aag tgc aag gtc tcc aac aaa gcc     336
Asp Trp Leu Asn Gly Lys Glu Tyr Lys Cys Lys Val Ser Asn Lys Ala
            100                 105                 110 ctc cca tcc tcc atc gag aaa acc atc tcc aaa gcc aaa ggg cag ccc     384
Leu Pro Ser Ser Ile Glu Lys Thr Ile Ser Lys Ala Lys Gly Gln Pro
        115                 120                 125 cga gaa cca cag gtg tac acc ctg ccc cca tcc cgg gat gag ctg acc     432
Arg Glu Pro Gln Val Tyr Thr Leu Pro Pro Ser Arg Asp Glu Leu Thr
    130                 135                 140 aag aac cag gtc agc ctg acc tgc ctg gtc aaa ggc ttc tat ccc agc     480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac     528
Asp Ile Ala Val Glu Trp Glu Ser Asn Gly Gln Pro Glu Asn Asn Tyr
                165                 170                 175 aag acc acg cct ccc gtg ctg gac tcc gac ggc tcc ttc ttc ctc tac     576
Lys Thr Thr Pro Pro Val Leu Asp Ser Asp Gly Ser Phe Phe Leu Tyr
            180                 185                 190 agc aag ctc acc gtg gac aag agc agg tgg cag cag ggg aac gtc ttc     624
Ser Lys Leu Thr Val Asp Lys Ser Arg Trp Gln Gln Gly Asn Val Phe
        195                 200                 205 tca tgc tcc gtg atg cat gag gct ctg cac aac cac tac acg cag aag     672
Ser Cys Ser Val Met His Glu Ala Leu His Asn His Tyr Thr Gln Lys
    210                 215                 220 agc ctc tcc ctg tct ccg ggt aaa taatctagag gcgcgccaat ta            718
Ser Leu Ser Leu Ser Pro Gly Lys
225                 230

<210> SEQ ID NO 28
<211> LENGTH: 232
<212> TYPE: PRT
<213> ORGANISM: Artificial Sequence
<220> FEATURE:
<223> OTHER INFORMATION: Modified immunoglobulin moiety.

<400> SEQUENCE: 28

Glu Pro Arg Ser Ser Asp Lys Thr His Thr Cys Pro Pro Cys Pro Ala
 1               5                  10                  15

Pro Glu Ala Glu Gly Ala Pro Ser Val Phe Leu Phe Pro Pro Lys Pro
             20                  25                  30
```

-continued

Lys Asp Thr Leu Met Ile Ser Arg Thr Pro Glu Val Thr Cys Val Val
              35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                  85                  90                  95

Asp Trp Leu Asn Gly Lys Glu Tyr Lys Cys Lys Val Ser Asn Lys Ala
                 100                 105                 110

Leu Pro Ser Ser Ile Glu Lys Thr Ile Ser Lys Ala Lys Gly Gln Pro
             115                 120                 125

Arg Glu Pro Gln Val Tyr Thr Leu Pro Pro Ser Arg Asp Glu Leu Thr
         130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                 165                 170                 175

Lys Thr Thr Pro Pro Val Leu Asp Ser Asp Gly Ser Phe Phe Leu Tyr
             180                 185                 190

Ser Lys Leu Thr Val Asp Lys Ser Arg Trp Gln Gln Gly Asn Val Phe
         195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 29
<211> LENGTH: 36
<212> TYPE: DNA
<213> ORGANISM: Artificial Sequence
<220> FEATURE:
<223> OTHER INFORMATION: PCR primer.

<400> SEQUENCE: 29
gagcccaaat cttcagacaa aactcacaca tgccca                                36

<210> SEQ ID NO 30
<211> LENGTH: 36
<212> TYPE: DNA
<213> ORGANISM: Artificial Sequence
<220> FEATURE:
<223> OTHER INFORMATION: PCR primer.

<400> SEQUENCE: 30
taattggcgc gcctctagat tatttacccg gagaca                                36

<210> SEQ ID NO 31
<211> LENGTH: 718
<212> TYPE: DNA
<213> ORGANISM: Artificial Sequence
<220> FEATURE:
<223> OTHER INFORMATION: Modified immunoglobulin moiety.
<220> FEATURE:
<221> NAME/KEY: CDS
<222> LOCATION: (1)...(696)

<400> SEQUENCE: 31

```
gag ccc aaa tct tca gac aaa act cac aca tgc cca ccg tgc cca gca       48
Glu Pro Lys Ser Ser Asp Lys Thr His Thr Cys Pro Pro Cys Pro Ala
1               5                   10                  15 cct gaa gcc gag ggg gca ccg tca gtc ttc ctc ttc ccc cca aaa ccc       96
Pro Glu Ala Glu Gly Ala Pro Ser Val Phe Leu Phe Pro Pro Lys Pro
            20                  25                  30 aag gac acc ctc atg atc tcc cgg acc cct gag gtc aca tgc gtg gtg      144
Lys Asp Thr Leu Met Ile Ser Arg Thr Pro Glu Val Thr Cys Val Val
        35                  40                  45 gtg gac gtg agc cac gaa gac cct gag gtc aag ttc aac tgg tac gtg      192
Val Asp Val Ser His Glu Asp Pro Glu Val Lys Phe Asn Trp Tyr Val
50                  55                  60 gac ggc gtg gag gtg cat aat gcc aag aca aag ccg cgg gag gag cag      240
Asp Gly Val Glu Val His Asn Ala Lys Thr Lys Pro Arg Glu Glu Gln
65                  70                  75                  80 tac aac agc acg tac cgt gtg gtc agc gtc ctc acc gtc ctg cac cag      288
Tyr Asn Ser Thr Tyr Arg Val Val Ser Val Leu Thr Val Leu His Gln
                85                  90                  95 gac tgg ctg aat ggc aag gag tac aag tgc aag gtc tcc aac aaa gcc      336
Asp Trp Leu Asn Gly Lys Glu Tyr Lys Cys Lys Val Ser Asn Lys Ala
            100                 105                 110 ctc cca tcc tcc atc gag aaa acc atc tcc aaa gcc aaa ggg cag ccc      384
Leu Pro Ser Ser Ile Glu Lys Thr Ile Ser Lys Ala Lys Gly Gln Pro
        115                 120                 125 cga gaa cca cag gtg tac acc ctg ccc cca tcc cgg gat gag ctg acc      432
Arg Glu Pro Gln Val Tyr Thr Leu Pro Pro Ser Arg Asp Glu Leu Thr
    130                 135                 140 aag aac cag gtc agc ctg acc tgc ctg gtc aaa ggc ttc tat ccc agc      480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac      528
Asp Ile Ala Val Glu Trp Glu Ser Asn Gly Gln Pro Glu Asn Asn Tyr
                165                 170                 175 aag acc acg cct ccc gtg ctg gac tcc gac ggc tcc ttc ttc ctc tac      576
Lys Thr Thr Pro Pro Val Leu Asp Ser Asp Gly Ser Phe Phe Leu Tyr
            180                 185                 190 agc aag ctc acc gtg gac aag agc agg tgg cag cag ggg aac gtc ttc      624
Ser Lys Leu Thr Val Asp Lys Ser Arg Trp Gln Gln Gly Asn Val Phe
        195                 200                 205 tca tgc tcc gtg atg cat gag gct ctg cac aac cac tac acg cag aag      672
Ser Cys Ser Val Met His Glu Ala Leu His Asn His Tyr Thr Gln Lys
    210                 215                 220 agc ctc tcc ctg tct ccg ggt aaa taatctagag gcgcgccaat ta             718
Ser Leu Ser Leu Ser Pro Gly Lys
225                 230
```

<210> SEQ ID NO 32
<211> LENGTH: 232
<212> TYPE: PRT
<213> ORGANISM: Artificial Sequence
<220> FEATURE:
<223> OTHER INFORMATION: Modified immunoglobulin moiety.

<400> SEQUENCE: 32

```
Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30
```

```
Lys Asp Thr Leu Met Ile Ser Arg Thr Pro Glu Val Thr Cys Val Val
         35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
             100                 105                 110

Leu Pro Ser Ser Ile Glu Lys Thr Ile Ser Lys Ala Lys Gly Gln Pro
         115                 120                 125

Arg Glu Pro Gln Val Tyr Thr Leu Pro Pro Ser Arg Asp Glu Leu Thr
     130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 33
<211> LENGTH: 18
<212> TYPE: DNA
<213> ORGANISM: Artificial Sequence
<220> FEATURE:
<223> OTHER INFORMATION: PCR primer.

<400> SEQUENCE: 33
ggccggccac catgggat                                                        18

<210> SEQ ID NO 34
<211> LENGTH: 27
<212> TYPE: DNA
<213> ORGANISM: Artificial Sequence
<220> FEATURE:
<223> OTHER INFORMATION: PCR primer.

<400> SEQUENCE: 34
tcgcctcata gagaggacac ctgcagt                                              27

<210> SEQ ID NO 35
<211> LENGTH: 28
<212> TYPE: DNA
<213> ORGANISM: Artificial Sequence
<220> FEATURE:
<223> OTHER INFORMATION: PCR primer.

<400> SEQUENCE: 35
gtcctctcta tgaggcgagg gccccgga                                             28
```

```
<210> SEQ ID NO 36
<211> LENGTH: 27
<212> TYPE: DNA
<213> ORGANISM: Artificial Sequence
<220> FEATURE:
<223> OTHER INFORMATION: PCR primer.

<400> SEQUENCE: 36
cggcgtgcgt aggagcccgc aggccac                                           27

<210> SEQ ID NO 37
<211> LENGTH: 29
<212> TYPE: DNA
<213> ORGANISM: Artificial Sequence
<220> FEATURE:
<223> OTHER INFORMATION: PCR primer.

<400> SEQUENCE: 37
gggctcctac gcacgccgcg gccgaaacc                                         29

<210> SEQ ID NO 38
<211> LENGTH: 37
<212> TYPE: DNA
<213> ORGANISM: Artificial Sequence
<220> FEATURE:
<223> OTHER INFORMATION: PCR primer.

<400> SEQUENCE: 38
ggaaccacgc ggaaccagcg ccgcctcgcc ggccccc                                37

<210> SEQ ID NO 39
<211> LENGTH: 36
<212> TYPE: DNA
<213> ORGANISM: Artificial Sequence
<220> FEATURE:
<223> OTHER INFORMATION: PCR primer.

<400> SEQUENCE: 39
ctggttccgc gtggttccga gcccaaatct tcagac                                 36

<210> SEQ ID NO 40
<211> LENGTH: 31
<212> TYPE: DNA
<213> ORGANISM: Artificial Sequence
<220> FEATURE:
<223> OTHER INFORMATION: PCR primer.

<400> SEQUENCE: 40
ggcgcgcctc tagattattt acccggagac a                                      31

<210> SEQ ID NO 41
<211> LENGTH: 987
<212> TYPE: DNA
<213> ORGANISM: Artificial Sequence
<220> FEATURE:
<223> OTHER INFORMATION: Ztnfr12-tcs-Fc5.
<220> FEATURE:
<221> NAME/KEY: CDS
<222> LOCATION: (1)...(984)

<400> SEQUENCE: 41 atg gga tgg agc tgg atc ttt ctc ttt ctt ctg tca gga act gca ggt         48
Met Gly Trp Ser Trp Ile Phe Leu Phe Leu Leu Ser Gly Thr Ala Gly
 1               5                  10                  15 gtc ctc tct atg agg cga ggg ccc cgg agc ctg cgg ggc agg gac gcg         96
Val Leu Ser Met Arg Arg Gly Pro Arg Ser Leu Arg Gly Arg Asp Ala
             20                  25                  30
```

```
cca gcc ccc acg ccc tgc gtc ccg gcc gag tgc ttc gac ctg ctg gtc      144
Pro Ala Pro Thr Pro Cys Val Pro Ala Glu Cys Phe Asp Leu Leu Val
         35                  40                  45 cgc cac tgc gtg gcc tgc ggg ctc cta cgc acg ccg cgg ccg aaa ccg      192
Arg His Cys Val Ala Cys Gly Leu Leu Arg Thr Pro Arg Pro Lys Pro
     50                  55                  60 gcc ggg gcc agc agc cct gcg ccc agg acg gcg ctg cag ccg cag gag      240
Ala Gly Ala Ser Ser Pro Ala Pro Arg Thr Ala Leu Gln Pro Gln Glu
 65                  70                  75                  80 tcg gtg ggc gcg ggg gcc ggc gag gcg gcg ctg gtt ccg cgt ggt tcc      288
Ser Val Gly Ala Gly Ala Gly Glu Ala Ala Leu Val Pro Arg Gly Ser
                 85                  90                  95 gag ccc aaa tct tca gac aaa act cac aca tgc cca ccg tgc cca gca      336
Glu Pro Lys Ser Ser Asp Lys Thr His Thr Cys Pro Pro Cys Pro Ala
             100                 105                 110 cct gaa gcc gag ggg gca ccg tca gtc ttc ctc ttc ccc cca aaa ccc      384
Pro Glu Ala Glu Gly Ala Pro Ser Val Phe Leu Phe Pro Pro Lys Pro
         115                 120                 125 aag gac acc ctc atg atc tcc cgg acc cct gag gtc aca tgc gtg gtg      432
Lys Asp Thr Leu Met Ile Ser Arg Thr Pro Glu Val Thr Cys Val Val
 130                 135                 140 gtg gac gtg agc cac gaa gac cct gag gtc aag ttc aac tgg tac gtg      480
Val Asp Val Ser His Glu Asp Pro Glu Val Lys Phe Asn Trp Tyr Val
145                 150                 155                 160 gac ggc gtg gag gtg cat aat gcc aag aca aag ccg cgg gag gag cag      528
Asp Gly Val Glu Val His Asn Ala Lys Thr Lys Pro Arg Glu Glu Gln
                165                 170                 175 tac aac agc acg tac cgt gtg gtc agc gtc ctc acc gtc ctg cac cag      576
Tyr Asn Ser Thr Tyr Arg Val Val Ser Val Leu Thr Val Leu His Gln
            180                 185                 190 gac tgg ctg aat ggc aag gag tac aag tgc aag gtc tcc aac aaa gcc      624
Asp Trp Leu Asn Gly Lys Glu Tyr Lys Cys Lys Val Ser Asn Lys Ala
        195                 200                 205 ctc cca tcc tcc atc gag aaa acc atc tcc aaa gcc aaa ggg cag ccc      672
Leu Pro Ser Ser Ile Glu Lys Thr Ile Ser Lys Ala Lys Gly Gln Pro
    210                 215                 220 cga gaa cca cag gtg tac acc ctg ccc cca tcc cgg gat gag ctg acc      720
Arg Glu Pro Gln Val Tyr Thr Leu Pro Pro Ser Arg Asp Glu Leu Thr
225                 230                 235                 240 aag aac cag gtc agc ctg acc tgc ctg gtc aaa ggc ttc tat ccc agc      768
Lys Asn Gln Val Ser Leu Thr Cys Leu Val Lys Gly Phe Tyr Pro Ser
                245                 250                 255 gac atc gcc gtg gag tgg gag agc aat ggg cag ccg gag aac aac tac      816
Asp Ile Ala Val Glu Trp Glu Ser Asn Gly Gln Pro Glu Asn Asn Tyr
            260                 265                 270 aag acc acg cct ccc gtg ctg gac tcc gac ggc tcc ttc ttc ctc tac      864
Lys Thr Thr Pro Pro Val Leu Asp Ser Asp Gly Ser Phe Phe Leu Tyr
        275                 280                 285 agc aag ctc acc gtg gac aag agc agg tgg cag cag ggg aac gtc ttc      912
Ser Lys Leu Thr Val Asp Lys Ser Arg Trp Gln Gln Gly Asn Val Phe
    290                 295                 300 tca tgc tcc gtg atg cat gag gct ctg cac aac cac tac acg cag aag      960
Ser Cys Ser Val Met His Glu Ala Leu His Asn His Tyr Thr Gln Lys
305                 310                 315                 320 agc ctc tcc ctg tct ccg ggt aaa taa                                  987
Ser Leu Ser Leu Ser Pro Gly Lys
                325
```

```
<210> SEQ ID NO 42
<211> LENGTH: 328
<212> TYPE: PRT
<213> ORGANISM: Artificial Sequence
<220> FEATURE:
<223> OTHER INFORMATION: Ztnfr12-tcs-Fc5.

<400> SEQUENCE: 42

Met Gly Trp Ser Trp Ile Phe Leu Phe Leu Leu Ser Gly Thr Ala Gly
 1               5                  10                  15

Val Leu Ser Met Arg Arg Gly Pro Arg Ser Leu Arg Gly Arg Asp Ala
            20                  25                  30

Pro Ala Pro Thr Pro Cys Val Pro Ala Glu Cys Phe Asp Leu Leu Val
        35                  40                  45

Arg His Cys Val Ala Cys Gly Leu Leu Arg Thr Pro Arg Pro Lys Pro
    50                  55                  60

Ala Gly Ala Ser Ser Pro Ala Pro Arg Thr Ala Leu Gln Pro Gln Glu
65                  70                  75                  80

Ser Val Gly Ala Gly Ala Gly Glu Ala Ala Leu Val Pro Arg Gly Ser
                85                  90                  95

Glu Pro Lys Ser Ser Asp Lys Thr His Thr Cys Pro Pro Cys Pro Ala
            100                 105                 110

Pro Glu Ala Glu Gly Ala Pro Ser Val Phe Leu Phe Pro Pro Lys Pro
        115                 120                 125

Lys Asp Thr Leu Met Ile Ser Arg Thr Pro Glu Val Thr Cys Val Val
    130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ser Ser Ile Glu Lys Thr Ile Ser Lys Ala Lys Gly Gln Pro
    210                 215                 220

Arg Glu Pro Gln Val Tyr Thr Leu Pro Pro Ser Arg Asp Glu Leu Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Tyr
        275                 280                 285

Ser Lys Leu Thr Val Asp Lys Ser Arg Trp Gln Gln Gly Asn Val Phe
    290                 295                 300

Ser Cys Ser Val Met His Glu Ala Leu His Asn His Tyr Thr Gln Lys
305                 310                 315                 320

Ser Leu Ser Leu Ser Pro Gly Lys
                325

<210> SEQ ID NO 43
<211> LENGTH: 36
<212> TYPE: DNA
<213> ORGANISM: Artificial Sequence
<220> FEATURE:
<223> OTHER INFORMATION: PCR primer.
```

```
<400> SEQUENCE: 43
atgcattccg gaatgaggcg agggccccgg agcctg                              36

<210> SEQ ID NO 44
<211> LENGTH: 54
<212> TYPE: DNA
<213> ORGANISM: Artificial Sequence
<220> FEATURE:
<223> OTHER INFORMATION: PCR primer.

<400> SEQUENCE: 44
atgcattcta gatcagtcca tcggcatgta ttccgccgcc tcgccggccc ccgc          54

<210> SEQ ID NO 45
<211> LENGTH: 6
<212> TYPE: PRT
<213> ORGANISM: Artificial Sequence
<220> FEATURE:
<223> OTHER INFORMATION: C-terminal tag.

<400> SEQUENCE: 45

Glu Tyr Met Pro Met Asp
 1               5

<210> SEQ ID NO 46
<211> LENGTH: 17
<212> TYPE: PRT
<213> ORGANISM: Artificial Sequence
<220> FEATURE:
<223> OTHER INFORMATION: Motif.
<220> FEATURE:
<221> NAME/KEY: VARIANT
<222> LOCATION: (2)...(2)
<223> OTHER INFORMATION: Xaa = N, V, P, or S.
<220> FEATURE:
<221> NAME/KEY: VARIANT
<222> LOCATION: (3)...(3)
<223> OTHER INFORMATION: Xaa = Q, P, or E.
<220> FEATURE:
<221> NAME/KEY: VARIANT
<222> LOCATION: (4)...(4)
<223> OTHER INFORMATION: Xaa = T, A, E, or N.
<220> FEATURE:
<221> NAME/KEY: VARIANT
<222> LOCATION: (5)...(5)
<223> OTHER INFORMATION: Xaa = E or Q.
<220> FEATURE:
<221> NAME/KEY: VARIANT
<222> LOCATION: (6)...(6)
<223> OTHER INFORMATION: Xaa = C or Y.
<220> FEATURE:
<221> NAME/KEY: VARIANT
<222> LOCATION: (7)...(7)
<223> OTHER INFORMATION: Xaa = F or W.
<220> FEATURE:
<221> NAME/KEY: VARIANT
<222> LOCATION: (9)...(9)
<223> OTHER INFORMATION: Xaa = P, L, or S.
<220> FEATURE:
<221> NAME/KEY: VARIANT
<222> LOCATION: (11)...(11)
<223> OTHER INFORMATION: Xaa = V or L.
<220> FEATURE:
<221> NAME/KEY: VARIANT
<222> LOCATION: (12)...(12)
<223> OTHER INFORMATION: Xaa = R, G, or H.
<220> FEATURE:
<221> NAME/KEY: VARIANT
<222> LOCATION: (13)...(13)
<223> OTHER INFORMATION: Xaa = N, H, T, or A.
```

```
<220> FEATURE:
<221> NAME/KEY: VARIANT
<222> LOCATION: (15)...(15)
<223> OTHER INFORMATION: Xaa = V, M, or I.
<220> FEATURE:
<221> NAME/KEY: VARIANT
<222> LOCATION: (16)...(16)
<223> OTHER INFORMATION: Xaa = S, A, or P.

<400> SEQUENCE: 46

Cys Xaa Xaa Xaa Xaa Xaa Xaa Asp Xaa Leu Xaa Xaa Xaa Cys Xaa Xaa
 1               5                  10                  15

Cys
```